US009376725B1

(12) United States Patent
Friesen et al.

(10) Patent No.: US 9,376,725 B1
(45) Date of Patent: Jun. 28, 2016

(54) METHODS OF SCREENING FOR COMPOUNDS FOR TREATING MUSCULAR DYSTROPHY USING HUMAN ALPHA7 INTEGRIN MRNA TRANSLATION REGULATION

(71) Applicant: PTC Therapeutics, Inc., South Plainfield, NJ (US)

(72) Inventors: Westley J. Friesen, Huntingdon Valley, PA (US); Nikolai Naryshkin, East Brunswick, NJ (US); Meenal Patel, Fairless Hills, PA (US); Charles Romfo, Easton, PA (US); Yuki Tomizawa, Edison, NJ (US); Ellen Welch, Califon, NJ (US); Jin Zhuo, Belle Mead, NJ (US)

(73) Assignee: PTC THERAPEUTICS, INC., South Plainfield, NJ (US)

( * ) Notice: Subject to any disclaimer, the term of this patent is extended or adjusted under 35 U.S.C. 154(b) by 92 days.

(21) Appl. No.: 14/260,873

(22) Filed: Apr. 24, 2014

Related U.S. Application Data

(62) Division of application No. 13/646,943, filed on Oct. 8, 2012, now Pat. No. 8,741,572, which is a division of application No. 12/143,705, filed on Jun. 20, 2008, now Pat. No. 8,283,115.

(60) Provisional application No. 60/936,632, filed on Jun. 20, 2007.

(51) Int. Cl.
   *C12Q 1/68*     (2006.01)
   *C12N 15/113*    (2010.01)
   *C12N 15/82*     (2006.01)
   *C07K 14/705*    (2006.01)

(52) U.S. Cl.
CPC .......... *C12Q 1/6897* (2013.01); *C12N 15/1138* (2013.01); *C12N 15/8209* (2013.01); *C07K 14/70546* (2013.01)

(58) Field of Classification Search
None
See application file for complete search history.

(56) References Cited

U.S. PATENT DOCUMENTS

| | | | |
|---|---|---|---|
| 3,346,381 A | 10/1967 | Grieg | |
| 5,439,797 A | 8/1995 | Tsien et al. | |
| 5,444,149 A | 8/1995 | Keene et al. | |
| 5,587,300 A | 12/1996 | Malter | |
| 5,691,145 A | 11/1997 | Pitner et al. | |
| 5,698,427 A | 12/1997 | Keene et al. | |
| 5,700,660 A | 12/1997 | Leonard et al. | |
| 5,731,343 A | 3/1998 | Feng et al. | |
| 5,776,738 A | 7/1998 | Dell'Orco, Sr. et al. | |
| 5,843,770 A | 12/1998 | Ill et al. | |
| 5,849,520 A | 12/1998 | Leonard et al. | |
| 5,859,227 A | 1/1999 | Giordano et al. | |
| 5,908,779 A | 6/1999 | Carmichael et al. | |
| 5,928,888 A | 7/1999 | Whitney | |
| 5,990,298 A | 11/1999 | Carmichael et al. | |
| 6,004,749 A | 12/1999 | Giordano et al. | |
| 6,010,856 A | 1/2000 | Ulevitch et al. | |
| 6,057,437 A | 5/2000 | Kamiya et al. | |
| 6,107,029 A | 8/2000 | Giordano | |
| 6,159,709 A | 12/2000 | Korneluk et al. | |
| 6,171,821 B1 | 1/2001 | Korneluk et al. | |
| 6,203,982 B1 | 3/2001 | Nunokawa et al. | |
| 6,214,563 B1 | 4/2001 | Negulescu et al. | |
| 6,221,587 B1 | 4/2001 | Ecker et al. | |
| 6,221,612 B1 | 4/2001 | Knapp et al. | |
| 6,232,070 B1 | 5/2001 | Shuman | |
| 6,265,167 B1 | 7/2001 | Carmichael et al. | |
| 6,265,546 B1 | 7/2001 | Cohen et al. | |
| 6,284,882 B1 | 9/2001 | Wu-Wong et al. | |
| 6,303,295 B1 | 10/2001 | Taylor et al. | |
| 6,331,170 B1 | 12/2001 | Ordway | |
| 6,331,396 B1 | 12/2001 | Silverman et al. | |
| 6,399,373 B1 | 6/2002 | Bougueleret | |
| 6,448,007 B1 | 9/2002 | Giordano et al. | |
| 6,455,280 B1 | 9/2002 | Edwards et al. | |
| 6,465,176 B1 | 10/2002 | Giordano et al. | |
| 6,476,208 B1 | 11/2002 | Cohen et al. | |
| 6,528,060 B1 | 3/2003 | Nicolette | |
| 6,617,493 B1 | 9/2003 | Fader | |
| 6,627,797 B1 | 9/2003 | Duvick et al. | |
| 6,630,589 B1 | 10/2003 | Giordano et al. | |
| 6,635,671 B1 | 10/2003 | Kastelic et al. | |
| 6,638,522 B1 | 10/2003 | Mulye | |
| 6,645,747 B1 | 11/2003 | Hallahan et al. | |
| 6,653,132 B1 | 11/2003 | Keshet et al. | |
| 6,667,152 B2 | 12/2003 | Miles et al. | |
| 6,872,850 B2 | 3/2005 | Giordano et al. | |
| 7,078,171 B2 | 7/2006 | Giordano et al. | |
| 7,371,726 B2 | 5/2008 | Junker et al. | |

(Continued)

FOREIGN PATENT DOCUMENTS

EP      1 179 196      1/2002
EP      1 604 011      12/2005

(Continued)

OTHER PUBLICATIONS

Leung et al., Biochem. Biophys. Res Commun. 243: 317325 (1998).*
U.S. Appl. No. 12/143,705, filed Jun. 20, 2008, Friesen et al.
U.S. Appl. No. 12/143,697, filed Jun. 20, 2008, Friesen et al.
Adams et al., 1998, "Localized infusion of IGF-I results in skeletal muscle hypertrophy in rats." J Appl Physiol, 84:1716-1722.
Afounda et al., 1999, "Localized XId3 mRNA activation in Xenopus embryos by cytoplasmic polyadenylation." Mech Dev., 88(1):15-31.
Aharon & Schneider, 1993, "Selective destabilization of short-lived mRNAs with the granulocyte-macrophage colony-stimulating factor AU-rich 3' noncoding region is mediated by a cotranslational mechanism" Mol. Cell. Biol., 13: 1971-1980.

(Continued)

*Primary Examiner* — Robert C Hayes
(74) *Attorney, Agent, or Firm* — Jones Day

(57) ABSTRACT

The present invention provides compounds and assays for the identification and validation of compounds for use in the treatment of muscular mystrophy (MD), or a form thereof, in which said compounds increase the post-transcriptional expression of a target gene (i.e., mIGF1, ITGA7, or UTRN).

16 Claims, 8 Drawing Sheets

(56) References Cited

U.S. PATENT DOCUMENTS

| | | | |
|---|---|---|---|
| 7,601,840 | B2 | 10/2009 | Moon et al. |
| 7,767,689 | B2 | 8/2010 | Moon et al. |
| 2002/0006661 | A1 | 1/2002 | Green et al. |
| 2002/0132257 | A1 | 9/2002 | Giordano et al. |
| 2003/0135870 | A1 | 7/2003 | Cheikh et al. |
| 2003/0199453 | A1 | 10/2003 | Giordano et al. |
| 2004/0063120 | A1 | 4/2004 | Beer et al. |
| 2004/0091866 | A1 | 5/2004 | Giordano et al. |
| 2004/0138282 | A1 | 7/2004 | Greig et al. |
| 2004/0152117 | A1 | 8/2004 | Giordano et al. |
| 2004/0214223 | A1 | 10/2004 | Cao et al. |
| 2004/0231007 | A1 | 11/2004 | Kastelic et al. |
| 2005/0048549 | A1 | 3/2005 | Cao et al. |
| 2007/0072186 | A1 | 3/2007 | Mehta et al. |
| 2007/0111203 | A1 | 5/2007 | Cao et al. |
| 2007/0254878 | A1 | 11/2007 | Cao et al. |
| 2008/0064683 | A1 | 3/2008 | Cao et al. |
| 2009/0068654 | A1 | 3/2009 | Kastelic et al. |

FOREIGN PATENT DOCUMENTS

| | | |
|---|---|---|
| EP | 1 761 638 | 3/2007 |
| GB | 9828707.1 | 12/1998 |
| GB | 9828709.7 | 12/1998 |
| WO | WO 95/33831 | 12/1995 |
| WO | WO 97/25860 | 7/1997 |
| WO | WO 98/39484 | 9/1998 |
| WO | WO 93/20212 | 10/1999 |
| WO | WO 00/04051 | 1/2000 |
| WO | WO 00/05356 | 2/2000 |
| WO | WO 00/39314 | 7/2000 |
| WO | WO 00/46247 | 8/2000 |
| WO | WO 01/84155 | 8/2001 |
| WO | WO 02/48150 | 6/2002 |
| WO | WO 02/077609 | 10/2002 |
| WO | WO 02/083953 | 10/2002 |
| WO | WO 03/087815 | 10/2003 |
| WO | WO 2004/065561 | 8/2004 |
| WO | WO 2005/049868 | 6/2005 |
| WO | WO 2005/095615 | 10/2005 |
| WO | WO 2005/118857 | 12/2005 |
| WO | WO 2006/022712 | 3/2006 |

OTHER PUBLICATIONS

Akashi et al., 1994, "Number and Location of AUUUA Motifs: Role in Regulating Transiently Expressed RNAs." Blood, 83:3182-3187.
Akiri et al., 1998, Regulation of Vascular Endothelial Growth Factor (VEGF) Expression is Mediated by Internal Initiation of Translation and Alternative Initiation of Transcription. Oncogene, 17:227-236.
Amara et al., 1999, "TGF-beta(1), regulation of alzheimer amyloid precursor protein mRNA expression in a normal human astrocyte cell line: mRNA stabilization." Brain Res. Mol. Brain Res., 71(1):42-49.
Avila et al., 2007 "Trichostatin A increases SMN expression and survival in a mouse model of spinal muscular atrophy", J Clin Invest. ;117(3):659-71.
Banholzer et al., 1997, "Rapamycin destabilizes interleukin-3 mRNA in autocrine tumor cells by a mechanism requiring an intact 3' untranslated region." Molecular and Cellular Biology, 17: 3254-3260.
Barkoff et al., 2000, "Translational control of cyclin B1 mRNA during meiotic maturation: coordinated repression and cytoplasmic polyadenylation", Dev Biol., 220(1):97-109.
Barton et al., 2002, "Muscle-specific expression of insulin-like growth factor I counters muscle decline in mdx mice", J. Cell Biol., 157:137-148.
Barton-Davis, 1998, "Viral mediated expression of insulin-like growth factor I blocks the aging-related loss of skeletal muscle function", PNAS, 95:15603-15607.
Bashaw & Baker, 1995, "The msl-2 dosage compensation gene of Drosophila encodes a putative DNA-binding protein whose expression is sex specifically regulated by Sex-lethal", Develop., 121(10):3245-3258.

Beelman & Parker, 1994, "Differential effects of translational inhibition in cis and in trans on the decay of the unstable yeast MFA2 mRNA", J. Biol. Chem, 269:9687-9692.
Benjamin et al., 1997, "Conditional switching of vascular endothelial growth factor (VEGF) expression in tumors: induction of endothelial cell shedding and regression of hemangioblastoma-like vessels by VEGF withdrawal" Proc. Natl. Acad Sci 94:8761-8766.
Bergsten & Gavis, 1999, "Role for mRNA localization in translational activation but not spatial restriction of nanos RNA", Develop., 126(4):659-669.
Bertini et al., 2005, "134th ENMC International Workshop: Outcome Measures and Treatment of Spinal Muscular Atrophy, Feb. 11-13, 2005, Naarden, The Netherlands", Neuromuscul Disord. 15(11):802-16.
Beutler et al., 1988, "Assay of Ribonuclease that preferentially hydrolyses mRNAs Containing Cytokine-Derived UA-Rich Instability Sequences", Biochem. Biophys Res. Commun., 152:973-980.
Bhattacharyya et al., 2007, "Mining the GEMS—a novel platform technology targeting post-transcriptional control mechanisms", Drug Discov Today, 12(13-14):553-60.
Boda et al., 2004, "Survival motor neuron SMN1 and SMN2 gene promoters: identical sequences and differential expression in neurons and non-neuronal cells", Eur J Hum Genet.; 12(9):729-37.
Bogdanovich et al., 2004, "Therapeutics for Duchenne muscular dystrophy: current approaches and future directions", J Mol Med., 82(2):102-15.
Bornes et al., 2004, "Control of the Vascular Endothelial growth factor internal ribosome entry site (IRES) Activity and translation initiation by Alternativey Spliced Coding sequences", J Biol. Chem., 279(18):18717-18726.
Brahe et al., 2005, "Phenylbutyrate increases SMN gene expression in spinal muscular atrophy patients", Eur J Hum Genet.; 13(2):256-9.
Brenchley, 1998, "Antagonising the expression of VEGF in pathological angiogenesis," Exp. Opin Ther. Patents 8(12): 1695-1706.
Brennan & Seitz, 2001, "HuR and mRNA stability." Cell. Mol. Life. Sci., 58:266-277.
Burkin and Kaufman, 1999, "The α7β1 integrin in muscle development and disease", Cell Tissue Res., 296:183-190.
Carballo et al., 1998, "Feedback inhibition of macrophage tumor necrosis factor-alpha production by tristetraprolin", Science, 281:1001-1005.
Castagnetti et al., 2000, "Control of oskar mRNA translation by Bruno in a novel cell-free system from Drosophila ovaries", Develop., 127(5):1063-1068.
Chakkalakal et al., 2005, "Molecular, cellular, and pharmacological therapies for Duchenne/Becker muscular dystrophies", FASEB J., 19(8):880-91.
Charlesworth et al., 2000, "The temporal control of Wee1 mRNA translation during Xenopus oocyte maturation is regulated by cytoplasmic polyadenylation elements within the 3'-untranslated region", Dev. Biol., 227(2): 706-719.
Chen et al., 1994, "Interplay of two functionally and structurally distinct domains of the c-fos AU-rich element specifies its mRNA-destabilizing function", Mol. Cell. Biol. 14:416-426.
Chen et al., 1994, "Selective Degradation of Early-Response-Gene mRNAs: Functional Analyses of Sequence Features of the AU-rich elements", Mol. Cell. Biol., 14: 8471-8482.
Chen et al., 1995, "AU-rich elements: characterization and importance in mRNA degradation", Trends Biochem. Sci., 20:465-470.
Chen et al., 1995, "mRNA decay mediated by two distinct AU-rich elements from c-fos and granulocyte-macrophage colony-stimulating factor transcripts: different deadenylation kinetics and uncoupling from translation", Mol. Cell. Biol., 15:5777-5788.
Chen et al., 2001, "AU Binding Proteins Recruit the Exosome to Degrade ARE-Containing mRNAs", Cell, 107: 451-464.
Child et al., 1999, "Cell type-dependent and -independent control of *HER-2/neu* translation", Int Journal of Biochem & Cell Biol., 31:201-213.
Cho et al., 2002, "Emerging techniques for the discovery and validation of therapeutic targets for skeletal diseases" Expert Opin. Ther. Targets, 6(6):679-689.

(56) References Cited

OTHER PUBLICATIONS

Claffey et al., 1998, "Identification of a human VPF/VEGF 3' untranslated region mediating hypoxia-induced mRNA stability", Mol. Biol. of Cell., 9:469-481.
Clark et al., 2000, "Synthesis of the posterior determinant Nanos is spatially restricted by a novel cotranslational regulatory mechanism", Curr. Biol., 10(20):1311-1314.
Clark et al., 2002, "A common translational control mechanism functions in axial patterning and neuroendocrine signaling in Drosophila" Develop., 129(14): 3325-3334.
Cohen et al., 1996, "Interleukin 6 induces the expression of vascular endothelial growth factor", J. Biol Chem., 271(12):736-741.
Cohen et al., 1996, "CN1-1493 inhibits monocyte/macrophage tumor necrosis factor by suppression of translation efficiency", Proc. Natl. Acad. Sci. USA, 93:3967-3971.
Coleman et al., 1995, "Myogenic Vector Expression of Insulin-like Growth Factor I Stimulates Muscle Cell Differentiation and Myofiber Hypertrophy in Transgenic Mice", J. Biol. Chem., 270:12109-12116.
Crawford et al., 1997, "The Role of 3' Poly (A) Tail Metabolism in Tumor Necrosis Factor-α Regulation," J Biol. Chem., 272:21120-21127.
Crosio et al., 2000, "La protein has a positive effect on the translation of TOP mRNAs in vivo", Nucl. Acids. Res., 28(15):2927-34.
Crucs et al., 2000, "Overlapping but distinct RNA elements control repression and activation of nanos translation", Mol. Cell., 5(3):457-467.
Curatola et al., 1995, "Rapid degradation of AU-rich element (ARE) mRNAs is activated by ribosome transit and blocked by secondary structure at any position 5' to the ARE", Mol. Cell. Biol., 15:6331-6340.
Dahanukar & Wharton, 1996, "The Nanos gradient in Drosophila embryos is generated by translational regulation", Genes Dev., 20:2610-2620.
Danner et al., 1998, "Agonist regulation of human beta2-adrenergic receptor mRNA stability occurs via a specific AU-rich element", J. Biol. Chem., 273(6):3223-9.
Database WPI Week, 2002, "Screening drug improving insulin resistance without exacerbating diabetic retinopathy, by detecting expression of reporter gene fused to promoter region of human vascular endothelial growth factor gene in mammal cell", JP 2001 340080 A.
Davies and Nowak, 2006, "Molecular Mechanisms of Muscular Dystrophies: Old and New Players", Nature, 7:762-773 (Supplementary Information Included).
De Jong et al., 2002, "RNA and RNA-protein complexes as targets for therapeutic intervention", Curr. Topics Medicinal Chem., 2:289-302.
De Wet et al., 1987, "Firefly Luciferase Gene: Structure and Expression in Mammalian Cells", Mol Cell. Biol., 7(2):725-737.
Dominski & Marzluff, 1999, "Formation of the 3' end of histone mRNA", Gene, 239(1):1-14.
Dreyfuss et al., 2002 "Messenger-RNA-Binding Proteins and the Messages they Carry", Nature Rev Molec Cell Biol., 3:195-205.
Echaniz-Laguna et al., 1999, "The promoters of the survival motor neuron gene (SMN) and its copy (SMNc) share common regulatory elements", Am J Hum Genet; 64(5):1365-70.
Eibl et al., 1999, "In vivo analysis of plastid psbA, rbcL and rpl32 UTR elements by chloroplast transformation: tobacco plastid gene expression is controlled by modulation of transcript levels and translation efficiency", Plant J. 19:333-345.
Engvall et al., 2003, "The new frontier in muscular dystrophy research: booster genes", FASEB J., 17: 1579-1584.
Fan et al., 1998, "Overepxression of HuR, a nuclear-cytoplasmic shuttling protein, increases in vivo stability of ARE-containing mRNAS", EMBO, J 17:3448-3460.
Forsythe et al., 1996, "Activation of Vascular Endothelial Growth Factor Gene Transcription by Hypoxia-Inducible Factor 1", Molec & Cell. Biol., 16(9):4604-4613.

Fortes et al., 2003, "Inhibiting expression of specific genes in mammalian cells with 5' end-mutated u1 small nuclear RNAs targeted to terminal exons of pre-mRNA", Proc. Natl. Acad. Sci., 100(14):8264-8269.
Gan et al., 1998, "Functional characterization of the internal ribosome entry site of eIF4G mRNA", J. Biol. Chem., 273:5006-5012.
Gavis et al., 1996, "A conserved 90 nucleotide element mediates translational repression of nanos RNA", Development, 122(9):2791-2800.
Ge et al., 2002, "Regulation of Promoter Activity of the APP Gene by Cytokines and Growth Factors", Ann N.Y. Acad Sci., 973:463-467.
Gebauer et al., 1998, "The Drosophila splicing regulator sex-lethal directly inhibits translation of male-specific-lethal 2 mRNA", RNA 4(2):142-150.
GENBANK Accession No. AF022375, dated Oct. 7, 1998.
GENBANK Accession No. AJ131730, dated Oct. 7, 2008.
GENBANK Accession No. M11567, dated Oct. 30, 1994.
GENBANK Accession No. M14745, dated Apr. 27, 1993.
GENBANK Accession No. M14758, dated Dec. 3, 1999.
GENBANK Accession No. M33680, dated Aug. 3, 1993.
GENBANK Accession No. M54968, dated Oct. 17, 2008.
GENBANK Accession No. M90100, dated Dec. 31, 1994.
GENBANK Accession No. NM_000230, dated Apr. 19, 2009.
GENBANK Accession No. NM_000134, dated Apr. 12, 2009.
GENBANK Accession No. NM_000162, dated Apr. 9, 2009.
GENBANK Accession No. NM_000208, dated Mar. 29, 2009.
GENBANK Accession No. NM_000247, dated Apr. 12, 2009.
GENBANK Accession No. NM_000321, dated Apr. 19, 2009.
GENBANK Accession No. NM_000418, dated Apr. 12, 2009.
GENBANK Accession No. NM_000527, dated Apr. 26, 2009.
GENBANK Accession No. NM_000572, dated Apr. 19, 2009.
GENBANK Accession No. NM_000589, dated Apr. 12, 2009.
GENBANK Accession No: NM_000600, dated Apr. 19, 2009.
GENBANK Accession No. NM_000665, dated Apr. 12, 2009.
GENBANK Accession No. NM_000758, dated Apr. 19, 2009.
GENBANK Accession No. NM_000784, dated Mar. 29, 2009.
GENBANK Accession No. NM_000791, dated Mar. 29, 2009.
GENBANK Accession No. NM_000794, dated Apr. 10, 2009.
GENBANK Accession No. NM_000799, dated Apr. 5, 2009.
GENBANK Accession No. NM_000875, dated Apr. 10, 2009.
GENBANK Accession No. NM_000899, dated Mar. 29, 2009.
GENBANK Accession No: NM_000948, dated Mar. 22, 2009.
GENBANK Accession No. NM_001145, dated Apr. 5, 2009.
GENBANK Accession No. NM_001168, dated Apr. 19, 2009.
GENBANK Accession No. NM_001240, dated Feb. 24, 2009.
GENBANK Accession No. NM_001565, dated Apr. 12, 2009.
GENBANK Accession No. NM_001567, dated Mar. 22, 2009.
GENBANK Accession No. NM_001725, dated Oct. 22, 2006.
GENBANK Accession No. NM_001728, dated Apr. 5, 2009.
GENBANK Accession No. NM_001917, dated Apr. 5, 2009.
GENBANK Accession No. NM_002006, dated Mar. 15, 2009.
GENBANK Accession No. NM_002087, dated Mar. 29, 2009.
GENBANK Accession No. NM_002111, dated Apr. 19, 2009.
GENBANK Accession No. NM_002151, dated Apr. 23, 2009.
GENBANK Accession No. NM_002231, dated Mar. 15, 2009.
GENBANK Accession No. NM_002392, dated Apr. 19, 2009.
GENBANK Accession No. NM_002632, dated Apr. 19, 2009.
GENBANK Accession No. NM_002774, dated Apr. 11, 2009.
GENBANK Accession No. NM_002925, dated Aug. 20, 2006.
GENBANK Accession No. NM_002963, dated Apr. 19, 2009.
GENBANK Accession No. NM_002964, dated Mar. 29, 2009.
GENBANK Accession No. NM_002986, dated Mar. 29, 2009.
GENBANK Accession No. NM_003255, dated Mar. 22, 2009.
GENBANK Accession No. NM_003256, dated Apr. 5, 2009.
GENBANK Accession No. NM_003355, dated Apr. 19, 2009.
GENBANK Accession No. NM_003642, dated Oct. 22, 2008.
GENBANK Accession No. NM_003883, dated Apr. 12, 2009.
GENBANK Accession No. NM_004364, dated Apr. 5, 2009.
GENBANK Accession No. NM_004395, dated Dec. 21, 2008.
GENBANK Accession No. NM_004795, dated Apr. 12, 2009.
GENBANK Accession No. NM_004797, dated Apr. 12, 2009.
GENBANK Accession No. NM_005251, dated Apr. 5, 2009.
GENBANK Accession No. NM_005252, dated Apr. 5, 2009.

(56) References Cited

OTHER PUBLICATIONS

GENBANK Accession No. NM_005417, dated Apr. 19, 2009.
GENBANK Accession No. NM_005931, dated Apr. 5, 2009.
GENBANK Accession No. NM_006536, dated Sep. 17, 2006.
GENBANK Accession No. NM_007310, dated Apr. 12, 2009.
GENBANK Accession No. NM_018727, dated Mar. 1, 2009.
GENBANK Accession No. NM_020415, dated Mar. 29, 2009.
GENBANK Accession No. NM_032611, dated Mar. 29, 2009.
GENBANK Accession No. NM_053056, dated Apr. 19, 2009.
GENBANK Accession No. NM_078467, dated Apr. 19, 2009.
GENBANK Accession No. NM_080704, dated Mar. 1, 2009.
GENBANK Accession No. NM_080705, dated Mar. 1, 2009.
GENBANK Accession No. NM_080706, dated Mar. 1, 2009.
GENBANK Accession No. NM_080881, dated Dec. 21, 2008.
GENBANK Accession No. NM_138712, dated Apr. 12, 2009.
GENBANK Accession No. NM_138992, dated Apr. 5, 2009.
GENBANK Accession No. NM_139317, dated Apr. 5, 2009.
GENBANK Accession No: S48568, dated Apr. 17, 2002.
GENBANK Accession No. U22431, dated Jun. 28, 1995.
GENBANK Accession No. U25676, dated Jul. 20, 1995.
GENBANK Accession No. X005881, dated Oct. 7, 2008.
GENBANK Accession No. X01394, dated Oct. 7, 2008.
GENBANK Accession No. X16302, dated Apr. 18, 2005.
GENBANK Accession No. XM_001831, dated May 8, 2002.
GENBANK Accession No. XM_003061, dated May 8, 2002.
GENBANK Accession No. XM_003751, dated Oct. 16, 2001.
GENBANK Accession No. XM_015547, dated Aug. 1, 2002.
GENBANK Accession No. XM_589987, dated Sep. 30, 2005.
Germain-Desprez et al., 2001, "The SMN genes are subject to transcriptional regulation during cellular differentiation", Gene, 279:109-117.
Gil et al., 1996, "Multiple regions of the *Arabidopsis* Saur-AC1 gene control transcript abundance: the 3' untranslated region functions as an mRNA instability determinant", EMBO, J 15:1678-1686.
Goodwin et al., 1993, "Translational regulation of tra-2 by its 3' untranslated region controls sexual identity in C. elegans", Cell, 75:329-339.
Goodwin et al., 1997, "A genetic pathway for regulation of tra-2 translation", Develop., 124:749-758.
Gramolini et al., 2001, "Distinct regions in the 3' untranslated region are responsible for targeting and stabilizing utrophin transcripts in skeletal muscle cells", J Cell Biol, 154:1173-1183.
Gramolini, 2001, "Increased expression of utrophin in a slow vs. a fast muscle involves posttranscriptional events", Am J Physiol Cell Physiol., 281(4):C1300-9.
Grens et al., 1990, "The 5'-and 3'-untranslated regions of ornithine decarboxylase mRNA affect the translational efficiency", J. Biol. Chem., 265:11810-11816.
Gubitz et al., 2004 "The SMN complex", Exp Cell Res.; 296:51-6.
Guhaniyogi & Brewer, 2001, "Regulation of mRNA stability in mammalian cells", Gene, 265(1-2):11-23.
Haag & Kimble, 2000, "Regulatory elements required for development of caenorhabditis elegans hermaphrodites are conserved in the tra-2 homologue of C. remanei, a male/female sister species", Genetics, 155(1):105-116.
Han et al. Interactive effects of the tumor necrosis factor promoter and 3'-untranslated regions. J Immunol. Mar. 15, 1991;146(6):1843-8.
Heaton et al., 1998, "Cyclic Nucleotide Regulation of Type-1 Plasminogen Activator-Inhibitor mRNA stability in Rat Hepatoma Cells", J Biol. Chem., 273:14261-14268.
Hoover et al., 1997, "Pim-1 protein expression is regulated by its 51-untranslated region and translation initiation factor eIF-4E", Cell Growth Differ., 8: 1371-1380.
Horvath et al., "Multiple elements in the 5' untranslated region downregulate c-sis messenger RNA translation", Cell Growth & Diff., 6: 1103-1110.
Huang et al., 1990, "Intervening sequences increase efficiency of RNA 3' processing and accumulation of cytoplasmic RNA", Nucl. Acids Res., 18(4):937-947.
Hubert et al., 1996, "RNAs mediating cotranslational insertion of selenocysteine in eukaryotic selenoproteins", Biochimie, 78(7):590-596.
Hudziak et al., 2000, "Antiproliferative effects of steric blocking phosphordiamidate morpholino antisense agents directed against c-myc." Antisense & Nucleic Acid Drug Development 10(3):163-176.
Huez et al., 1998, "Two Independent Internal Ribosome Entry Sites are Involved in Translation Initiation of Vascular Endothelial Growth Factor mRNA", Mol. Cell. Biol., 18(11):6178-6190.
Hyder et al., 2000, "Identification of functional estrogen response elements in the gene coding for the potent angiogenic factor vascular endothelial growth factor", Cancer Res., 60:3183-3190.
Iannaconne et al., 2002 "Outcome Measures for Pediatric Spinal Muscular Atrophy", Arch Neurol. 59:1445-1450.
Iannaconne et al., 2003, "Reliability of 4 Outcome Measures in Pediatric Spinal Muscular Atrophy", Arch Neurol; 60:1130-1136.
Iida et al., 2002, "Vascular endothelial growth factor gene expression in a retinal pigmented cell is up-regulated by glucose deprivation through 3' UTR", Life Sciences, 71:1607-1614.
Ismail et al., 2000, "Split-intron retroviral vectors: enhanced expression with improved safety", J. Virol., 74 (5):2365-2371.
Jan et al., 1997, "Conservation of the C.elegans tra-2 3'UTR translational control", Embo J., 16(20):6301-6313.
Jan et al., 1999, "The Star protein, GLD-1, is a translational regulator of sexual identity in Caenorhabditis elegans", EMBO J., 18:258-269.
Jarecki et al., 2005 "Diverse small-molecule modulators of SMN expression found by high-throughput compound screening: early leads towards a therapeutic for spinal muscular atrophy", Hum Mol Genet.; 14(14):2003-18.
Kakegawa et al., 2002, "Rapamycin induces binding activity to the terminal oligopyrimidine tract of ribosomal protein mRNA in rats", Arch Biochem Biophys., 402(1):77-83.
Kambadur et al., 1997, "Mutations in myostatin (GDF8) in double-muscled Belgian Blue and Piedmontese cattle", Genome Res., 7(9):910-6.
Karin et al., 2006, "Role for IKK2 in muscle: waste not, want not", J Clin Invest., 116: 2866-2868.
Kastelic et al., 1996, "Induction of rapid IL-1 beta mRNA degradation in THP-1 cells mediated through the AU-rich region in the 3'UTR by a radicicol analogue", Cytokine, 8: 751-761.
Kedersha et al., 2002, "Stress Granules: Sites of mRNA triage that Regulate mRNA Stability and Translatability", Biochem. Society Transactions, 30(6):963-969.
Keene & Tenenbaum, 2002, "Eukaryotic mRNPs may represent post-transcriptional operons" Mol. Cell., 9:1161-1167.
Kemeny et al., 1998, "The tetravalent guanylhydrazone CNI-1493 blocks the toxic effects of interleukin-2 without diminishing antitumor efficacy", Proc. Natl. Acad. Sci. USA, 95: 4561-4566.
Kim et al., 2002, "The human elongation factor 1 alpha (EF-1 alpha) first intron highly enhances expression of foreign genes from the murine cytomegalovirus promoter", J. Biotechnol., 93(2):183-187.
Klausner et al., 1993, "Regulating the Fate of mRNA: The control of Cellular Iron Metabolism", Cell, 72:19-28.
Kobayashi et al., 1998, "Characterization of the 3' Untranslated region of mouse DNA topoisomerase IIα mRNA", Gene, 215:329-337.
Koeller et al., 1991, "Translation and the stability of mRNAs encoding the transferrin receptor and c-fos", Proc. Natl. Acad. Sci., 88:7778-7782.
Kolb et al., 2006, "A novel cell immunoassay to measure survival of motor neurons protein in blood cells", BMC Neurology, 6:6.
Kowalski and Mager, 1998, "A human endogenous retrovirus suppresses translation of an associated fusion transcript, PLA2L", J. Virol., 72(7):6164-8.
Kozak et al., 1986, "Influences of mRNA secondary structure on initiation by eukaryotic ribosomes" Proc. Natl. Acad Sci., 83:2850-2854.
Krag et al., 2004, "Heregulin ameliorates the dystrophic phenotype in *mdx* mice", PNAS, 101: 13856-13860.

(56) References Cited

OTHER PUBLICATIONS

Lagnado et al., 1994, "AUUUA is Not sufficient to promote Poly(A) Shortening and Degradation of mRNA: the Functional Sequence within the AU-rich elements may be UUAUUUA(U/A)(U/A)", Mol. Cell. Biol., 14: 7984-7995.
Lai et al., 1999, "Evidence that Tristetraprolin binds to AU-Rich Elements and promotes the Deadenylation and Destabilitzation of Tumor Necrosis Factor Alpha mRNA", Mol. Cell. Biol., 19(6):4311-4323.
Lal et al., 2004, "Concurrent Versus Individual Binding of HuR and AUF1 to Common Labile Target mRNA's", EMBO J., 23:3092-3102.
Lemm et al., 2002, "Regulation of c-myc mRNA decay by translational pausing in a coding region instability determinant", Mol. Cell. Biol., 22(12):3959-3969.
Levy et al., 1995, "Sequence and functional characterization of the terminal exon of the human insulin receptor gene", Biochem Biophys Acta, 1263:253-257.
Levy et al., 1996, "Post-transcriptional Regulation of Vascular Endothelial Growth Factor by Hypoxia", J. Biol. Chem., 271:2746-2753.
Levy et al., 1998, "Hypoxic stabilization of vascular endothelial growth factor mRNA by the RNA-binding protein HuR", J Biol. Chem., 273(11):6417-6423.
Lewis et al., 1998, "Mapping of a Minimal AU-rich Sequence Required for Lipopolysaccharide-induce binding of a 55-kDA protein on tumor necrosis Factor-α mRNA", J Biol. Chem., 273:13781-13786.
Li et al., 2001, "Targeting HER-2/neu-overexpressing breast cancer cells by an antisense iron responsive element-directed gene expression", Cancer Letters, 174(2):151-58.
Lunn et al., 2004, "Indoprofen upregulates the survival motor neuron protein through a cyclooxygenase-independent mechanism", Chem Biol.; 11(11):1489-93.
McTiernan et al., 1999, "Characterization of proximal transcription regulatory elements in the rat phospholamban promoter," J. Molecular & Cellular Cardiology. 31(12): 2137-2153.
Mehta et al, 2006, "Derepression of the Her-2 uORF is mediated by a novel post-transcriptional control mechanism in cancer cells", Genes & Dev., 20:939-953.
Merlini et al., 2003, "Role of gabapentin in spinal muscular atrophy: results of a multicenter, randomized Italian study", J Child Neurol.; 18(8):537-41.
Millard et al., 2000, "A U-Rich Element in the 5' Untranslated Region if necessary for the Translation of p27 mRNA" Molec & Cell. Biol., 20(16):5947-5959.
Miller et al., 1998, "The Vascular Endothelial Growth Factor mRNA Contains an Internal Ribosome Entry Site", FEBS Letters, 434:417-420.
Monani et al., 1999, Promoter analysis of the human centromeric and telomeric survival motor neuron genes (SMNC and SMNT), Biochim Biophys Acta; 1445(3):330-6.
Morris et al., 2000, "Upstream Open Reading Frames as Regulators of mRNA translation," Molec & Cell. Biol., 20(23):8635-8642.
Muhlrad et al., 1995, "Turnover mechanisms of the stable yeast PGK1 mRNA", Mol. Cell. Biol., 15(4):2145-2156.
Mukherjee et al., 2002, "The mammalian exosome mediates the efficient degradation of mRNAs that contain AU-rich elements", Embo J., 21:165-174.
Nanbru et al., 1995, "Alternative translation of the proto-oncogene c-myc by an internal ribosome entry site", J. Biol. Chem., 272:32061-32066.
Nanbu et al., 1994, "Multiple Instability-Regulating Sites in the 3'Untranslated Region of the Urokinase-Type Plasminogen activator mRNA", Mol. Cell. Biol., 14:4920-4928.
Nishimori et al., 2004, "Involvement of the 3'-untranslated region of cyclooxygenase-2 gene in its post-transcriptional regulation through the glucocorticoid receptor", Life Sciences, 74:2505-2513.

Nowak and Davies, 2004, "Duchenne Muscular Dystrophy and dystrophin: pathogenesis and opportunities for treatment", EMBO Reports, 5:872-876.
Nunokawa et al. Expression of human inducible nitric oxide synthase is regulated by both promoter and 3'-regions. Biochem Biophys Res Commun. Apr. 17, 1997;233(2):523-6.
Oh et al., 1992, "Homeotic gene Antennapedia mRNA contains 5'-noncoding sequences that confer translational initiation by internal ribosome binding", Genes Dev., 6:1643-1653.
Ohlendieck and Campbell, 1991, "Dystrophin-associated proteins are greatly reduced in skeletal muscle from mdx mice", J Cell Biol, 115:1685-1694.
Ostareck-Lederer et al., 2002, "c-Src-mediated phosphorylation of hnRNP K drives translational activation of specifically silenced mRNAs", Mol. Cell. Biol., 22(13):4535-4543.
Patel et al, 2005, "Molecular mechanisms involving IGF-1 and myostatin to induce muscle hypertrophy as a therapeutic strategy for Duchenne Muscular Dystrophy", Acta Myol., 24(3):230-41.
Paushkin et al., 2002 "The SMN complex, an assemblyosome of ribonucleoproteins" Curr Opin Cell Biol., 14:305-12.
Paynton & Bachvarova, 1994, "Polyadenylation and deadenylation of maternal mRNAs during oocyte growth and maturation in the mouse", Mol. Reprod. Dev., 37(2): 172-180.
Pelletier & Soneberg, 1988, "Internal initiation of translation of eukaryotic mRNA directed by a sequence derived from poliovirus RNA", Nature, 334:320-325.
Pesole et al., 2001, "Structural and Functional Features of Eukaryotic mRNA Untranslated Regions", Gene, 276:73-81.
Peterlin et al., 1993, "Tat Trans-Activator." In Human Retroviruses; Cullen Ed.; Oxford University Press: New York, pp. 75-100.
Piecyk et al., 2000, "TIA-1 is a translational silencer that selectively regulates the expression of TNF-alpha" Embo J., 19:4154-4163.
Pontrelli et al., 2004, "Translational control of apolipoprotein B mRNA: regulation via cis elements in the 5' and 3' untranslated regions", Biochemistry, 43(21):6734-44.
Project Catalyst Poster—"Identification and characterization of small molecules for the treatment of duchenne muscular dystrophy," previously presented at the Muscular Dystrophy Coordinating Committee on Jun. 25, 2007 in Washington, D.C.
Project Catalyst Poster Abstract—"Identification and characterization of small molecules for the treatment of duchenne muscular dystrophy," previously presented at the Muscular Dystrophy Coordinating Committee on Jun. 25, 2007 in Washington, D.C.
PTC Therapeutics Poster—"Identification and characterization of small molecules for the treatment of duchenne muscular dystrophy," previously presented at the 11th Annual Meeting of the RNA Society on Jun. 20, 2006 in Seattle, Washington.
Qin & Pyle, 1999, "Site-specific labeling of RNA with fluorophores and other structural probes", Methods, 18 (1):60-70.
Rajagopalan & Malter, 2000, "Growth factor-mediated stabilization of amyloid precursor protein mRNA is mediated by a conserved 29-nucleotide sequence in the 3'-untranslated region." J. Neurochem., 74(1):52-59.
Rapella et al., 2002, "Flavopiridol inhibits vascular endothelial growth factor production induced by hypoxia or picolinic acid in human neuroblastoma", Int. J. Cancer, 99:658-664.
Raught et al., 2000, "Regulation of ribosomal recruitment in eukaryotes" in: "Translational Control of Gene Expression", Sonenberg, Hershey and Mathews, eds. Cold Spring Harbor Laboratory Press, Ch. 6. pp. 245-293.
Reinmann et al., 2002, "Suppression of 15-lipoxygenase synthesis by hnRNP E1 is dependent on repetitive nature of LOX mRNA 3'-UTR control element DICE", J. Mol. Biol., 315(5):965-974.
Rogers et al., 2002, "An iron-responsive element type II in the 5'-untranslated region of the Alzheimer's amyloid precursor protein transcript", J. Biol. Chem., 277(47):45518-45528.
Sachs & Geballe, 2006, "Downstream control of upstream open reading frames", Genes & Dev., 20:915-921.
Sachs et al., 1993, "Messenger RNA Degradation in Eukaryotes", Cell, 74:413-421.
Sambrook et al., 1989, "Standard protocol for calcium phosphate-mediated transfection of adherent cells." Molec. Cloning, 16:3316-37.

(56) References Cited

OTHER PUBLICATIONS

Savant-Bhonsale et al., 1992, "Evidence for instability of mRNAs containing AUUUA motifs mediated through translation-dependent assembly of a > 20S degradation complex", Genes Dev., 6:1927-1939.
Schlatter & Fussenegger, 2003, "Novel CNBP- and La-based translation control systems for mammalian cells." Biotechnol Bioeng., 81(1):1-12.
Shaw & Kamen, 1986, "A conserved AU sequence from the 3' Untranslated Region of GM-CSF mRNA mediates selective mRNA degradation", Cell, 46:659-667.
Shyu et al., 1991, "Two distinct destabilizing elements in the c-fos message trigger deadenylation as a first step in rapid mRNA decay", Genes Dev., 5:221-231.
Stebbins-Boaz et al., 1996, "CPEB controls the cytoplasmic polyadenylation of cyclin, Cdk2 and c-mos mRNAs and is necessary for oocyte maturation in Xenopus", Embo J., 15(10):2582-2592.
Stein et al., 1998, "Translation of vascular endothelial growth factor mRNA by internal ribosome entry: implications for translation under hypoxia", Mol. Cell. Biol., 18:3112-3119.
Stoecklin et al., 1994, "Functional Hierarchy of AUUUA Motifs in Mediating Rapid Interleukin-3 mRNA decay", J Biol. Chem., 269:28591-28597.
Stoecklin et al., 2003, "A constitutitive Decay Element Promotes Tumor Necrosis Factor Alpha mRNA Degradation via an AU-Rich Element-Independent Pathway." Molec & Cell. Biol., 23(10):3506-3515.
Stolle et al., 1988, "Cellular Factor affecting the stability of β-globin mRNA." Gene, 62:65-74.
Stoneley, 1998, "C-Myc 5' untranslated region contains an internal ribosome entry segment", Oncogene, 16:423-428.
Sumner, 2006, "Therapeutics development for spinal muscular atrophy", NeuroRx.; 3(2):235-45.
Sumner et al., 2006, "SMN mRNA and protein levels in peripheral blood: biomarkers for SMA clinical trials", Neurology, 66:1067-1073.
Sullivan et al., 1996, "Mutational analysis of the DST element in tobacco cells and transgenic plants: Identification of residues critical for mRNA instability", RNA, 2:308-315.
Tay et al., 2000, "The control of cyclin B1 mRNA translation during mouse oocyte maturation", Dev. Biol., 221(1):1-9.
Thiele et al., 1999, "Expression of leukocyte-type 12-lipoxygenase and reticulocyte-type 15-lipoxygenase in rabbits", Adv Exp Med Biol., 447:45-61.
Tholanikunnel & Malbon, 1997, "A 20-nucleotide (A + U)-rich element of beta2-adrenergic receptor (beta2AR) mRNA mediates binding to beta2AR-binding protein and is obligate for agonist-induced destabilization of receptor mRNA", J. Biol. Chem., 272:11471-11478.
Thompson et al., 2000, "Rapid deadenylation and Poly(A)-dependent translational repression mediated by the Caenorhabditis elegans tra-2 3' untranslated region in Xenopus embryos", Mol. Cell. Biol., 20(6):2129-2137.
Tischer et al., 1991, "The human gene for vascular endothelial growth factor", J. Biol. Chem., 266(18):11947-11954.
Tobin et al., 2005, "Myostatin, a negative regulator of muscle mass: implications for muscle degenerative diseases", Curr Opin Pharmacol., 5(3):328-32.
Trifillis et al., 1999, "Finding the right RNA: identification of cellular mRNA substrates for RNA-binding proteins", RNA, 5:1071-1082.
Trotta et al., 2003, "BCR/ABL activates mdm2 mRNA translation via the La antigen", Cancer Cell, 3(2):145-60.
Vachon et al.,1997, "Integrins (alpha7beta1) in muscle function and survival. Disrupted expression in merosin-deficient congenital muscular dystrophy", J Clin Invest., 100(7):1870-81.
Vagner et al., 1995, "Alternative translation of human fibroblast growth factor 2 mRNA occurs by internal entry of ribosomes", Mol. Cell. Biol., 15:35-44.
Vagner et al., 2001, "Irresistible IRES. Attracting the translation machinery to internal ribosome entry sites", EMBO Reports, 2:893-898.
Veyrune et al., 1996, "A localisation signal in the 3' untranslated region of c-myc mRNA targets c-myc mRNA and beta-globin reporter sequences to the perinuclear cytoplasm and cytoskeletal-bound polysomes", J Cell Sci, 109:1185-1194.
Wan, 2005, "The survival of motor neurons protein determines the capacity for snRNP assembly: biochemical deficiency in spinal muscular atrophy", Molec & Cell Biol, 25(13): 5543-5551.
Wang, et al., 2003, "Human SP-A 3'-UTR variants mediate differential gene expression in basal levels and in response to dexamethasone." Am J Physio, Lung Cell & Mol. Physio., 284(5):L738-L748.
Wells et al., 1998, "Circularization of mRNA by eukaryotic translation initiation factors." Mol. Cell., 2:135-140.
Westmark & Malter, 2001, "Extracellular-regulated kinase controls beta-amyloid precursor protein mRNA decay", Mol. Brain. Res., 90(2):193-201.
Wickstrom E. Oligonucleotide treatment of ras-induced tumors in nude mice. Mol Biotechnol. May 2001;18(1):35-55.
Wiklund et al., 2002, "Inhibition of translation by UAUUUAU and UAUUUUUAU motifs of the AU-rich RNA instability element in the HPV-1 late 3' untranslated region", J. Biol. Chem., 277:40462-40471.
Winstall et al., 1995, "Rapid mRNA Degradation Mediated by the c-fos 3' AU-Rich element and that mediated by the Granulocyte-Macrophage Colony-Stimulating Factor 4' AU-Rich Element occur through similar Polysome-Associated Mechanisms", Mol. Cell. Biol., 15:3796-3804.
Wolstencroft et al., 2005, "A non-sequence-specific requirement for SMN protein activity: the role of aminoglycosides in inducing elevated SMN protein levels", Hum Mol Genet, 14(9):1199-1210.
Worthington et al., 2002, "RNA binding properties of the AU-rich element-binding recombinant Nup475/TIS11/tristetraprolin protein", J. Biol. Chem., 277: 48558-48564.
Xu et al., 1997, "Modulation of the Fate of Cytoplasmic mRNA by AU-Rich elements: Key Sequence Features Controlling mRNA Deadenylation and Decay", Mol. Cell. Biol., 17:4611-4621.
Yamazaki et al., 2003, "HIF-1-dependent VEGF reporter gene assay by a stable transformant of CHO cells", Biol & Pharm Bull., 26(4): 417-420.
Ye et al., 1997, "Ultrabithorax and Antennapedia 5' untranslated regions promote developmentally regulated internal translation initiation", Mol. Cell. Biol., 17:1714-1721.
Yong et al., 2004, "Why do cells need an assembly machine for RNA-protein complexes?" Trends Cell Biol.; 15(5):226-32.
Zaldi & Malter, 1995, "Nucleolin and heterogeneous nuclear ribonucleoprotein C proteins specifically interact with the 3'-untranslated region of amyloid protein precursor mRNA", J. Biol. Chem., 271(29):17292-17298.
Zhang et al., 1995, "Identification and Characterization of a Sequence motif involved in nonsense-mediated mRNA decay", Mol. Cell. Biol., 15:2231-2244.
Zhang et al., 1996, "An enhanced green fluorescent protein allows sensitive detection of gene transfer in mammalian cells", BBRC, 227:707-11.
Zhang et al., 2000, "Wild-type p53 suppresses angiogenesis in human leiomyosarcoma and synovial sarcoma by transcriptional suppression of vascular endothelial growth factor expression", Cancer Res., 60:3655-3661.
Zhang et al., 2001, "An in vivo reporter system for measuring increased inclusion of exon 7 in SMN2 mRNA: potential therapy of SMA", Gene Ther., (20):1532-1538.
Zhu et al., 2001, "Binding of the La autoantigen to the 5' untranslated region of a chimeric human translation elongation factor 1A reporter mRNA inhibits translation in vitro", Biochim. Biophys Acta, 1521(1-3):19-29.
Zubiaga et al., 1995, "The nonamer UUAUUUAUU is the key AU-rich sequence motif that mediates mRNA degradation", Mol. Cell. Biol., 15(4):2219-30.
Zwicky et al., 2003, "Exploring the Role of 5' Alternative Splicing and of the 3'-Untranslated region of Cathepsin B MRNA" Biological Chemistry 384(7): 1007-1018.

* cited by examiner

Human IGF1 5' UTR

TCACTGTCACTGCTAAATTCAGAGGCAGATTAGAGCCTGCGCAATGGAATAAAGTCCTCAAAATTGAAATGTGACATTGCTCTCAACATCTCCCATCTCTCTGG
ATTTCCTTTTGCTTCATTATTCCTGCTAACCAATTCATTTTGTACTTCAGAAGCA

Fig. 1A

Human IGF1 3' UTR

GAAGACCCCTCCTGAGGAGTGAAGAGTGACATGCCACCGCAGGATCCTTTGCTCTGCACGAGTTACCTGTTAAACTTTGGAACACCTACCAAAAATAAGTTT
GATAACATTTAAAGATGGGCGTTTCCCCCAATGAAATACACAAGTAAACATTGTCTTTAGGAGTGATTTGCACCTTGCAAAATGGTCCTGGAGT
TGGTAGATTGCTGTTGATCTTTATCAATAATGTTCTATAGAAAAAAAGAAAAAATATATATAATATCTTAGTCCCTGCCTCTCAAGAGCCACAAATGCAT
GGGTGTGTATAGATCCAGTTGCACTAAATTCCTCTCTGAATCTTGGCTGCTGGAGCCATTCATTCAGCAACCTTGTCTAAGTGGTTATGAATTGTTCCTTA
TTTGCACTCTCTTTCTACACAACTCGGGCTGTTGTTTACAGTGTCTGATAATCTTGTAGTCTATACCCAAGATTCCATCTGTGGCATTTGTACCAAATATAAGTTGGATGCATTT
TGGCCTCCTCAAAAGCAGCAGCAAGTCGTCAAGAAGCACACCAATTCTAACCCACAAGAATAATGCAAATTGTGCAACTTGTGGGCCAATCATCATTTTGAGGCCAATCATTTTTATTTTTCCATATAGAGCACTATGTAA
TATTTAGACACAAGCTTATTTTCAACTCAAAAGAGTTCCTTCAAATGATGAGTTAATGTGCAACTAATTAGTAACTTCCTCTTTATTTTTGTTATATGAAAGAGTCTGGCCAAA
TAGAAAGTTTCTTCAACTCAAAAGAGTTCCTTCAAATGATGAGTTAATGTGCAACTAATTAGTAACTTCCTCTTTATTTTTGTTATATGAAAGAGTCTGGCCAAA
ATTAGCATATCAATTATACAGGATATATCAAACAGTATGTAAAACTCTGTTTTTAGTATAATGGTACTGAAAACACCATCCATTTGGGAAGAAGGCAAA
ACGGTAATACGTGAAAGCAAAACAATAGGGGAAGCCTGGAGACACAAAGTTCAGACACAACTTCAGACAGGAACTTCAGACAGAGGAAACTGTGAATGGAAAAG
GTCCCCCAGTTATGCCTTCAAGAGGAACTTCAGACACAACTTCAGACAGGAACTTCAGACAGAGGAAACTGTGAATGGAAAAG
CAGAAGGCTAGGAATTTAGCAGTCCTGGTTCTTTCCTATCTGCAAATGGGCAATATCTGCCAGTCCAATATGTCATCCAAAGGGTGTATAAGGTTAAAGATAAAGATT
TCACTTCACCTCTGCCTCAGTTCCTGTCTGAAGGTGCACATCAGGGCGCTTCAGACGATGTTGAGATGCAAGAAGAATTCTATAAATAACCCATTCATAGACATGCTAGA
CAGATTTTTACCCTGGGTTGATGCTCCTGACATCTCAGTGTTCAATTTGATTTCAATTTGGTTTTATGAAACTGTAACAGCTCAATCTCTTAAAC
GATTGGTGAATTGAATGTGGGAAGAGAGATTTCAAATATGTGGGAAGAGAGATTTCAAATATGTGGGAAGAGAGATTTCAAATATGTAACAAGATAAGTGAATACAAAGATAAGTAAGCAGTTACTACATATCTAGTAAAACCT
AAGGAGAAAAACAAAGAGATTTAATAATTCTATTCATTTTGAAAAACACAATTTACTCTCTTATTCCTGCTCATAGCCTAGAAGTAGCCCTATCTGCAGATCAAGATTTTCTCATTAGAACAATGAATTAT
TGTTTAATACTATAAAAGTCACAAAGTTCCATCACTGGTTAGTTGCCACTGGTTAGTCCACTGGTTAGTCCACTGGTTAGTCCACTGGTAACTTTTGGTTAAAGGTAACTTTTGGTAATGCTTGACTAGAGTT
ATCTAATAATAAAAAGTCACAAAGTTCCATCACTGGTTAGTTGCCACTGGTTAGTCCACTGGTTAGTCCACTGGTTAGTCCACTGGTAACTTTTGGTAATGCTTGACTAGAGTT
TCAGTTGAAAGGCTATCCAAGAAAGTCCACTGGTTAGTTGCCACTGGTTAGTCCACTGGTTAGTCCACTGGTTAGTCCACTGGTAACTTTTGGTAATGCTTGACTAGAGTT
AAATTGGTATCAGATCTTTCAGATCTTTCAGATCTTTCAGATCTTTCAGATCTTTCAGATCTTTCAGATCTTTCAGATCTTTCAGATCTTTCAGATCTTTCAGATCTTTCAGATCTTTCAGATCTTTCAGATCTTTCAGATCTTT
CCAGCATTCAGATCTTCAGTTTTTCTCCCACTGGGTCACCTCAGTCAAACAAGTATTTTAACCTCTGCCTGTTTCCAGACATACAGGTTCTGTGGAATAAGATACTGGACTC
GAAAACACAAAATAACATCTTCAGTTTTTCTCCCACTGGGTCACCTCAGTCAAACAAGTATTTTAACCTCTGCCTGTTTCCAGACATACAGGTTCTGTGGAATAAGATACTGGACTC
AAAAGAAGGCCCCATTTAGTGGAGCCAGCAATCCTGTTCAGTGAACATCTTTTCAGTCAACATCTTTTCAGTCAACATCTTTTCAGTCAACATCTTTTCAGTCAAGCATCATAGCAAGCATCAAGCATCAAGCATCAAGCATCAAGCATCAAGCATCAAGCATCAAGCATCAAGCATCAAGCATCAAGCATCAAGC
AATGTTCTAATCACTATGGACAGTGTAAAAGAACTATACATCATTTGCCCTGCCTGTTTAAAATTATTCCCTGTACCTTATAGCAGTCTTCTGCAGACTTAAC
CTCTTCCCAAGATGGCACTCTTTTATTCTTGTCCCAGTGTCTATGACTTCTAAGAGTGTCTATGATGAATTCTAAGAGTGTCATGCCCCAAGAAGCCTTATAGGAGCAGTCTTCTGCAGACTTAAC
ATGTTTTTCATGATTAGATGTGATAATTCAACTTTTCCAACACATATCCTCCAACTGCAGTTGATTACTATATAACCTATATAAATAACCTATTCTATCAGAATAACTACCAATTCACATTT
AAGATGAACTGCAGATTAAAACAAAGATGTGACAAATTTAGATTAGATTAAACCCTGGAAGTGCTTCAGAATTGCTTTATAAATTCTTGAATGAGGCAATTTCAAGATATTTGTAAAAGAACAGTAAA
AACCAAAAATTAAAACTAGAAAACAATTTACAAGCTTTGCTTCACAAACAAATTGATGCAAACCTTACAAGCTTTGCTTCAGAATTAGATAGTGCTTTATAAATTCTTGAATGAGGCAATTTCAAGATATTTGTAAAAGAACAGTAAA
CATTGGTAAGAATGAGCTTTCAACTGGAGAAGATGGGGATAAATAGTAGAAATAATAGAAATAATAGAAATAATAGAAATAATAGAAATAATAATAAAAGGAACAGTAAAGCAACATAATAAAAATAATTAAAA
GTATTATTTGAACTTTTAAGATGAGCTCTCCACTCTTCCCTGAAAAATCTCTTAACACCCA

Fig. 1B

```
CCCTACAATACACAGAGACACACACACACACACACACATTCACCCTAAGGATCCAATGGAATACTGAAAAGAAATCACTTCCTTGA
AATTTTATTAAAAACAACAACAAACAAACAAAGCCTGTCCACCCTTGAGAATCCTTCCTCTCCTTGGAAGTCAATGTTTGTGTAGATGAAACCATCTCATG
CTCTGTGGCTCCAGGGTTTCTGTATTGTTCTTAAGAGATACTTATGCAGTCTAGATAAAGATTAGCACATTTGCTTCCCATTTATTGTTGGCCAGCTA
TGCCAATGTGGTGCTATTGTTCTTAAGAAATATAGCACTTAGGTCTATCTAGCACCACCACCTTCAACTTTTATCACTCACAAGTAGTGTACTGTTCACCAAATT
ACAATTCTATAGATAGATGGCTTAATAAAATAGCATTAGGTCAGGGGCAGGAGTGCCAGGAGCATTTGCTCTCAACTTTGTTTGGCTCTCAACTTAGCAAATTAGCAAATATATCC
GTGAATTTGGGGGTGCAGGGGCAGGAGTCATGAAGAGCATGAGAGAGAATCTTAGAGGTTAGAAGGCAAATAGAAGAATTTAAAAGATAAGTAAGTTCCTTATTGATTTTT
AATCTTCTGAACTTGATCAGCTGCTCTAAAACAGATATTCAGCAAGTGGAGAAATAAGCGGGAAAAATAAGAGAACAAAGAGAAAATACATAGATTTACCTGCAAAAATAGCTTCTGCCAAATCCCCC
TTGGGTATTCTTTGGCATTTGGTTTATGAGATGGGGGTATCTCCCTTCACCCAGTAGTCTCCAAAGAGCAGTAGCTTCATGAAAAGAGCAATCACTGATCTCATT
GGGAAATGTTGGAAAGTATTTCCTTATGAAAATTTTACTTTATACACAGTCTTAAAACTATAGCAGAACCTGTTGGTCTGTAATGACTTGGTTGAGCTATATCAGACTATTTAAATGTTT
TGCTATTTTAATCTAAAAGATTGTGCTAATTATTAGAGCAGCATCATTTATTTAAAACAGAAGAATCTTCCATTCAATCACATGGCTTCCACC
AATATTTTCAAAAGATAAATCTGATTTTATGCAATGGCAAACAAAGGGAAAATGTTGTTTGGATTTCTGGTTTGATTCTGGTTCGGTGTGCCCCCTGCAAAGACCATAAAGTCCA
GATCTGGTAGGGGCAACAACAAAGGAAATGTGGTTAGGTATTAGAAGTGATACATTCCTATCTGGAACAATGCTTTTGTGTAATTCTATTTAAAAAGAGAGAAGACTGTCA
TATTGCTATTTTAATATTTATAAGACCTTCCTGTAGGTATGCATATGGTACAGGATAAAGATATCAATTTAAATAACCATTCCTATCTGGAACAATGCTTTTGTGTAATTCTATTTAAAAAGAGAGAAGACCTCTCACAGATAAGA
GAAGCTTTAAGTGCATATGGTACAGGATAAAGATATCAATTTAAATAACCATTCCTATCTGGAACAATGCTTTTGTGTAATTCTATTTAAAAGAACCTCTCACAGATAAGA
CAGAGGCCCAGGGGATTTTGAAGCTGTCTTATTCTGCCCCCATCCCAACCCAGCCTTCCCTCTCTTTTTTCCTTTTGTGAGATGGGGTCTCGCACTGTCCCCCA
AGTCGAAACTCTAGAATTAAAGGAACCTCACTGTGTTCCACGTGTTCCCCTGAAAACATATTTCAGCGCATTCTCCTGCCTCAGCCTCAGGGATTACAGGC
GGCTGAGTGCAGTGGCATGATCTCGGCTCACTGCAACCTCCACCCTCGGGCCATCTCCCTGCCTCAGGCAGGTTGGGACTCAAACATCCTGACCTTGTGATTGCCCGC
ACCCACCACTATCCCCGCTAATTTTTGGATTTTTAATAGAGACGGGGTTTACCATGTTGGCCAGGCTGGTCTCAAACTCCTGACCTCAAGTGATGATCCACCCGGCC
CTCAGCCTCCCAAATTGCTGGGATTACAGGCATGAGCCACCACGCCTGGCCCATGTGTTCCCTCTTAAGTAAAAAAAGAGAGGACACAAAACCAAATGTTA
CTGCTCAACTGAATTGAGGCTAAGATGAGTTAAGATGGAACAGAGTTTCTCCTAAATAACATTACTCATTTATTTGCCCAAATGCGAGCTGAATTACCTCACTTTCAAAACATGACCTTCCACAATCCTTAGA
ATCCCTTTCAGCACCCATTGACCCCATGCTGAAACCTAAAAGTAAACATTACCACACTCATAGCAAAGCACTTCATTTGGATATTATCTTGTACCCGCT
GCTAAACACTGCGAGGAGGACTTTATATCAGTTCAGTTACATAAAGGCCCCAATACACATGTGTCAGATCTTTATCTGTCGTCGTATCAGAAAGTCTATTCAAAATATCAAACCT
TCAAATATCAGCAGCTTATATTCAGTTACATAAAGGCCCCAATACACATGTGTCAGATCTTTATCTGTCGTCGTATCAGAAAGTCTATTCAAAATATCAAACCT
ATGCTGGCCATTCGTCTTACATCTGTCTTAGTTGAAAAGCATATTTTTTATTAAATTAATTCTGATTGTATTTGAAAATATAATTATTATTCAATTCACATGTTGAACACAGAAAA
ATGACTGCCCGCAAATATTTTAAAATCTGAAAAGCATATTTTTTATTAAATTAATTCTGATTGTATTTGAAAATATAATTATTATTCAATTCACATGTGCAGAGGAA
TATCAATCCTAATGACTTCTAAAATGTAACTAATTGAATCATTATCTTACATTTACTGTTTAATAAGCATATTTTAATAAGCATATTTTTAATAAGCATATTTTTAATAAGCATATTTTGAAAATGTATGCCTAGAGTGTCATAATAAAA
TGGTATATCTTTCTTTAGTAATTACAAAAAAAAAAAAAAA
```

Fig. 1C

Human α7 integrin 5' UTR

GGAGCGGGCGGGGGGGGCGGGGAGGGCTGGCGGGCGGCGAACGCTGGGAGACGTCTGAAAGACCAACGAGACTTTGGAGACCAGAGAC
GCGCCTGGGGGACCTGGGCGCTTGGGGCGCGTGCGAGATTTCCCTTGCATTCGCTGGGAGCTCGCGCAGGGATCGGTCCC

Fig. 2A

Human α7 integrin 3' UTR

GTTCCCATGTCCCAGCCTGCCTGCCCTGTGGCTGCTGCCCTCCATCCCTTCCCCAGAGATGGCTCCTTGGGATGAAGAGGGTAGAGTGGGCTGCTGGTGTCG
CATCAAGATTTGGCAGGATCGGCTTCCTCAGGGCACAGACCTCTCCACCACAAGAACTCCTCCCACCAACTTCCCCTTAGAGTGCTGTGAGA
TGAGAGTGGGTAAATCAGGGACAGGCCATGGGGCCCTGAGAGGGCCAGGGTGTCCTGAAGGTCAAAGGTGGGAGAAGGGATCCTAATCCCT
TCCTCTCCCATTCACCCTGTGTAACAGGACCCAAGGACCCCCGGAAGTGCCTAACCTAGAGGTCGGGGAGGAGGTTGTGTCACTGAC
TCAGGCTGCTCCTTCCTCTAGTTTCCCCTCCATCTGACCTCATCAGTCTAGTGGTTTCGTGGTTCGTCTATTTATTAAAAATATTG
AGAACAAAAAAAAAAAAAAAAAA

Fig. 2B

Utrophin 5' UTR ttgtggagtcgttttcctcgagcaggggaggaagcgggcagcagccggccgccgggcttctcccgccgaggggcgaggaggagcctctggctccagaagccgattgggaatcacggggagcggccgccccttct
tttggtcatttctgcaaacggaaaactctgagcgttggcaaagttggtcctgcgcgcgccccttccaggtttgactgtttgttttgcgaactaccaggcaggaagattgcacaagtaagggcgtttcagtcg
ggtgtcaatttctcttttcttttttaaaatttcgttcgtgctctccaagcttatttttttaaaatacatcgcaccaccaccaccacactcgcacacaccccccggttactccgtgtcaaactcctagaggagcct
tggccagctcggggtgcgcggtgcgaccggcaggcgaggcgaggcccccgcgggcagcag

Fig. 3A

Utrophin 3' UTR gtgaagtattcatccggccaaccaatgtttcctgacgtacagtgttgcccttttcagcaaatgccaattccaagttccATTAAAtcagaagctccatgctccttgcccacgatgttgagtgctgactgtgtgttcactgaa
agagtaaacactgactatccaaagagaaatggatattttgttttataaccatatattatgttttctctcctttcatgcaagtgtaaattaatgaacagagaggtatttgaaatgtaataacattgtcacggatttgtat
aatgtatacagcattgggaaagtggtggggctttcaataccgtctttttaataactgataccgtcttttaataactgacaaagcttacattccttcgtgttcatattaaccttgcacaattacttc
atttttctgactctttaccacacatgttttggttatttataaatttatcagccatagtaccaactagatccatgtatttgttccgtgatttggccacatAATAAAttcataaatcatccaaa
tatcttatatacacacatgtttaagctacagccctgttatgccgttaacttatttgacgttgccacttgactacctgataaccgtAATAAAaatcctaagcctaaatggcatttctttgggatatttt
tcctgcattttattccctttttatataagtaggaattaattatttatttgcttaatctatttgataaagaagactacATTATaataatctcaaagatcatattac

METHODS OF SCREENING FOR COMPOUNDS FOR TREATING MUSCULAR DYSTROPHY USING HUMAN ALPHA7 INTEGRIN MRNA TRANSLATION REGULATION

This application is a divisional of U.S. application Ser. No. 13/646,943 filed Oct. 8, 2012, now U.S. Pat. No. 8,741,572, which is a divisional of U.S. application Ser. No. 12/143,705 filed Jun. 20, 2008, now U.S. Pat. No. 8,283,115, which claims the benefit of U.S. Provisional Application No. 60/936,632, filed Jun. 20, 2007. U.S. application Ser. No. 13/646,943 filed Oct. 8, 2012 and U.S. application Ser. No. 12/143,705 filed Jun. 20, 2008 are both incorporated herein in their entireties.

FIELD OF THE INVENTION

The present invention relates to assays for screening for compounds useful for treating muscular dystrophy and methods for treating this degenerative muscle disease.

BACKGROUND OF THE INVENTION

Muscular dystrophy (MD) or a form thereof, refers to a group of genetic, hereditary muscle diseases that cause progressive muscle weakness (Harrison's Principles of Internal Medicine, 16th Edition, New York: McGraw-Hill, 2005, 17th edition). Muscular dystrophies are characterized by progressive skeletal muscle weakness, defects in muscle proteins, the death of muscle cells and tissue (Emery A E, *Lancet*, 2002, 359(9307): 687-695), resulting in the progressive weakness and degeneration of skeletal muscles leading to loss of ambulation, difficulties in breathing and eating, and premature death. Although there are more than 100 diseases in total with similarities to muscular dystrophy, there are nine diseases, including Duchenne Muscular Dystrophy (DMD) (also known as Pseudohypertrophic), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert Disease), Oculopharyngeal Muscular Dystrophy (OPMD), Distal Muscular Dystrophy (DD) (also known as Miyoshi) and Congenital Muscular Dystrophy (CMD) that are always classified as a muscular dystrophy (May 2006 report to Congress on Implementation of the MD CARE Act, as submitted by Department of Health and Human Service's National Institutes of Health).

Most types of MD are multi-system disorders with manifestations in body systems including the heart, gastrointestinal and nervous systems, endocrine glands, skin, eyes and other organs (May 2006 report to Congress on Implementation of the MD CARE Act, as submitted by Department of Health and Human Service's National Institutes of Health). Multi-system disorders related to MD include motor neuron diseases such as, but not limited to, Amyotrophic Lateral Sclerosis (ALS) (also known as Lou Gehrig's Disease), Spinal Muscular Atrophy Type 1 (SMA1, also known as Werdnig-Hoffmann Disease), Spinal Muscular Atrophy Type 2 (SMA2), Spinal Muscular Atrophy Type 3 (SMA3, also known as Kugelberg-Welander Disease) and Spinal Bulbar Muscular Atrophy (SBMA) (also known as Kennedy Disease and X-Linked SBMA); metabolic muscle diseases such as, but not limited to, Phosphorylase Deficiency (MPD or PYGM) (also known as McArdle Disease), Acid Maltase Deficiency (AMD) (also known as Pompe Disease), Phosphofructokinase Deficiency (also known as Tarui Disease), Debrancher Enzyme Deficiency (DBD) (also known as Cori or Forbes Disease), Mitochondrial Myopathy (MITO), Carnitine Deficiency (CD), Carnitine Palmityl Transferase Deficiency (CPT), Phosphoglycerate Kinase Deficiency, Phosphoglycerate Mutase Deficiency, Lactate Dehydrogenase Deficiency and Myoadenylate Deaminase Deficiency; peripheral nerve diseases such as, but not limited to, Charcot-Marie-Tooth Disease (CMT) (also known as Hereditary Motor and Sensory Neuropathy (HMSN) or Peroneal Muscular Atrophy (PMA)), Friedreich's Ataxia (FA) and Dejerine-Sottas Disease (DS) (chromosome 19 recessive form can be called CMT4F); inflammatory myopathies such as, but not limited to, Dermatomyositis (DM), Polymyositis (PM) and Inclusion Body Myositis (IBM); diseases of the neuromuscular junction such as, but not limited to, Myasthenia Gravis (MG), Lambert-Eaton Syndrome (LES) and Congenital Myasthenic Syndrome (CMS); myopathies due to endocrine abnormalities such as, but not limited to, Hyperthyroid Myopathy (HYPTM) and Hypothyroid Myopathy (HYPOTM); and other myopathies such as, but not limited to, Myotonia Congenita (MC) (two forms: Thomsen and Becker Disease), Paramyotonia Congenita (PC), Central Core Disease (CCD), Nemaline Myopathy (NM), Myotubular Myopathy/Centronuclear Myopathy (MTM or CNM) and Periodic Paralysis (PP) (two forms: Hypokalemic and Hyperkalemic) (see, Muscular Dystrophy Association website: mda.org/disease).

Genetically, MD or a form thereof, can be inherited in a dominant or recessive manner, or in some cases, caused by sporadic de novo mutations. Inherited forms of MD or a form thereof, involve genetic mutations of genes encoding, e.g., dystrophin, emerin, myotilin, lamin A/C, caveolin 3, calpain 3, dysferlin, dysferlin, γ-sarcoglycan, α-sarcoglycan, β-sarcoglycan, δ-sarcoglycan, telethonin, fukutin, fukutin-related protein, titin, E3-ubiquitin ligase, selenoprotein N1, collagen VI subunit $\alpha_2$, $\alpha_2$-Laminin, O-Mannosyltransferase, and O-MNAGAT.

Duchenne Muscular Dystrophy ("DMD"), a form of MD, is an X-chromosome linked, recessive disease caused by mutations of the dystrophin gene at the Xp21 locus. Dystrophin is composed of four distinct structural domains: (i) an N-terminal "actin binding" domain; (ii) a middle "rod" domain consisting of spectrin-like repeats; (iii) a cysteine-rich domain; and (iv) a carboxyl-terminal domain. Various dystrophin full-length isoforms have been detected. The predominant dystrophin isoform found in skeletal muscles is a cytoskeletal protein of approximately 427 kDa that is expressed at the sarcolemma (the plasma membrane of the muscle cell), where it is part of the dystrophin-associated protein complex ("DAPC").

While the exact function of dystrophin has not been elucidated, it is believed that it serves to link the intracellular microfilament network of actin to the extracellular matrix. In other words, dystrophin anchors the sarcolemma to the actin cytoskeleton in the sarcoplasm (the cytoplasm of the muscle cell) and plays an important role during muscle contraction and muscle stretch. Dystrophin is thought to be an elastic and flexible protein (due to the triple helix repeats in its rod domain) and probably protects the muscle cell from the stresses caused by the force created during muscle contraction. A marked reduction in the levels of DAPCs at the sarcolemma are observed in dystrophin-deficient skeletal muscle from DMD patients and animal models. Thus, the absence of this physical link/interaction between the interior and exterior of the muscle cell renders the sarcolemma fragile, making muscle fibers susceptible to degeneration during repeated cycles of muscle contraction and relaxation.

Typically, DMD patients are clinically normal at birth except for elevated serum levels of the muscle isoform of creatine kinase as a consequence of muscle fiber degeneration. Physical symptoms of DMD progressively appear throughout childhood with subsequent onset of pseudohypertrophy of the calf muscles and proximal limb muscle weakness. Progressive muscle wasting continues throughout life. Becker MD ("BMD") is a milder form of inherited MD that is also caused by dystrophin mutations. DMD results from an absence of dystrophin or expression of a non-functional protein, whereas BMD has been associated with reduction of wild-type dystrophin or expression of a partially functional protein. Although many genetic causes of the various forms of MD have been identified and characterized, other forms of MD are caused by mutation of other genes that have not yet been defined.

MD, or a form thereof, is usually diagnosed based on tests, such as a muscle biopsy, genetic testing, electromyography or nerve conduction tests (which use electrodes to test muscle and/or nerve function) and blood enzyme tests (which may reveal muscle damage). These tests are usually accompanied with physical exams and evaluation of the patient's family medical history. Management of symptoms in MD patients include exercise, physical therapy, and surgery. In DMD, corticosteriods may slow muscle destruction to an extent, but careful management of steroid therapy is required due to the systemic side effects associated with it. One of the few entities currently being developed for the treatment for muscular dystrophy is stamulumab (MYO-029), an experimental GDF8 (growth and differentiation factor 8) inhibiting recombinant human antibody. Otherwise, there is no other drug known to alter the course of the disease.

As a result of the progress made in understanding the genetic basis and pathophysiology of MD, several strategies for treatment have been explored, but none have yet demonstrated success. For example, gene replacement (e.g., of dystrophin in the case of DMD) and cell replacement (using normal myoblasts or stem cells) strategies are being tested in animals. However, these approaches to treat DMD will require many more years of investigation before they can be applied to humans. Pharmacological approaches under exploration include searching for drugs that increase dystrophin levels (or dystrophin-related protein levels, e.g., utrophin) to compensate for its loss. One such strategy involved the use of gentamicin (an aminoglycoside antibiotic that causes stop codon read-through) to treat DMD caused by a mutation that introduces a premature stop codon within the coding sequence (open reading frame) of dystrophin. Although this strategy was reported to increase dystrophin levels by 10-20% in a mouse model, these results could not be replicated and human clinical trials have shown no increase in expression of dystrophin. Thus, despite the progress made in understanding the genetic basis and pathophysiology of MD or a form thereof, there remains a need for therapies that alter the course of the disease.

SUMMARY OF THE INVENTION

The present invention relates to methods for treating MD or a form thereof. The present invention relates to methods for treating MD or a form thereof using a compound to modulate any of the 5'-UTR (untranslated region) and 3'-UTR, the 5'-UTR or the 3'-UTR of muscle specific insulin-like growth factor 1 ("mIGF1"), α7 integrin ("ITGA7"), or utrophin ("UTRN") mRNA transcripts to increase expression of mIGF1, ITGA7, or UTRN protein, respectively. Compounds that target any of the 5'-UTR and 3'-UTR, the 5'-UTR or the 3'-UTR of a target mRNA (i.e., mIGF1, ITGA7, or UTRN) and post-transcriptionally up-regulate, increase or enhance expression of the target protein (i.e., mIGF1, ITGA7, or UTRN) can be used to treat MD or a form thereof in human subjects in need thereof.

Embodiments of the present invention include a method for treating MD or a form thereof mediated by selectively increasing the endogenous production of mIGF1, ITGA7, or UTRN protein using compounds that target the UTRs of the corresponding mRNA transcripts. Such compounds can be used in a method for the treatment of MD or a form thereof, preferably DMD and BMD, in human subjects in need thereof. Compounds that modulate any of the 5'-UTR and 3'-UTR, the 5'-UTR or the 3'-UTR of a target mRNA (i.e., mIGF1, ITGA7, or UTRN) and up-regulate, increase or enhance expression of the target protein (i.e., mIGF1, ITGA7, or UTRN) can be used in therapeutic regimens for the treatment of MD, preferably DMD, in human subjects in need thereof.

In one embodiment, compounds specifically target any of the 5'-UTR and 3'-UTR, the 5'-UTR or the 3'-UTR of mIGF1 mRNA and post-transcriptionally up-regulate, increase or enhance expression of mIGF1 protein. In another embodiment, compounds specifically target ITGA7 mRNA and post-transcriptionally increase expression of ITGA7 protein. In yet another embodiment, compounds specifically target any of the 5'-UTR and 3'-UTR, the 5'-UTR or the 3'-UTR of UTRN mRNA and post-transcriptionally up-regulate, increase or enhance expression of UTRN protein. Such compounds can be used in a method for the treatment of MD or a form thereof in human subjects in need thereof.

The invention also relates to screening assays for the identification and validation of compounds that target any of the 5'-UTR and 3'-UTR, the 5'-UTR or the 3'-UTR of a target mRNA (i.e., mIGF1, ITGA7, or UTRN). In particular, these assays involve the use of a nucleic acid construct comprising a reporter gene operably linked to any of the 5'-UTR and 3'-UTR, the 5'-UTR or the 3'-UTR of a target (i.e., mIGF1, ITGA7, or UTRN). Transcription of the reporter gene can be driven by any promoter, and need not be limited to a mIGF1, ITGA7, or UTRN promoter. Indeed, strong promoters, such as the CMV promoter may be preferred for use in screening assays. Accordingly, the nucleic acid construct optionally comprises one or more operably linked promoters. Included within the scope of the present invention are those compounds that specifically modulate any of the 5'-UTR and 3'-UTR, the 5'-UTR or the 3'-UTR of the mIGF1, ITGA7, or UTRN mRNA to up-regulate post-transcriptional expression of a mIGF1, ITGA7 or UTRN gene or a reporter gene.

In specific embodiments, a nucleic acid construct comprises a reporter gene operably linked to (i) the 5'-UTR of a target or a fragment, mutant or post-transcriptional regulatory element thereof and a 3'-UTR of a target or a fragment, mutant or post-transcriptional regulatory element thereof; (ii) the 5'-UTR of a target or a fragment, mutant or post-transcriptional regulatory element thereof; or (iii) the 3'-UTR of a target or a fragment, mutant or post-transcriptional regulatory element thereof, wherein the target is selected from the group consisting of mIGF1, ITGA7 and UTRN, and wherein the 5'-UTR is upstream of the reporter gene and the 3'-UTR is downstream of the reporter gene. In some embodiments, the nucleic acid construct further comprises one or more promoters operably linked to the reporter gene. In one embodiment, a vector comprises the nucleic acid construct. In another embodiment, a host cell contains the nucleic acid construct.

In yet another embodiment, a host cell contains a vector that comprises the nucleic acid construct.

In a specific embodiment, the present invention provides methods for identifying or validating a compound that modulates UTR-dependent expression of a target gene comprising the steps of: (a) contacting a compound with the host cell expressing a reporter protein via a nucleic acid construct comprising a reporter gene and (i) the 5'-UTR of a target or a fragment, mutant or post-transcriptional regulatory element thereof and a 3'-UTR of a target or a fragment, mutant or post-transcriptional regulatory element thereof; (ii) the 5'-UTR of a target or a fragment, mutant or post-transcriptional regulatory element thereof; or (iii) the 3'-UTR of a target or a fragment, mutant or post-transcriptional regulatory element thereof, wherein the target is selected from the group consisting of mIGF1, ITGA7 and UTRN, and wherein the 5'-UTR is upstream of the reporter gene and the 3'-UTR is downstream of the reporter gene; and (b) detecting the amount or activity of a reporter protein, wherein a compound that modulates UTR-dependent expression of the target gene is identified or validated if the amount or activity of said reporter protein detected in the presence of the compound is altered relative to a previously determined reference range or the amount or activity of said reporter protein detected in the absence of said compound or the presence of a negative control. A compound that up-regulates UTR-dependent expression of the target is identified or validated if the amount or activity of said reporter protein in the presence of the compound is up-regulated relative to a previously determined reference range or the amount or activity of said reporter protein detected in the absence of said compound or the presence of a negative control.

In another embodiment, the present invention provides methods for identifying or validating a compound that modulates UTR-dependent expression of a target gene comprising the steps of: (a) contacting a compound with a cell-free extract containing a RNA transcribed in vitro from a nucleic acid construct comprising a reporter gene and (i) the 5'-UTR of a target or a fragment, mutant or post-transcriptional regulatory element thereof and a 3'-UTR of a target or a fragment, mutant or post-transcriptional regulatory element thereof; (ii) the 5'-UTR of a target or a fragment, mutant or post-transcriptional regulatory element thereof; or (iii) the 3'-UTR of a target or a fragment, mutant or post-transcriptional regulatory element thereof, wherein the target is selected from the group consisting of mIGF1, ITGA7 and UTRN, and wherein the 5'-UTR is upstream of the reporter gene and the 3'-UTR is downstream of the reporter gene; and (b) detecting the amount or activity of a reporter protein translated from said RNA, wherein a compound that modulates UTR-dependent expression of the target gene is identified or validated if the amount or activity of said reporter protein detected in the presence of the compound is altered relative to a previously determined reference range or relative to the amount or activity of said reporter protein detected in the absence of said compound or the presence of a negative control. A compound that up-regulates UTR-dependent expression of the target is identified or validated if the amount or activity of said reporter protein is detected in the presence of the compound is up-regulated relative to a previously determined reference range or the amount or activity of said reporter protein in the absence of said compound or the presence of a negative control.

The invention is based, in part, on the Applicants' discovery of cis-regulatory elements or trans-regulatory complexes that bind to such cis-elements in the 5'-UTR and 3'-UTR, the 5'-UTR or the 3'-UTR of mIGF1, ITGA7, or UTRN mRNA, that post-transcriptionally modulate the expression of mIGF1, ITGA7, or UTRN protein, respectively. Compounds selected for use in the invention include those compounds that destabilize or decrease the activity of either inhibitory cis-elements or trans-regulatory complexes that bind to such inhibitory cis-elements in any of the 5'-UTR and 3'-UTR, the 5'-UTR or the 3'-UTR of the mIGF1, ITGA7, or UTRN mRNA and post-transcriptionally increase expression of mIGF1, ITGA7, or UTRN protein, respectively. Compounds selected for use in the invention also include those compounds that stabilize or enhance the activity of enhancer cis-elements or trans-regulatory complexes that bind to such enhancer cis-elements in any of the 5'-UTR and 3'-UTR, the 5'-UTR or the 3'-UTR of the mIGF1, ITGA7, or UTRN mRNA and post-transcriptionally increase expression of mIGF1, ITGA7, or UTRN protein, respectively.

The UTR targeted approach of the invention has several advantages. In particular, the sequences of the 5'-UTR and 3'-UTR appear to be unique to each of the transcripts (i.e., mIGF1, ITGA7, or UTRN). Therefore, compounds that are highly specific for these UTRs (i.e., mIGF1, ITGA7, or UTRN), can be used to selectively up-regulate post-transcriptional expression of the target gene (i.e., mIGF1, ITGA7, or UTRN). Further, up-regulating the post-transcriptional expression of the mIGF1, ITGA7, or UTRN gene selectively targets only cells that contain the mIGF1, ITGA7, or UTRN mRNA transcripts, respectively. The use of such compounds in the methods of the invention should, therefore, have reduced side effects to non-specific targets and cells. Moreover, the UTR targeted approach of the invention exploits the endogenous regulatory elements of mIGF1, ITGA7, or UTRN expression, thus, avoiding many technical, safety, and efficacy issues involved with other therapeutic approaches envisioned for the treatment of MD or a form thereof, e.g., genetic approaches to deliver DNA encoding therapeutic genes or to modify endogenous mutated genes. Thus, the methods of the present invention offer several advantages, in terms of increased specificity and efficacy and reduced side effects.

Without being bound by any particular theory, the compounds that target any of the 5'-UTR and 3'-UTR, the 5'-UTR or the 3'-UTR of the target mRNA (i.e., mIGF1, ITGA7, or UTRN), when used therapeutically, may increase expression of the target in patients with MD and certain forms thereof, particularly DMD or BMD, and reduce, ameliorate or prevent skeletal muscle degeneration. Thus, the present invention is directed to a method for up-regulating the expression of a target (i.e., mIGF1, ITGA7, or UTRN) protein in a human subject in need thereof, comprising administering an effective amount of a compound to the human subject, which compound has demonstrated activity for enhancing post-transcriptional expression of a nucleic acid construct comprising a reporter gene operably linked to any of the 5'-UTR and 3'-UTR, the 5'-UTR or the 3'-UTR of the target (i.e., mIGF1, ITGA7, or UTRN) in vitro or in cultured cells.

Accordingly, the present invention is further directed to a method for treating MD or a form thereof in a human subject in need thereof, comprising administering to the human subject an effective amount of a compound for up-regulating expression of a target protein (i.e., mIGF1, ITGA7, or UTRN), wherein said compound increases the post-transcriptional expression of a nucleic acid construct comprising a reporter gene operably linked to any of the 5'-UTR and 3'-UTR, the 5'-UTR or the 3'-UTR of a target (i.e., mIGF1, ITGA7, or UTRN) in vitro or in cultured cells.

In one embodiment, a method for treating MD or a form thereof in a human subject in need thereof, comprises administering to the human subject an effective amount of a compound that up-regulates in vitro or in cultured cells the post-transcriptional expression of a nucleic acid construct comprising a reporter gene operably linked to (i) the 5'-UTR of a target, or (ii) the 3'-UTR of a target, or (iii) the 5'-UTR and 3'-UTR of a target gene, wherein the 5'-UTR is upstream of the reporter gene and the 3'-UTR is downstream of the reporter gene, and wherein the target is selected from mIGF1, ITGA7, or UTRN. In another embodiment, the method further comprises administering to the subject one or more additional agents. In a specific embodiment, the additional agents are each independently selected from the group consisting of: an agent that down-regulates the expression of a GDF8 protein, a different agent that up-regulates the expression of a mIGF1 protein, a different agent that up-regulates the expression of an ITGA7 protein, and a different agent that up-regulates the expression of a UTRN protein. In yet another embodiment, the form of MD is selected from Duchenne muscular dystrophy (DMD), Becker muscular dystrophy (BMD), limb girdle muscular dystrophy, congenital muscular dystrophy, facioscapulohumeral muscular dystrophy, myotonic muscular dystrophy, oculopharyngeal muscular dystrophy, distal muscular dystrophy and Emery-Dreifuss muscular dystrophy.

An embodiment of one or more uses and methods of the present invention is directed to a compound that up-regulates post-transcriptional expression of a target gene (i.e., mIGF1, ITGA7, or UTRN) or a pharmaceutically acceptable free acid, free base, salt, ester, hydrate, solvate, polymorph, clathrate, geometric isomer, stereoisomer, racemate, enantiomer or tautomer thereof selected from the group consisting of:

1
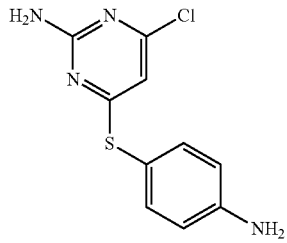

2
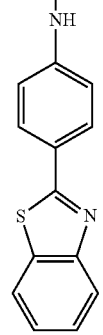

3
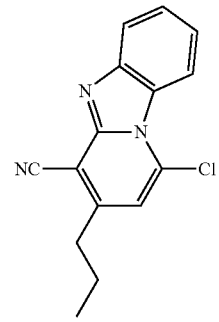

4
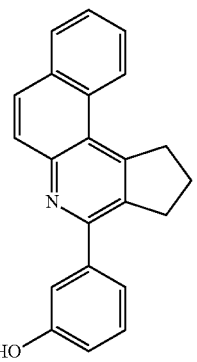

5
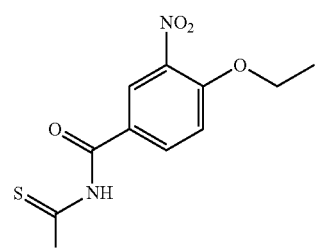

6
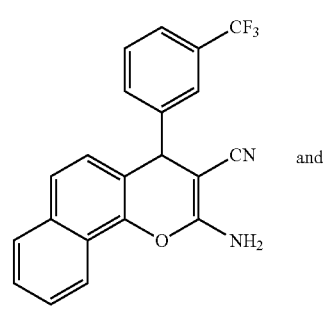

and

-continued

7

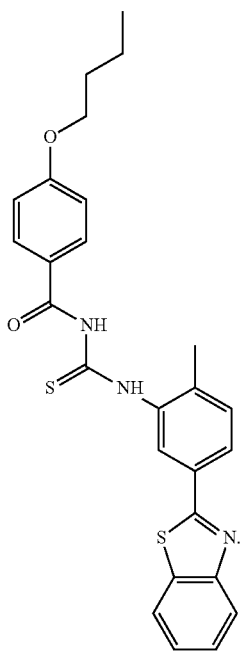

In a specific embodiment, the present invention provides methods for up-regulating the expression of a target protein in a human subject in need thereof, comprising administering to the human subject an effective amount of a compound, wherein the compound is: 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yl)phenol, N-(4-(benzo[d]thiazol-2-yl)phenylcarbamothioyl)-4-ethoxy-3-nitrobenzamide, 2-amino-4-(3-(trifluoromethyl)phenyl)-4H-benzo[h]chromene-3-carbonitrile, or N-(5-(benzo[d]thiazol-2-yl)-2-methylphenylcarbamothioyl)-4-butoxybenzamide, or a pharmaceutically acceptable free acid, free base, salt, ester, hydrate, solvate, polymorph, clathrate, geometric isomer, stereoisomer, racemate, enantiomer or tautomer thereof.

In another embodiment, the present invention provides methods for treating MD or a form thereof in a human subject in need thereof, comprising administering to the human subject an effective amount of a compound that up-regulates in vitro or in cultured cells the post-transcriptional expression of a nucleic acid construct comprising a reporter gene operably linked to (i) the 5'-UTR of a target, or (ii) the 3'-UTR of a target, or (iii) the 5'-UTR and 3'-UTR of a target, wherein the target is mIGF1, ITGA7, or UTRN, and wherein the 5'-UTR is upstream of the reporter gene and the 3'-UTR is downstream of the reporter gene. In a specific embodiment, the compound is: 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yl)phenol, N-(4-(benzo[d]thiazol-2-yl)phenylcarbamothioyl)-4-ethoxy-3-nitrobenzamide, 2-amino-4-(3-(trifluoromethyl)phenyl)-4H-benzo[h]chromene-3-carbonitrile, or N-(5-(benzo[d]thiazol-2-yl)-2-methylphenylcarbamothioyl)-4-butoxybenzamide; or a pharmaceutically acceptable free acid, free base, salt, ester, hydrate, solvate, polymorph, clathrate, geometric isomer, stereoisomer, racemate, enantiomer or tautomer thereof.

In yet another embodiment, the present invention provides methods for treating MD or a form thereof in a human subject in need thereof, comprises administering to the human subject an effective amount of a pharmaceutical composition comprising: 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yl)phenol, N-(4-(benzo[d]thiazol-2-yl)phenylcarbamothioyl)-4-ethoxy-3-nitrobenzamide, 2-amino-4-(3-(trifluoromethyl)phenyl)-4H-benzo[h]chromene-3-carbonitrile, or N-(5-(benzo[d]thiazol-2-yl)-2-methylphenylcarbamothioyl)-4-butoxybenzamide; or a pharmaceutically acceptable free acid, free base, salt, ester, hydrate, solvate, polymorph, clathrate, geometric isomer, stereoisomer, racemate, enantiomer or tautomer thereof, in an admixture with a pharmaceutically acceptable carrier, excipient, or diluent.

TERMINOLOGY

As used herein, the italicized form of "mIGF1", "ITGA7", or "UTRN", unless otherwise specified or clear from the context of the specification, refers to a mIGF1 nucleic acid sequence, ITGA7 nucleic acid sequence, and UTRN nucleic acid sequence, respectively. The nucleic acid sequence may be DNA or RNA.

As used herein, the term "about" or "approximately" when used in conjunction with a number refers to any number within 0.25%, 0.5%, 1%, 5% or 10% of the referenced number.

As used herein, the term "compound," unless otherwise specified or clear from the context of the specification, refers to any agent that is being tested for its ability to modulate post-transcriptional expression of a target gene (i.e., mIGF1, ITGA7, or UTRN), or has been identified as post-transcriptionally modulating the expression of a target gene (i.e., mIGF1, ITGA7, or UTRN). In a specific embodiment, a compound is any agent that is tested for its ability to modulate untranslated region-dependent expression of a target gene, i.e., mIGF1, ITGA7, or UTRN, or has been identified as modulating the expression of a target mRNA, i.e., mIGF1, ITGA7, or UTRN. In one embodiment, a compound is a purified small molecule including, but not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, or a molecular weight less than about 5,000 grams per mole, or a molecular weight less than about 1,000 grams per mole, or a molecular weight less than about 500 grams per mole, or a molecular weight less than about 100 grams per mole, and salts, esters, and other pharmaceutically acceptable forms thereof.

As used herein, the term "purified," in the context of a compound, refers to a compound that is substantially free of chemical precursors, intermediate compounds or other chemicals (such as reagents, solvents and the like) after being separated from the synthetic reaction mixture. In a specific embodiment, the compound is 60%, preferably 65%, 70%, 75%, 80%, 85%, 90%, or 99% free of such other, different chemicals or compounds. In a specific embodiment, a compound described herein is purified.

As used herein, the term "fragment" in the context of a nucleotide sequence refers to a nucleotide sequence comprising an nucleic acid sequence of at least 5 contiguous nucleic acid residues, at least 10 contiguous nucleic acid residues, at least 15 contiguous nucleic acid residues, at least 20 contiguous nucleic acid residues, at least 25 contiguous nucleic acid residues, at least 40 contiguous nucleic acid residues, at least 50 contiguous nucleic acid residues, at least 60 contiguous nucleic acid residues, at least 70 contiguous nucleic acid residues, at least contiguous 80 nucleic acid residues, at least contiguous 90 nucleic acid residues, at least contiguous 100 nucleic acid residues, at least contiguous 125 nucleic acid residues, at least 150 contiguous nucleic acid residues, at least contiguous 175 nucleic acid residues, at least contiguous 200 nucleic acid residues, or at least contiguous 250 nucleic acid residues of the nucleotide sequence of the gene of interest, e.g., mIGF1, ITGA7, or UTRN. The nucleic acid may be RNA, DNA, or a chemically modified variant thereof. In a specific embodiment, the fragment is a fragment of a UTR of mIGF1, ITGA7, or UTRN.

As used herein, the term "host cell" includes a particular subject cell transformed or transfected with a nucleic acid construct of the present invention and the progeny or potential progeny of such a cell. Progeny of such a cell may not be identical to the parent cell transfected with the nucleic acid construct due to mutations or environmental influences that may occur in succeeding generations or integration of the nucleic acid construct into the host cell genome.

As used herein, the term "MD or a form thereof" encompasses any muscle disorder caused by a defect in one or more genes that control muscle function and/or is characterized by gradual wasting of skeletal muscle. Non-limiting examples of MD or a form thereof include, but are not limited to, DMD, BMD, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy. In some embodiments, MD or a form thereof, encompasses multi-system disorders with manifestations in body systems including, but not limited to, the heart, gastrointestinal and nervous systems, endocrine glands, skin, eyes and other organs. Non-limiting examples of such multi-system disorders include motor neuron diseases such as, but not limited to, Amyotrophic Lateral Sclerosis (ALS) (also known as Lou Gehrig's Disease), Spinal Muscular Atrophy Type 1 (SMA1, also known as Werdnig-Hoffmann Disease), Spinal Muscular Atrophy Type 2 (SMA2), Spinal Muscular Atrophy Type 3 (SMA3, also known as Kugelberg-Welander Disease) and Spinal Bulbar Muscular Atrophy (SBMA) (also known as Kennedy Disease and X-Linked SBMA); metabolic muscle diseases such as, but not limited to, Phosphorylase Deficiency (MPD or PYGM) (also known as McArdle Disease), Acid Maltase Deficiency (AMD) (also known as Pompe Disease), Phosphofructokinase Deficiency (also known as Tarui Disease), Debrancher Enzyme Deficiency (DBD) (also known as Cori or Forbes Disease), Mitochondrial Myopathy (MITO), Carnitine Deficiency (CD), Carnitine Palmityl Transferase Deficiency (CPT), Phosphoglycerate Kinase Deficiency, Phosphoglycerate Mutase Deficiency, Lactate Dehydrogenase Deficiency and Myoadenylate Deaminase Deficiency; peripheral nerve diseases such as, but not limited to, Charcot-Marie-Tooth Disease (CMT) (also known as Hereditary Motor and Sensory Neuropathy (HMSN) or Peroneal Muscular Atrophy (PMA)), Friedreich's Ataxia (FA) and Dejerine-Sottas Disease (DS) (chromosome 19 recessive form can be called CMT4F); inflammatory myopathies such as, but not limited to, Dermatomyositis (DM), Polymyositis (PM) and Inclusion Body Myositis (IBM); diseases of the neuromuscular junction such as, but not limited to, Myasthenia Gravis (MG), Lambert-Eaton Syndrome (LES) and Congenital Myasthenic Syndrome (CMS); myopathies due to endocrine abnormalities such as, but not limited to, Hyperthyroid Myopathy (HYPTM) and Hypothyroid Myopathy (HYPOTM); and other myopathies such as, but not limited to, Myotonia Congenita (MC) (two forms: Thomsen and Becker Disease), Paramyotonia Congenita (PC), Central Core Disease (CCD), Nemaline Myopathy (NM), Myotubular Myopathy/Centronuclear Myopathy (MTM or CNM) and Periodic Paralysis (PP) (two forms: Hypokalemic and Hyperkalemic) (see, Muscular Dystrophy Association website).

In some embodiments, the terms "nucleic acid", "nucleotide" and "polynucleotide" refer to deoxyribonucleotides, deoxyribonucleic acids, ribonucleotides, and ribonucleic acids, and polymeric forms thereof, and include either single- or double-stranded forms. In certain embodiments, such terms include known analogues of natural nucleotides, for example, peptide nucleic acids ("PNA"s), that have similar binding properties as the reference nucleic acid. In some embodiments, such terms refer to deoxyribonucleic acids (e.g., cDNA or DNA). In other embodiments, such terms refer to ribonucleic acid (e.g., mRNA or RNA).

As used herein, the term "ORF" refers to the open reading frame of a mRNA, i.e., the region of the mRNA that is translated into protein.

As used herein, the term "previously determined reference range" refers to a reference range for the expression of a reporter gene expressed either by an instant nucleic acid construct or the target gene, i.e., mIGF1, ITGA7, or UTRN from a particular cell or in a particular cell-free extract. Ideally, each laboratory will establish its own reference range for each assay, each cell type or each cell-free extract. In one embodiment, at least one positive control and at least one negative control are included for use in the assay. In an embodiment, the previously determined reference range is the amount or activity of a reporter protein or target protein (i.e., mIGF1, ITGA7, or UTRN) detected in the presence of a negative control, such as DMSO.

As used herein, the term "UTR" refers to an "untranslated region" of the nucleotide sequence of a mRNA or a DNA sequence or chemical analogue thereof that is transcribed into a mRNA in which the nucleotides corresponding to the open reading frame ("ORF") are not present. In some embodiments, the UTR is the region of a mRNA that is not translated into protein. In one embodiment, the UTR is either or both a 5'-UTR, i.e., upstream of the ORF coding region, or a 3'-UTR, i.e., downstream of the ORF coding region.

As used herein, the term "untranslated region-dependent expression" or "UTR-dependent expression" refers to the regulation of gene expression through the untranslated region's regulatory elements at the level of mRNA expression, i.e., during or after transcription of the gene from the DNA has begun. In one embodiment, the term "untranslated region-dependent expression" or "UTR-dependent expression" refers to the regulation of mRNA translation.

As used herein, the terms "reporter gene expression," "expression of a reporter gene" or "expression of a nucleic acid construct comprising a reporter gene" are used coextensively and refer to the amount or activity of the reporter protein detected in the assays described herein.

As used herein, the term "effective amount" in the context of administering a compound to a subject refers to the amount of a compound which is sufficient to achieve at least one or more of the following effects: (i) reduce or ameliorate the severity of MD or a form thereof or a symptom associated therewith; (ii) prevent the progression of MD or a form thereof or a symptom associated therewith; (iii) cause regression of MD or a form thereof or a symptom associated therewith; (iv) prevent the development or onset of MD or a form thereof or a symptom associated therewith; (v) prevent the recurrence of a symptom associated with MD or a form thereof; (vi) reduce the loss of muscle strength; (vii) reduce the loss of muscle cells; (viii) enhance or improve muscle strength; (ix) increase muscle cells; (x) reduce muscle dystrophy; (xi) increase motor function; (xii) reduce the duration of a symptom associated with MD or a form thereof; (xiii) reduce the number of symptoms associated with MD or a form thereof; (xiv) reduce hospitalization associated with MD or a form thereof in a subject; (xv) reduce hospitalization length associated with MD or a form thereof; (xvi) increase the survival of a subject having MD or a form thereof; and (xvii) enhance or improve the prophylactic or therapeutic effect(s) of another agent.

An "isolated" nucleic acid sequence, nucleotide sequence, or polynucleotide sequence is one which is separated from other nucleic acid molecules which are present in a natural source of the nucleic acid sequence or nucleotide sequence. Moreover, an "isolated" nucleic acid sequence, or nucleotide sequence, or polynucleotide sequence, such as a cDNA or RNA molecules, can be substantially free of other cellular material or culture medium when produced by recombinant techniques, or substantially free of chemical precursors when chemically synthesized. In certain embodiments, an "isolated" nucleic acid sequence, nucleotide sequence, or polynucleotide sequence is a nucleic acid sequence, nucleotide sequence, or polynucleotide sequence that is recombinantly expressed in a heterologous cell. In a specific embodiment, a nucleic acid construct described herein is isolated.

As used herein, the term "in combination," refers, in the context of the administration of a compound of the present invention, to the administration of one or more compounds that up-regulate the expression of a target protein (i.e., mIGF1, ITGA7, or UTRN) post-transcriptionally alone or in combination with one or more additional agents for use in treating MD or a form thereof. The use of the term "in combination" does not restrict the order in which one or more compounds of the present invention or another agent are administered to a human subject having MD or a form thereof.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "human toddler" refers to a human that is 1 year to 3 years old.

As used herein, the terms "subject" or "patient" are used interchangeably. As used herein, the terms "subject" and "subjects" refer to an animal, preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the term "synergistic," refers to the effect of the administration of a combination product as described herein which is more effective than the additive effects of any two or more single agents. In a specific embodiment, a synergistic effect of a combination product permits the use of lower dosages of one or more agents and/or less frequent administration of said agents to a subject with MD or a form thereof. In certain embodiments, the ability to utilize lower dosages of an agent and/or to administer said agents less frequently reduces the toxicity associated with the administration of said agents to a subject without reducing the efficacy of said agents in the prevention or treatment of MD or a form thereof. In some embodiments, a synergistic effect results in improved efficacy of each of the agents in treating MD or a form thereof. In some embodiments, a synergistic effect of a combination of agents avoids or reduces adverse or unwanted side effects associated with the use of any single agent. The combination of agents in such a product can be administered to a subject in the same pharmaceutical composition. Alternatively, the agents can be administered concurrently to a subject in separate pharmaceutical compositions. The agents may also be administered to a subject by the same or different routes of administration. In a specific embodiment, at least one of the agents is a compound.

As used herein, the term "treat" refers to treatment from which a subject receives a beneficial effect such as the reduction, decrease, attenuation, diminishment, stabilization, remission, suppression, inhibition or arrest of the development or progression of MD or a form thereof, or a symptom thereof. In certain embodiments, the treatment that a subject receives results in at least one or more of the following effects: (i) reduce or ameliorate the severity of MD or a form thereof or a symptom associated therewith; (ii) prevent the progression of MD or a form thereof or a symptom associated therewith; (iii) cause regression of MD or a form thereof or a symptom associated therewith; (iv) prevent the development or onset of MD or a form thereof or a symptom associated therewith; (v) prevent the recurrence of a symptom associated with MD or a form thereof; (vi) reduce the loss of muscle strength; (vii) reduce the loss of muscle cells; (viii) enhance or improve muscle strength; (ix) increase muscle cells; (x) reduce muscle dystrophy; (xi) increase motor function; (xii) reduce the duration of a symptom associated with MD or a form thereof; (xiii) reduce the number of symptoms associated with MD or a form thereof; (xiv) reduce hospitalization associated with MD or a form thereof in a subject; (xv) reduce hospitalization length associated with MD or a form thereof; (xvi) increase the survival of a subject having MD or a form thereof; and (xvii) enhance or improve the prophylactic or therapeutic effect(s) of another agent. In some embodiments, the treatment that a subject receives does not cure MD or a form thereof, but prevents the progression or worsening of the disease.

As used herein, the term "form" in the context of a compound refers to a compound isolated for use as a pharmaceutically acceptable free acid, free base, salt, ester, hydrate, solvate, polymorph, clathrate, geometric isomer, stereoisomer, racemate, enantiomer or tautomer thereof.

As used herein, the term "pharmaceutically acceptable" refers to a component that is, within the scope of sound medical judgment, suitable for use in contact with the tissues of humans and other mammals without undue toxicity, irritation, allergic response and the like, and are commensurate with a reasonable benefit/risk ratio.

As used herein, the term "pharmaceutically acceptable salt" refers to any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a subject in need thereof. Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" refers to a compound which further includes a stoichiometric or non-stoichiometric amount of water bound by non-covalent intermolecular forces.

As used herein, the term "solvate" refers to a compound which further includes a stoichiometric or non-stoichiometric amount of solvent such as water, acetone, ethanol, methanol, dichloromethane, 2-propanol, or the like, bound by non-covalent intermolecular forces.

BRIEF DESCRIPTION OF THE DRAWINGS

FIGS. 1A-C: Sequence of the human mIGF1 (Muscle specific Insulin-like Growth Factor) 5' UTR (FIG. 1A) (SEQ ID NO: 1) and 3' UTR (FIGS. 1B-1C) (SEQ ID NO: 2).

FIGS. 2A-B: Sequence of the ITGA7 (Human α7 integrin) 5' UTR (FIG. 2A) (SEQ ID NO: 3) and 3' UTR (FIG. 2B) (SEQ ID NO: 4).

FIGS. 3A-B: Sequence of the UTRN (Utrophin) 5' UTR (FIG. 3A) (SEQ ID NO: 5) and 3' UTR (FIG. 3B) (SEQ ID NO: 6).

FIG. 4A-D: UTRN 3' UTR Sequence Alignment between Mouse (SEQ ID NO: 7) and Human (SEQ ID NO: 8). Shaded residues indicate conserved residues. Top line represents mouse sequence, bottom line represents human sequence.

DETAILED DESCRIPTION OF THE INVENTION

The present invention provides compounds for use in the treatment of MD or a form thereof. In one embodiment, the form of MD is DMD or BMD. In particular, the present invention provides a method for the treatment of MD or a form thereof in a human subject in need thereof, comprising administering an effective amount of a compound to the human subject, wherein said compound increases the post-transcriptional expression of a nucleic acid construct comprising a reporter gene operably linked to any of the 5'-UTR and 3'-UTR, the 5'-UTR or the 3'-UTR of a target (i.e., mIGF1, ITGA7, or UTRN) in vitro or in cultured cells. In specific embodiments, the target is mIGF1, ITGA7, or UTRN mRNA.

Without being bound by any particular theory, the compounds target any of the 5'-UTR and 3'-UTR, the 5'-UTR or the 3'-UTR of a target mRNA (i.e., mIGF1, ITGA7, or UTRN) and increase the expression of the target (i.e., mIGF1, ITGA7, or UTRN, respectively) protein in patients having MD or a form thereof, which provides a therapeutic benefit. In a specific embodiment, the compounds target any of the 5'-UTR and 3'-UTR, the 5'-UTR or the 3'-UTR of mIGF1 mRNA and increase the expression of mIGF1 protein in patients having MD or a form thereof, which provides a therapeutic benefit. In another embodiment, the compounds target any of the 5'-UTR and 3'-UTR, the 5'-UTR or the 3'-UTR of mIGF1 mRNA and increase the expression of mIGF1 protein in muscle cells of patients having MD or a form thereof, which provides a therapeutic benefit. In another embodiment, the compounds target any of the 5'-UTR and 3'-UTR, the 5'-UTR or the 3'-UTR of ITGA7 mRNA and increase the expression of ITGA7 protein in patients having MD or a form thereof, which provides a therapeutic benefit. In another embodiment, the compounds target any of the 5'-UTR and 3'-UTR, the 5'-UTR or the 3'-UTR of UTRN mRNA and increase the expression of UTRN protein in patients having MD or a form thereof, which provides a therapeutic benefit.

The present invention provides screening assays for the identification or validation of compounds that target any of the 5'-UTR and 3'-UTR, the 5'-UTR or the 3'-UTR of target mRNA transcripts (i.e., mIGF1, ITGA7, or UTRN). These assays involve the use of a nucleic acid construct comprising a reporter gene operably linked to any of the 5'-UTR and 3'-UTR, the 5'-UTR or the 3'-UTR of a target mRNA (i.e., mIGF1, ITGA7, or UTRN). Compounds that specifically increase the post-transcriptional activity of any of the 5'-UTR and 3'-UTR, the 5'-UTR or the 3'-UTR of a target mRNA (i.e., mIGF1, ITGA7, or UTRN) and enhance expression of the reporter gene are expected to provide a therapeutic benefit. In a particular embodiment, the compounds modulate the expression of a target (i.e., mIGF1, ITGA7, or UTRN) protein post-transcriptionally by affecting the protein or regulatory complexes that bind to or associate with one or more of the UTRs.

Compounds

The compounds screened in the in vitro and cultured host cell assays of the present invention have demonstrated activity for increasing the post-transcriptional expression of a nucleic acid construct comprising a reporter gene operably linked to any of the 5'-UTR and 3'-UTR, the 5'-UTR or the 3'-UTR of target (i.e., mIGF1, ITGA7, or UTRN) and, thus may post-transcriptionally increase or enhance expression of the target protein (i.e., mIGF1, ITGA7, or UTRN). In another specific embodiment, the compounds are specific for any of the 5'-UTR and 3'-UTR, the 5'-UTR or the 3'-UTR of target mRNA transcripts (i.e., mIGF1, ITGA7, or UTRN) and, thus may post-transcriptionally increase or enhance expression of the target protein (i.e., mIGF1, ITGA7, or UTRN) by stabilizing the mRNA transcripts of the target (i.e., mIGF1, ITGA7, or UTRN) protein.

Accordingly, the uses and methods of the present invention are directed to a compound or a pharmaceutically acceptable free acid, free base, salt, ester, hydrate, solvate, polymorph, clathrate, geometric isomer, stereoisomer, racemate, enantiomer or tautomer thereof for use in modulating UTR-dependent expression of a target gene, wherein the target gene is each selected from mIGF1, ITGA7 or UTRN, and wherein the compound is selected from the group consisting of:

| Cpd | Name |
|---|---|
| 1 | 4-(4-aminophenylthio)-6-chloropyrimidin-2-amine, |
| 2 | N,N-dimethyl-4-(5-nitro-1H-benzo[d]imidazol-2-yl)aniline, |
| 3 | 1-chloro-3-propyl-benzoimidazo[1,2-a]pyridine-4-carbonitrile, |
| 4 | 3-(2,3-dihydro-1H-benzo[f]cyclopenta[c]quinolin-4-yl)phenol, |
| 5 | N-(4-(benzo[d]thiazol-2-yl)phenyl-carbamothioyl)-4-ethoxy-3-nitrobenzamide, |
| 6 | 2-amino-4-(3-(trifluoromethyl)phenyl)-4H-benzo[h]chromene-3-carbonitrile, and |
| 7 | N-(5-(benzo[d]thiazol-2-yl)-2-methyl-phenylcarbamothioyl)-4-butoxybenzamide. |

In a specific embodiment, the compound is a pharmaceutically acceptable free acid, free base, salt, ester, hydrate, solvate, polymorph, clathrate, geometric isomer, stereoisomer, racemate, enantiomer or tautomer of compound 1, 2, 3, 4, 5, 6, or 7 above.

Nucleic Acid Constructs

The present invention provides nucleic acid constructs comprising a reporter gene operably linked to any of the 5'-UTR and 3'-UTR, the 5'-UTR or the 3'-UTR of a target (i.e., mIGF1, ITGA7, or UTRN) or a fragment, mutant or a post-transcriptional regulatory element thereof. The nucleic acid constructs of the invention may be used in the instant screening assays to identify or validate compounds that post-transcriptionally enhance the expression of a protein translated from a target mRNA transcript (i.e., mIGF1, ITGA7, or UTRN).

Muscle Specific Insulin-Like Growth Factor 1 (mIGF1)

Transcripts encoding the mIGF1 isoform are initiated in exon 1, and include alternatively spliced exons to encode a protein terminating with an Ea peptide. The Ea peptide is characteristic of IGF1 isoforms synthesized by resting muscle. Transcripts initiating at exon 2 are widely expressed in all tissues. Three different alternative splice sites at the 3' end of the RNA generate E peptides with a common 16 amino acid sequence and alternative C-terminal sequences. Ea transcripts are found in extra-hepatic tissues (such as muscle), whereas Eb transcripts are common in the liver. A third E peptide variant results from a novel splice acceptor site in exon 5 and is generated in muscles subjected to stretch (MGF). The 5'-UTR of mIGF1 is approximately 165 nucleotides in length (FIG. 1A). The 3'-UTR of mIGF1 is approximately 6,631 nucleotides in length (FIG. 1B).

Integrin α7 (ITGA7)

Integrins are the major family of cell surface adhesion receptors and are responsible for cell-cell and cell-matrix interaction. They are heterodimeric integral membrane proteins composed of an alpha chain and a beta chain. The ITGA7 chain undergoes post-translational cleavage within the extracellular domain to yield a disulfide-linked light and heavy chain that join with β1 to form an integrin that binds to the extracellular matrix protein laminin-1. ITGA7-β1 is the major integrin complex expressed in differentiated muscle cells. Splice variants of ITGA7 that differ in both the extracellular and cytoplasmic domains exist in the mouse; however, to date only a single human transcript type has been isolated. ITGA7 is encoded by a gene on human chromosome 12q13. Mutations cause congenital myopathies. The 5'-UTR of ITGA7 is approximately 161 nucleotides in length (FIG. 2A). The 3'-UTR of ITGA7 is approximately 504 nucleotides in length (FIG. 2B).

Utrophin (UTRN)

Figure 4C:
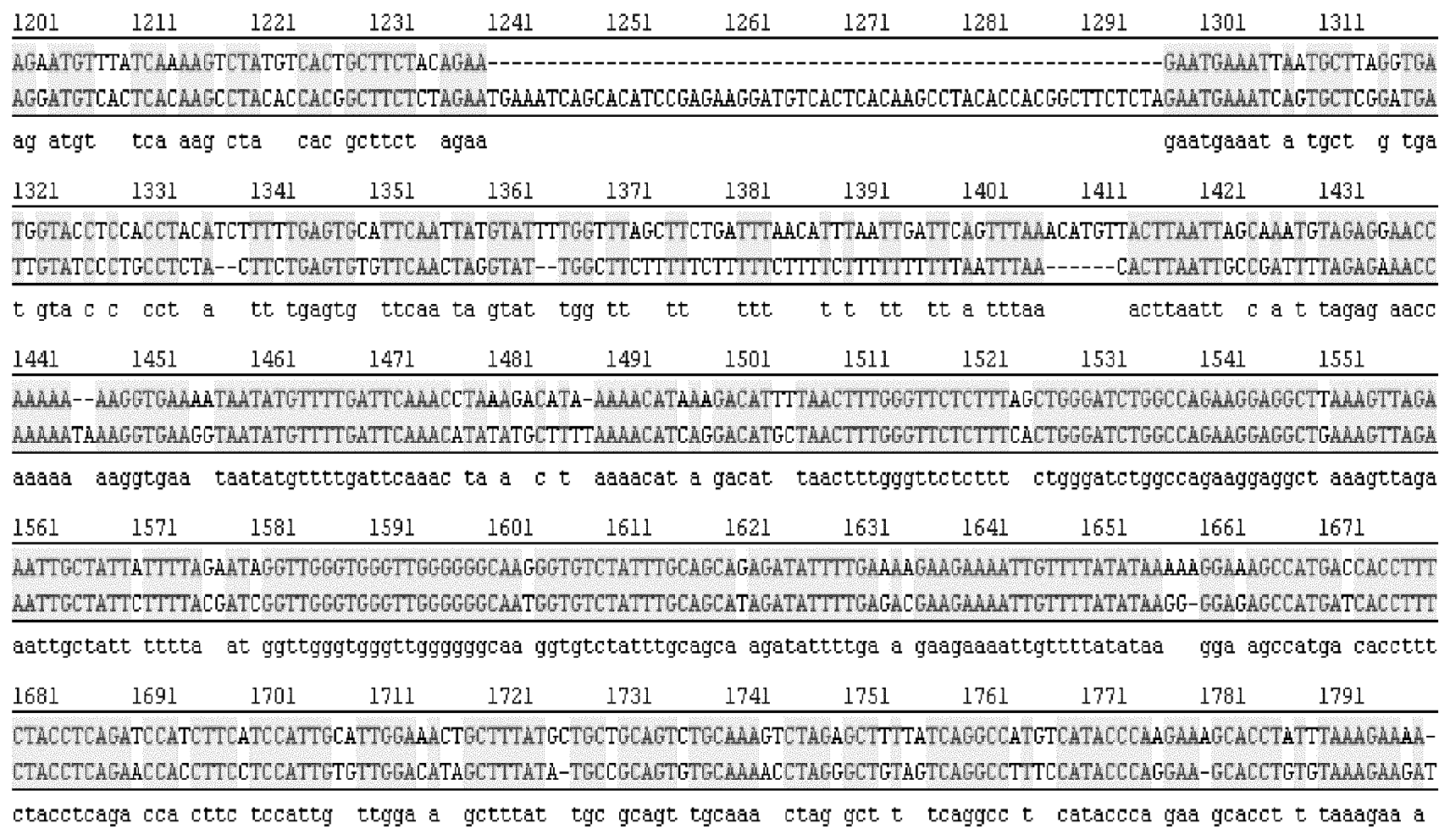
Figure 4D:
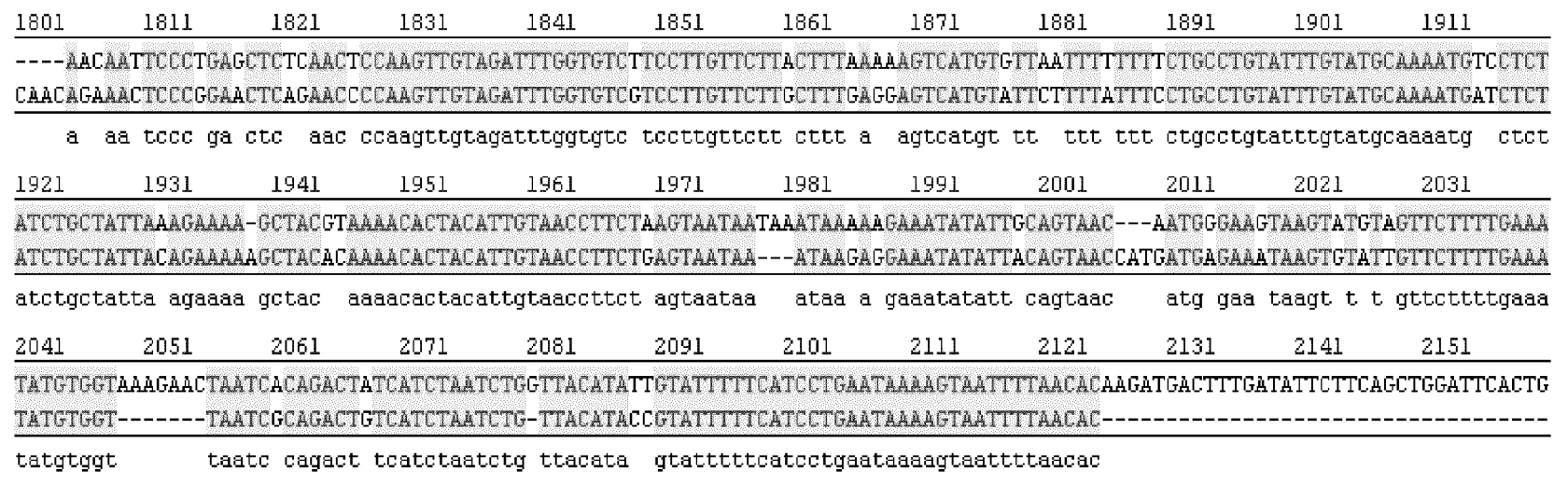

The 5'-UTR of UTRN is approximately 497 nucleotides in length (FIG. 3A), and the 3'-UTR of UTRN is approximately 2000 nucleotides in length, is AU-rich. The 3'-UTR of UTRN has six AU-rich elements and is highly conserved between mouse and human (FIG. 3B; FIG. 4). Investigation of the function of the 3'-UTR on gene expression in skeletal muscle cells has demonstrated that UTRN mRNA transcripts localize with cytoskeleton-bound polyribosomes. Localization of the transcript affects translation and has a direct influence on the amount of UTRN protein that is produced in muscle cells (see, e.g., Jasmin et al., 2002, J. Physiol. Paris. 96:31-42; and Gramolini et al., 2001 J. Cell. Biol. 154, 1173-1183).

The present invention provides a nucleic acid construct comprising the 5'-UTR of a target (i.e., mIGF1, ITGA7, or UTRN) (FIGS. 1A, 2A, 3A, respectively) or a fragment, mutant or post-transcriptional regulatory element thereof and a reporter gene, wherein the 5'-UTR or fragment, mutant or post-transcriptional regulatory element thereof is operably linked to the reporter gene and the 5'-UTR or fragment thereof is 5' (upstream) to the reporter gene. In a specific embodiment, the nucleic acid construct further comprises a different 3'-UTR which is unrelated to a target, (i.e., mIGF1, ITGA7, or UTRN), wherein the 3'-UTR is 3' (downstream) of the reporter gene. The present invention also provides a nucleic acid construct comprising the 3'-UTR of a target (i.e., mIGF1, ITGA7, or UTRN) (FIGS. 1B, 2B, 3B, respectively) or a fragment, mutant or post-transcriptional regulatory element thereof, wherein the 3'-UTR or fragment thereof is operably linked to the reporter gene and the 3'-UTR or fragment thereof is 3' (downstream) to the reporter gene. In a specific embodiment, the nucleic acid construct further comprises a different 5'-UTR which is unrelated to a target (i.e., mIGF1, ITGA7, or UTRN), wherein the 5'-UTR is 5' (upstream) of the reporter gene.

The present invention also provides a nucleic acid construct comprising, in 5' to 3' order: the 5'-UTR of a target (i.e., mIGF1, ITGA7, or UTRN) or a fragment, mutant or post-transcriptional regulatory element thereof, a reporter gene, and the 3'-UTR of a target (i.e., mIGF1, ITGA7, or UTRN) or a fragment, mutant or post-transcriptional regulatory element thereof, wherein the 5'-UTR or fragment, mutant or post-transcriptional regulatory element thereof and the 3'-UTR or fragment, mutant or post-transcriptional regulatory element thereof are operably linked to the reporter gene, and wherein the 5'-UTR or fragment, mutant or post-transcriptional regulatory element thereof is 5' (upstream) to the reporter gene and the 3'-UTR or fragment, mutant or post-transcriptional regulatory element thereof is 3' (downstream) to the reporter gene.

The present invention provides nucleic acid constructs comprising a reporter gene and a nucleotide sequence comprising a mutated form of the 5'-UTR of a target (i.e., mIGF1, ITGA7, or UTRN) or a fragment thereof, wherein the nucleotide sequence is operably linked to the reporter gene and the nucleotide sequence is upstream of the reporter gene. In a specific embodiment, the nucleic acid construct further comprises a different 3'-UTR which is unrelated to a target, (i.e., mIGF1, ITGA7, or UTRN), wherein the 3'-UTR is 3' (downstream) of the reporter gene. The present invention provides nucleic acid constructs comprising a reporter gene and a nucleotide sequence comprising a mutated form of the 3'-UTR of a target (i.e., mIGF1, ITGA7, or UTRN) or fragment thereof, wherein the nucleotide sequence is operably linked to the reporter gene and the nucleotide sequence is downstream of the reporter gene. In a specific embodiment, the nucleic acid construct further comprises a different 5'-UTR which is unrelated to a target (i.e., mIGF1, ITGA7, or UTRN), wherein the 5'-UTR is 5' (upstream) of the reporter gene.

The present invention also provides a nucleic acid construct comprising a reporter gene, a first nucleotide sequence comprising a mutated form of the 5'-UTR of a target (i.e., mIGF1, ITGA7, or UTRN) or a fragment thereof, and a second nucleotide sequence comprising a mutated form of the 3'-UTR of a target (i.e., mIGF1, ITGA7, or UTRN) or a fragment thereof, wherein the first nucleotide sequence and the second nucleotide sequence are operably linked to the reporter gene, and wherein the first nucleotide sequence is upstream of the reporter gene and the second nucleotide sequence is downstream of the reporter gene.

In certain embodiments, a mutated form of the 5'-UTR of a target (i.e., mIGF1, ITGA7, or UTRN) or a fragment thereof contains 1, 2, 3, 4, 5, 6, 7, 8, 9, 10 or more mutations. Alternatively, the mutated form of the 5'-UTR of the target (i.e., mIGF1, ITGA7, or UTRN) or a fragment thereof contains an amount of mutations in a range of from about one to about five mutations, from about two to about eight mutations or from about five to about ten mutations. In certain embodiments, a mutated form of the 3'-UTR of a target (i.e., mIGF1, ITGA7, or UTRN) or a fragment thereof contains 1, 2, 3, 4, 5, 6, 7, 8, 9, 10 or more mutations. Alternatively, the mutated form of the 3'-UTR of the target (i.e., mIGF1, ITGA7, or UTRN) or a fragment thereof contains an amount of mutations in a range of from about one to about five mutations, from about two to about eight mutations or from about five to about ten mutations. Such mutations may include, but are not limited to, insertions, deletions, and/or substitutions.

In certain embodiments, a nucleotide sequence comprising a mutated form of the 5'-UTR of a target (i.e., mIGF1, ITGA7, or UTRN) is 65%, 75%, 80%, 85%, 90%, 95%, 98% or 99% identical to the nucleotide sequence of the 5'-UTR of said target (i.e., mIGF1, ITGA7, or UTRN, respectively). In some embodiments, a nucleotide sequence comprising a mutated form of the 3'-UTR of a target (i.e., mIGF1, ITGA7, or UTRN) is 65%, 75%, 80%, 85%, 90%, 95%, 98% or 99% identical to the nucleotide sequence of the 3'-UTR of said target (i.e., mIGF1, ITGA7, or UTRN, respectively). Percent identity can be determined using any method known to one of skill in the art. In a specific embodiment, the percent identity is determined using the "Best Fit" or "Gap" program of the Sequence Analysis Software Package™ (Version 10; Genetics Computer Group, Inc., University of Wisconsin Biotechnology Center, Madison, Wis.). See, e.g., U.S. Patent Application Publication No. US 2005/0048549, paragraph 74, for information regarding these programs.

In certain embodiments, a nucleotide sequence comprising a mutated form of the 5'-UTR of a target (i.e., mIGF1, ITGA7, or UTRN) hybridizes to the nucleotide sequence of the 5'-UTR of said target (i.e., mIGF1, ITGA7, or UTRN, respectively). In certain embodiments, a nucleotide sequence comprising a mutated form of the 3'-UTR of a target (i.e., mIGF1, ITGA7, or UTRN) hybridizes to the nucleotide sequence of the 3'-UTR of said target (i.e., mIGF1, ITGA7, or UTRN, respectively). In specific embodiments, a nucleotide sequence comprising a mutated form of the 5'-UTR of a target (i.e., mIGF1, ITGA7, or UTRN) hybridizes under stringent conditions to a nucleotide sequence of the 5'-UTR of said target (i.e., mIGF1, ITGA7, or UTRN, respectively) having at least 20 nucleic acids, at least 30 nucleic acids, at least 40 nucleic acids, at least 50 nucleic acids, at least 100 nucleic acids, or at least 150 nucleic acids of the nucleotide sequence of the 5'-UTR of a target (i.e., mIGF1, ITGA7, or UTRN). In a specific embodiment, a nucleotide sequence comprising a mutated form of the 5'-UTR of a target (i.e., mIGF1, ITGA7, or UTRN) hybridizes under high stringency, intermediate or lower stringency hybridization conditions to a nucleotide sequence of the 5'-UTR of said target (i.e., mIGF1, ITGA7, or UTRN, respectively) or a fragment thereof. In specific embodiments, a nucleotide sequence comprising a mutated form of the 3'-UTR of a target (i.e., mIGF1, ITGA7, or UTRN) hybridizes under stringent conditions to a nucleotide sequence of the 3'-UTR of said target (i.e., mIGF1, ITGA7, or UTRN, respectively) having at least 20 nucleic acids, at least 30 nucleic acids, at least 40 nucleic acids, at least 50 nucleic acids, at least 100 nucleic acids, or at least 150 nucleic acids of the nucleotide sequence of the 3'-UTR of a target (i.e., mIGF1, ITGA7, or UTRN). In a specific embodiment, a nucleotide sequence comprising a mutated form of the 3'-UTR of a target (i.e., mIGF1, ITGA7, or UTRN) hybridizes under high stringency, intermediate or lower stringency hybridization conditions to a nucleotide sequence of the 3'-UTR of said target (i.e., mIGF1, ITGA7, or UTRN, respectively) or a fragment thereof. Hybridization conditions are well known in the art and are described, e.g., in U.S. Patent Application Publication No. US 2005/0048549 (e.g., ¶¶72 and 73), which is herein incorporated by reference in its entirety.

The present invention provides nucleic acid constructs comprising a reporter gene and a nucleotide sequence comprising a post-transcriptional regulatory element from any of the 5'-UTR and 3'-UTR, the 5'-UTR or the 3'-UTR of a target (i.e., mIGF1, ITGA7, or UTRN). In one embodiment, the present invention provides nucleic acid constructs comprising a reporter gene and a nucleotide sequence comprising two or more post-transcriptional regulatory elements from any of the 5'-UTR and 3'-UTR, the 5'-UTR or the 3'-UTR of a target (i.e., mIGF1, ITGA7, or UTRN).

In some embodiments, the nucleic acid construct may further comprise a stable hairpin secondary structure inserted into a UTR of a target (i.e., mIGF1, ITGA7, or UTRN). In some embodiments, an intron is inserted into a UTR (e.g., the 5'-UTR) or at the 5' end of an ORF of a target (i.e., mIGF1, ITGA7, or UTRN). In some embodiments, both a stable hairpin secondary structure and an intron are added to the nucleic acid construct. Such insertions and other techniques known to one of skill in the art can be used to obtain increased mRNA expression.

The reporter gene in the nucleic acid constructs can be positioned such that the translation of the mRNA transcribed from that reporter gene is dependent upon the mode of translation initiation, such as, but not limited to, cap-dependent translation or cap-independent translation (i.e., translation via an internal ribosome entry site).

In addition to the UTR of a target (i.e., mIGF1, ITGA7, or UTRN) and the reporter gene, the nucleic acid constructs may further comprise one or more transcriptional regulatory element(s). The transcriptional regulatory elements are typically 5' to the 5'-UTR of a target (i.e., mIGF1, ITGA7, or UTRN) and direct the transcription of the reporter gene. In some embodiments, one or more of the transcriptional regulatory elements that are endogenous to the target (i.e., mIGF1, ITGA7, or UTRN) are used to control the transcription of a reporter gene. In other embodiments, one or more transcriptional regulatory elements that are heterologous to the target (i.e., mIGF1, ITGA7, or UTRN) are used to control the transcription of a reporter gene. Any transcriptional regulatory element(s) known to one of skill in the art may be used to control the transcription of the reporter gene. Non-limiting examples of the types of transcriptional regulatory element(s) include a constitutive promoter, a tissue-specific promoter, and an inducible promoter. In a specific embodiment, the transcription of the reporter gene is controlled, at least in part, by a mammalian (in some embodiments, human) transcriptional regulatory element(s). In one embodiment, the nucleic acid construct of the present invention optionally comprises one or more operably linked promoters. In a more specific embodiment, the transcription of the reporter gene is controlled, at least in part, by a strong promoter, such as CMV.

Specific examples of promoters which may be used to control the transcription of the reporter gene include, but are not limited to, the SV40 early promoter region, the promoter contained in the 3' long terminal repeat of Rous sarcoma virus, the herpes thymidine kinase promoter, the regulatory sequences of the metallothionein gene adenovirus (ADV), cytomegalovirus (CMV), bovine papilloma virus (BPV), parovirus B19p6 promoter, prokaryotic expression vectors such as the .beta.-lactamase promoter, or the tac promoter, plant expression vectors comprising the nopaline synthetase promoter region or the cauliflower mosaic virus 35S RNA promoter, and the promoter of the photosynthetic enzyme ribulose biphosphate carboxylase, promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells, insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in myeloid cells, myelin basic protein gene control region which is active in oligodendrocyte cells in the brain, myosin light chain-2 gene control region which is active in skeletal muscle, and gonadotropic releasing hormone gene control region which is active in the hypothalamus.

The nucleic acid constructs may be part of a vector that provides transcriptional regulatory elements and optionally, translational regulatory elements. The vector chosen will depend upon a variety of factors, including, without limitation, the strength of the transcriptional regulatory elements and the host cell or cell-free extract to be used to express the reporter gene. Non-limiting examples of host cell-vector systems that may be used to express the reporter gene include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker.

In a specific embodiment, a nucleic acid construct comprises a promoter operably linked to a reporter gene flanked by one or both UTRs of a target (i.e., mIGF1, ITGA7, or UTRN), origins of replication from one or more species, and optionally, one or more selectable markers (e.g., an antibiotic resistance gene). In one embodiment, the nucleic acid construct is part of a CMV vector, such as pcDNA™3.1/Hygro (Invitrogen Corp., Carlsbad, Calif.). In other embodiments, the nucleic acid construct is part of a T7 vector, a lac vector, pCEP4 vector or 5.0/FRT vector. The nucleic acid constructs can be monocistronic or multicistronic. A multicistronic nucleic acid construct may encode 2, 3, 4, 5, 6, 7, 8, 9, 10 or more, or in the range of 2-5, 5-10 or 10-20 reporter genes. For example, a dicistronic nucleic acid construct may comprise in 5' to 3' order: a promoter, a first reporter gene, a 5'-UTR of a target (i.e., mIGF1, ITGA7, or UTRN), a second reporter gene and optionally, a 3'-UTR of said target (i.e., mIGF1, ITGA7, or UTRN, respectively). In such a nucleic acid construct, the transcription of both reporter genes is driven by the promoter, whereas the translation of the mRNA from the first reporter gene is by a cap-dependent scanning mechanism and the translation of the mRNA from the second reporter gene is by a cap-independent mechanism such as by an IRES. The IRES-dependent translation of the mRNA of the second reporter gene can then be normalized against cap-dependent translation.

In some embodiments, a vector contains a nucleic acid construct comprising a reporter gene operably linked to (i) the 5'-UTR (untranslated region) of a target gene or a fragment, mutant or post-transcriptional regulatory element thereof and a 3'-UTR of a target gene or a fragment, mutant or post-transcriptional regulatory element thereof; (ii) the 5'-UTR of a target nucleic acid or a fragment, mutant or post-transcriptional regulatory element thereof; or (iii) the 3'-UTR of a target gene or a fragment, mutant or post-transcriptional regulatory element thereof, wherein the target gene is selected from the group consisting of mIGF1 (muscle specific insulin-like growth factor 1), ITGA7 (α7 integrin) and UTRN (utrophin), and wherein the 5'-UTR is upstream of the reporter gene and the 3'-UTR is downstream of the reporter gene.

Expression vectors containing the nucleic acid construct of the present invention can be identified by four general approaches: (a) nucleic acid sequencing, (b) nucleic acid hybridization, (c) presence or absence of "marker" nucleic acid functions, and (d) expression of inserted sequences. In the first approach, the presence of the UTRs and/or the reporter gene inserted in an expression vector can be detected by sequencing. In the second approach, the presence of the UTRs and/or the reporter gene inserted in an expression vector can be detected by nucleic acid hybridization using probes comprising sequences that are homologous to the inserted UTRs and/or reporter gene. In the third approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid of interest, i.e., the nucleic acid construct, in the vector. For example, if the nucleic acid of interest is inserted within the marker nucleic acid sequence of the vector, recombinants containing the insert can be identified by the absence of the marker nucleic acid function. In the fourth approach, recombinant expression vectors can be identified by assaying the reporter gene product expressed by the recombinant. Such assays can be based, for example, on the physical or functional properties of the particular reporter gene.

Techniques for practicing aspects of this invention will employ, unless otherwise indicated, conventional techniques of molecular biology, microbiology, and recombinant DNA manipulation and production, which are routinely practiced by one of skill in the art.

Reporter Genes

Any reporter gene well-known to those of skill in the art may be used in nucleic acid constructs to ascertain the effect of a compound on post-transcriptional regulation of expression of a target (i.e., mIGF1, ITGA7, or UTRN). Reporter genes refer to a nucleotide sequence encoding or coding for a protein that is readily detectable, when expressed, either by its presence, amount or activity. A reporter gene can encode or code for a fusion protein. In a specific embodiment, a reporter gene comprises a first nucleotide sequence encoding or coding for a protein that is readily detectable and a second nucleotide sequence, wherein the first and second nucleotide sequence are operably linked and such linkage is not found in nature. Reporter genes may be obtained and the nucleotide sequence of the reporter gene determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+RNA, isolated from, any tissue or cells expressing a reporter protein from the reporter gene) by PCR amplification. Once the nucleotide sequence of a reporter gene is determined, the nucleotide sequence of the reporter gene may be manipulated using methods well-known in the art for the manipulation of nucleotide sequences (e.g., recombinant DNA techniques, site directed mutagenesis, PCR, etc.) to generate reporter genes having a different amino acid sequence, for example to create amino acid substitutions, deletions, and/or insertions.

Examples of reporter genes include, but are not limited to, nucleotide sequences encoding or coding for luciferase (e.g., firefly luciferase, Renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("β-gal"), beta-glucoronidase, beta-lactamase, chloramphenicol acetyltransferase ("CAT"), and alkaline phosphatase ("AP"). The characteristics and methods for using the aforementioned reporter genes are known to one of skill in the art. In one embodiment, a reporter gene utilized in the nucleic acid constructs is easily assayed and has an activity which is not normally found in the cell or organism of interest. In another embodiment, a reporter gene utilized in the nucleic acid constructs is not a target gene (i.e., mIGF1, ITGA7, or UTRN) or a nucleotide sequence encoding or coding for a target protein (i.e., mIGF1, ITGA7, or UTRN).

Cells and Transfection Techniques

A host cell may be transformed or transfected with a nucleic acid construct described herein. In certain embodiments, the use of stable transformants is preferred. In one embodiment, the host cell is a mammalian cell. In another embodiment, the host cell is a human cell. In another embodiment, the host cells are primary cells isolated from a tissue or other biological sample of interest. Host cells that can be used in the methods described herein include, but are not limited to, hybridomas, pre-B cells, 293 cells, 293T cells, 293H cells, HeLa cells, HepG2 cells, K562 cells, 3T3 cells, MCF7 cells, SkBr3 cells, BT474 cells, RD cells, A204 cells, or neuroblastoma cells lines such as MC-IXC, SK-N-MC, SK-N-MC, SK-N-DZ, SH-SY5Y, and BE(2)-C. In one embodiment, the host cells are immortalized cell lines derived from a source, e.g., muscle tissue. In another embodiment, the host cells are stem cells. In another embodiment, the host cells are muscle cells. In yet another embodiment, the host cells are from an adult, e.g., a human adult. Other host cells that can be used in the present invention include, but are not limited to, bacterial cells, yeast cells, virally-infected cells, or plant cells.

Transformation may be by any known method for introducing polynucleotides into a host cell, for example by packaging the polynucleotide in a virus and transducing a host cell with the virus, and by direct uptake of the polynucleotide. The transformation procedure used depends upon the host to be transformed. Such methods are well-known to those of skill in the art.

In one embodiment, stable cell lines expressing a reporter protein via the nucleic acid constructs of interest are generated for high throughput screening. Such stable cells lines may be generated by introducing a nucleic acid construct further comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

In some embodiments, a host cell contains a vector comprising a nucleic acid construct comprising a reporter gene operably linked to (i) the 5'-UTR (untranslated region) of a target gene or a fragment, mutant or post-transcriptional regulatory element thereof and a 3'-UTR of a target gene or a fragment, mutant or post-transcriptional regulatory element thereof; (ii) the 5'-UTR of a target nucleic acid or a fragment, mutant or post-transcriptional regulatory element thereof; or (iii) the 3'-UTR of a target gene or a fragment, mutant or post-transcriptional regulatory element thereof, wherein the target gene is selected from the group consisting of mIGF1 (muscle specific insulin-like growth factor 1), ITGA7 (α7 integrin) and UTRN (utrophin), and wherein the 5'-UTR is upstream of the reporter gene and the 3'-UTR is downstream of the reporter gene.

Cell-Free Extracts

The invention provides for the translation of the nucleic acid constructs in a cell-free system. Techniques for practicing this specific aspect of this invention will employ, unless otherwise indicated, conventional techniques of molecular biology, microbiology, and recombinant DNA manipulation and production, which are routinely practiced by one of skill in the art. Any technique well-known to one of skill in the art may be used to generate cell-free extracts for translation in vitro (otherwise referred to herein as a cell-free extract). For example, the cell-free extracts for in vitro translation can be generated by centrifuging cells and clarifying the supernatant.

The cell-free extract may be isolated from cells of any species origin. For example, the cell-free extract may be isolated from human cells (e.g., HeLa cells, RD cells, A204 cells), 293 cells, Vero cells, yeast, mouse cells (e.g., cultured mouse cells), rat cells (e.g., cultured rat cells), Chinese hamster ovary (CHO) cells, *Xenopus* oocytes, rabbit reticulocytes, primary cells, cancer cells (e.g., undifferentiated cancer cells), cell lines, wheat germ, rye embryo, or bacterial cell extract. In a specific embodiment, the cells from which the cell-free extract is obtained do not endogenously express the target gene (i.e., mIGF1, ITGA7, or UTRN). In one embodiment, the cell-free extract is an extract isolated from human cells. In another embodiment, the human cells that can be used in the methods described herein, include, but are not limited to HeLa cells, 293 cells, 293T cells, 293H cells, HepG2 cells, K562 cells, 3T3 cells, RD cells, A204 cells, MCF7 cells, SkBr3 cells, BT474 cells, MC-IXC cells, SK-N-MC cells, SK-N-MC cells, SK-N-DZ cells, SH-SY5Y cells, or BE(2)C cells.

Screening Assays
Cell-Based Assays

Host cells transformed or transfected with the nucleic acid construct described herein may be used to screen, identify or validate compounds that modulate the post-transcriptional expression of target gene (i.e., mIGF1, ITGA7, or UTRN). In one embodiment, the cells are stably transfected with the nucleic acid construct. The assays may be conducted by: (a) contacting a compound with a host cell engineered to express a reporter protein via a nucleic acid construct comprising a reporter gene encoding or coding for the reporter protein operably linked to any of the 5'-UTR and 3'-UTR, the 5'-UTR or the 3'-UTR of a target gene (i.e., mIGF1, ITGA7, or UTRN), or a fragment, mutant or post-transcriptional regulatory element thereof; and (b) measuring the expression of said reporter protein. In an embodiment, the 5'-UTR is upstream of the reporter gene and the 3'-UTR is downstream of the reporter gene. In one embodiment, if only the 5'-UTR of a target gene (i.e., mIGF1, ITGA7, or UTRN) is used in a construct, then a UTR unrelated to the 3'-UTR of the target gene may be used as the 3'-UTR in the construct. In another embodiment, if only the 3'-UTR of a target gene (i.e., mIGF1, ITGA7, or UTRN) is used in a construct, then a UTR unrelated to the 5'-UTR of the target gene may be used as the 5'-UTR in the construct.

An alteration in the amount or activity of a reporter protein detected in the presence of a compound relative to a previously determined reference range or relative to the amount or activity of the reporter protein detected in the absence of said compound or the presence of a negative control indicates that a particular compound modulates UTR-dependent expression of the reporter gene, and thus, may modulate UTR-dependent expression of the target gene (i.e., mIGF1, ITGA7, or UTRN, respectively). In one embodiment, a negative control (e.g., PBS, DMSO or another agent that is known to have no effect on the expression of the reporter gene) and a positive control (e.g., an agent that is known to have an effect on the expression of the reporter gene, preferably an agent that effects untranslated region-dependent expression) are included in the cell-based assays described herein.

Accordingly, the present invention is directed to a method for identifying or validating a compound that modulates UTR-dependent expression of a target gene (i.e., mIGF1, ITGA7, or UTRN) comprising the steps of: (a) contacting a compound with a host cell containing a nucleic acid construct comprising a reporter gene operably linked to any of the 5'-UTR and 3'-UTR, the 5'-UTR or the 3'-UTR of a target gene (i.e., mIGF1, ITGA7, or UTRN), or a fragment, mutant or post-transcriptional regulatory element thereof, and (b) detecting the amount or activity of a reporter protein translated from a mRNA transcript transcribed from said reporter gene, wherein a compound that modulates UTR-dependent expression of the target gene is identified or validated if the amount or activity of said reporter protein detected in the presence of the compound is altered relative to a previously determined reference range or the amount or relative to activity of said reporter protein detected in the absence of said compound or the presence of a negative control. In a specific embodiment, a compound that modulates UTR-dependent expression is identified or validated if the amount or activity of said reporter protein detected in the presence of the compound is up-regulated relative to a previously determined reference range or the amount or activity of said reporter protein detected in the absence of said compound or the presence of a negative control. In a specific embodiment, the previously determined reference range is the amount or activity of said reporter protein detected in the presence of a negative control (e.g., PBS or DMSO).

The step of contacting a compound with a host cell expressing or genetically engineered to express a reporter protein via a nucleic acid construct comprising a reporter gene encoding or coding for said reporter protein operably linked to any of the 5'-UTR and 3'-UTR, the 5'-UTR or the 3'-UTR of a target gene (i.e., mIGF1, ITGA7, or UTRN), or a fragment, mutant or post-transcriptional regulatory element thereof may be conducted under physiologic conditions. In specific embodiment, a compound is contacted with the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cells and compounds tested and can be determined using routine experimentation.

The invention provides for contacting a compound with a host cell expressing or genetically engineered to express a reporter protein via a nucleic acid construct comprising a reporter gene encoding or coding for said reporter protein operably linked to any of the 5'-UTR and 3'-UTR, the 5'-UTR or the 3'-UTR of a target gene (i.e., mIGF1, ITGA7, or UTRN), or a fragment, mutant or post-transcriptional regulatory element thereof for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In one embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In one embodiment, the invention provides a method for identifying or validating a compound that modulates UTR-dependent expression of a target gene (i.e., mIGF1, ITGA7, or UTRN), said method comprising: (a) engineering a host cell to express a reporter protein via a nucleic acid construct comprising a reporter gene encoding or coding for said reporter protein operably linked to the any of the 5'-UTR and 3'-UTR, the 5'-UTR or the 3'-UTR of a target (i.e., mIGF1, ITGA7, or UTRN), or a fragment, mutant or post-transcriptional regulatory element thereof in a cell; (b) contacting said cell with a compound; and (c) detecting the amount or activity of said reporter protein, wherein a compound that modulates UTR-dependent expression of the target gene is identified if the amount or activity of said reporter protein detected in the presence of a compound is altered relative to a previously determined reference range or relative to the amount or activity of said reporter protein detected in the absence of said compound or the presence of a negative control (e.g., phosphate buffered saline ("PBS") or dimethyl sulfoxide ("DMSO")). In a specific embodiment, the previously determined reference range is the amount or activity of said reporter protein detected in the presence of a negative control (e.g., PBS or DMSO).

In another embodiment, the invention provides a method for identifying or validating a compound that modulates UTR-dependent expression of a target gene (i.e., mIGF1, ITGA7, or UTRN), said method comprising: (a) contacting a compound with a host cell expressing a reporter protein via a nucleic acid construct comprising a reporter gene encoding or coding for said reporter protein operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof; and (b) detecting the amount or activity of said reporter protein, wherein a compound that modulates UTR-dependent expression of the target gene is identified or validated if the amount or activity of said reporter protein detected in the presence of a compound is altered relative to a previously determined reference range or the amount or activity of said reporter protein detected in the absence of said compound or the presence of a negative control (e.g., PBS or DMSO). In a specific embodiment, the previously determined reference range is the amount or activity of said reporter protein in the presence of a negative control (e.g., PBS or DMSO).

In another embodiment, the invention provides a method for identifying or validating a compound that increases or enhances UTR-dependent expression of a target gene (i.e., mIGF1, ITGA7, or UTRN), said method comprising (a) contacting a compound with a host cell expressing a reporter protein via a nucleic acid construct comprising a reporter gene encoding or coding for said reporter protein operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof; and (b) detecting the amount or activity of a reporter protein, wherein a compound that increases or enhances UTR-dependent expression of the target gene is identified or validated if the amount or activity of said reporter protein detected in the presence of the compound is increased relative to a previously determined reference range, or relative to the amount or activity of said reporter protein detected in the absence of the compound or the presence of a negative control (e.g., PBS or DMSO). In a specific embodiment, the previously determined reference range is the amount or activity of said reporter protein detected in the presence of a negative control (e.g., PBS or DMSO). In certain embodiments, the increase in the amount or activity of said reporter protein is at least 1.5 fold, 2 fold, 3 fold, 4 fold, 5 fold, 6 fold, 7 fold, 8 fold, 9 fold, or 10 fold greater than the amount of activity of said reporter protein detected in the absence of the compound or in the presence of a negative control. In a specific embodiment, the amount or activity of said reporter protein are detected by the same technique when the host cell is contacted with the compound or a control (such as a negative control). In one embodiment, the technique is an immunological technique, such as an ELISA, western blot, etc.

The present invention provides methods of identifying environmental stimuli (e.g., exposure to different concentrations of $CO_2$ and/or $O_2$, stress and different pHs) that modulate UTR-dependent expression of a target gene (i.e., mIGF1, ITGA7, or UTRN) utilizing the cell-based assays described herein. In particular, the invention provides a method of identifying an environmental stimulus, said method comprising (a) contacting a host cell expressing a reporter protein via a nucleic acid comprising a reporter gene encoding or coding for said reporter protein operably linked to any of the 5'-UTR and 3'-UTR, the 5'-UTR or the 3'-UTR of a target gene (i.e., mIGF1, ITGA7, or UTRN), or a fragment, mutant or post-transcriptional regulatory element thereof with an environmental stimulus; and (b) detecting the amount or activity of said reporter protein, wherein a compound that modulates UTR-dependent expression of the target gene is identified if the amount or activity of said reporter protein detected in the presence of an environmental stimuli is altered relative to a previously determined reference range, or relative to the amount or activity of said reporter protein detected in the absence of the compound or the presence of a negative control (e.g., PBS or DMSO). In a specific embodiment, the environmental stimuli does not include a compound.

The expression of a reporter protein in the cell-based reporter-gene assays may be detected by any technique well-known to one of skill in the art. Such methods include, but are not limited to, ELISAs, western blots, and FACs. Methods for detecting the expression of a reporter protein will vary with the reporter gene used. Assays for the various reporter genes are well-known to one of skill in the art. For example, luciferase, beta-galactosidase ("β-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("β-gal"), and alkaline phosphatase ("AP") are assayed by changes in light imaging (e.g., luciferase), spectrophotometric absorbance (e.g., β-gal), or fluorescence (e.g., AP). Assays for changes in light output, absorbance, and/or fluorescence are easily adapted for high throughput screening. For example, β-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Alterations in the expression of a reporter protein may be determined by comparing the amount or activity of the reporter protein to a negative control (e.g., PBS, DMSO or another agent that is known to have no effect on the expression of the reporter gene) and optionally, a positive control (e.g., an agent that is known to have an effect on the expression of the reporter gene, preferably an agent that effects untranslated region-dependent expression). Alternatively, alterations in the expression of a reporter protein may be determined by comparing the amount or activity of the reporter protein to a previously determined reference range.

Cell-Free Assays

A cell-free extract and the nucleic acid construct of the present invention may be used to screen, identify or validate compounds that modulate UTR-dependent expression of a target gene (i.e., mIGF1, ITGA7, or UTRN). The assays may be conducted in a cell-free manner by contacting a compound with a cell-free extract and a nucleic acid construct comprising a reporter gene operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof, and measuring the expression of said reporter gene. The alteration in reporter gene expression relative to a previously determined reference range, or relative to reporter gene expression in the absence of a compound or a negative control in such assays indicates that a particular compound modulates UTR-dependent expression of a target gene (i.e., mIGF1, ITGA7, or UTRN). In one embodiment, a negative control (e.g., PBS, DMSO or another agent that is known to have no effect on the expression of the reporter gene) and a positive control (e.g., an agent that is known to have an effect on the expression of the reporter gene, preferably an agent that effects untranslated region-dependent expression) are included in the cell-free assays described herein. In a specific embodiment, the previously determined reference range is the amount or activity of said reporter protein in the presence of a negative control (e.g., PBS or DMSO).

Typically, the nucleic acid construct used in the cell-free assay is a RNA transcript (e.g., mRNA or pre-mRNA) that has been produced using, e.g., in vitro run-off transcription. For example, a RNA can be made in run-off transcription of a linearized form of a nucleic acid construct that is DNA which contains a bacteriophage promoter, a reporter gene and any of the 5'-UTR and 3'-UTR, the 5'-UTR or the 3'-UTR of a target (i.e., mIGF1, ITGA7, or UTRN), wherein the 5'-UTR is upstream and the 3'-UTR is downstream, and wherein the bacteriophage promoter drives transcription of said reporter gene. Bacteriophage promoters from a T3, SP6 or T7 bacteriophage or any other suitable promoter may be used together with the respective RNA polymerase derived from the corresponding bacteriophage. The present invention also provides nucleic acid constructs that may be prepared by in vitro run-off transcription.

The step of contacting a compound with a cell-free extract containing a nucleic acid construct comprising a reporter gene encoding or coding for said reporter protein operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof may be conducted under conditions approximating or mimicking physiologic conditions. In a specific embodiment, a compound is added to the cell-free extract in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cell-free extract and compounds used and can be determined using routine experimentation.

The invention provides for contacting a compound with a cell-free extract containing a nucleic acid construct comprising a reporter gene encoding or coding for said reporter protein operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof for a specific period of time. For example, the contacting can take place for about 1 minute, 2 minutes, 3 minutes, 4, minutes, 5, minutes, 10 minutes, 15 minutes, 20 minutes, 30 minutes, 1 hour, 2 hours, 3 hours, 4 hours, 5 hours, 10 hours, 15 hours, 20 hours, 1 day, 2 days, 3 days, 4 days, 5 days, or 1 week. In one embodiment, the contacting is about 15 hours, i.e., overnight. The contacting can take place for about 1 minute to 1 week, preferably about 5 minutes to 5 days, more preferably about 10 minutes to 2 days, and even more preferably about 1 hour to 1 day.

In a specific embodiment, the invention provides a method for identifying or validating a compound that modulates untranslated region-dependent expression of a target gene (i.e., mIGF1, ITGA7, or UTRN), said method comprising: (a) contacting a compound with a cell-free extract and a nucleic acid construct comprising a reporter gene operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof; and (b) detecting the amount or activity of a reporter protein translated from said reporter gene, wherein a compound that modulates UTR-dependent expression is identified or validated if the amount or activity of said reporter protein detected in the presence of a compound is altered relative to a previously determined reference range, or the amount or activity of said reporter protein detected in the absence of the compound or the presence of a negative control (e.g., PBS or DMSO).

In a specific embodiment, the invention provides a method for identifying compounds that modulate UTR-dependent expression of a target gene (i.e., mIGF1, ITGA7, or UTRN), said method comprising (a) contacting a compound with a cell-free extract and a RNA (e.g., a mRNA) comprising a reporter gene operably linked to any of the 5'-UTR and 3'-UTR, the 5'-UTR or the 3'-UTR of a target mRNA (i.e., mIGF1, ITGA7, or UTRN), or a fragment, mutant or post-transcriptional regulatory element thereof; and (b) detecting the amount or activity of a reporter protein translated from said reporter gene, wherein a compound that increases or enhances UTR-dependent expression of the target gene is identified or validated if the amount or activity of said reporter protein detected in the presence of the compound is altered relative to a previously determined reference range, or relative to the amount or activity of said reporter protein detected in the absence of the compound or the presence of a control (e.g., PBS or DMSO).

In a specific embodiment, the invention provides a method of increasing or enhancing UTR-dependent expression of a target gene (i.e., mIGF1, ITGA7, or UTRN), said method comprising (a) contacting a compound with a cell-free extract and a nucleic acid construct comprising a reporter gene operably linked to any of the 5'-UTR and 3'-UTR, the 5'-UTR or the 3'-UTR of a target (i.e., mIGF1, ITGA7, or UTRN), or a fragment, mutant or post-transcriptional regulatory element thereof; and (b) detecting the amount or activity of a reporter protein translated from said reporter gene, wherein a compound that increases or enhances UTR-dependent expression of the target gene is identified or validated if the amount or activity of said reporter protein detected in the presence of the compound is increased relative to a previously determined reference range, or relative to the amount or activity of said reporter protein detected in the absence of the compound or the presence of a control (e.g., PBS or DMSO). In one embodiment, the nucleic acid construct is RNA. In a specific embodiment, the previously determined reference range is the amount or activity of said reporter protein in the presence of a negative control (e.g., PBS or DMSO).

The activity of a compound in the in vitro extract can be determined by assaying the amount or activity of a reporter protein translated from a reporter gene, or alternatively, by quantifying the expression of the reporter gene by, for example, labeling the in vitro translated protein (e.g., with $^{35}S$-labeled methionine), or by immunological methods, such as western blot analysis or immunoprecipitation. Such methods are well-known to one of skill in the art.

Direct Binding Assays

Compounds that modulate UTR-dependent expression of a target gene (i.e., mIGF1, ITGA7, or UTRN) can be identified by direct binding assays, such as those known to one of skill in the art. Briefly, direct binding assays may be conducted by attaching one or more compounds to solid supports, e.g., polymer beads, with each solid support having substantially one type of compound attached to its surface. The plurality of solid supports is exposed in aqueous solution to target RNA having a detectable label, forming a dye-labeled target RNA: support-attached compound complex wherein the target RNA is a target (i.e., mIGF1, ITGA7, or UTRN) mRNA transcript or RNA transcript comprising any of the 5'-UTR and 3'-UTR, the 5'-UTR or the 3'-UTR of a target mRNA (i.e., mIGF1, ITGA7, or UTRN), or a fragment, mutant or post-transcriptional regulatory element thereof. Binding of a target RNA molecule to a particular compound labels the solid support, e.g., bead, comprising the compound, which can be physically separated from other, unlabeled solid supports. Alternatively, direct binding assays may be conducted by contacting a target RNA having a detectable label with a compound free in solution, in labeled tubes or microtiter wells, or a microarray wherein the target RNA is selected from a mIGF1, ITGA7, or UTRN mRNA transcript or RNA transcript comprising any of the 5'-UTR and 3'-UTR, the 5'-UTR or the 3'-UTR of a target mRNA (i.e., mIGF1, ITGA7, or UTRN), or a fragment, mutant or post-transcriptional regulatory element thereof.

Identification and Validation of Compounds

Using embodiments of the screening assays described herein, the inventors have identified or validated compounds for their effect on UTR-dependent expression of a target gene (i.e., mIGF1, ITGA7, or UTRN). Further, any compound of interest can be tested for its ability to modulate UTR-dependent expression of a target gene (i.e., mIGF1, ITGA7, or UTRN) using the screening assays described herein.

In a specific embodiment, a compound to be tested may be a nucleic acid, such as an antisense oligonucleotide, which is a nucleotide sequence complementary to a specific DNA or RNA sequence described herein. Antisense oligonucleotides can be deoxyribonucleotides, ribonucleotides, or a combination of both. Nucleic acid molecules including antisense oligonucleotide molecules, can be provided in a DNA construct and introduced into a cell. In another embodiment, a compound is an interfering RNA (RNAi) or microRNA (miRNA). RNAi comprises dsRNA that inhibits the expression of genes with complementary nucleotide sequences. In one embodiment, the dsRNA is 20-25 residues in length, termed small interfering RNAs (siRNA).

In order to exclude the possibility that a particular compound is functioning solely by modulating the expression of a target gene (i.e., mIGF1, ITGA7, or UTRN) in a UTR-independent manner, one or more mutations may be introduced into the untranslated regions operably linked to a reporter gene and the effect on the expression of the reporter gene in an assay as described herein can be determined. For example, a nucleic acid construct comprising the 5'-UTR of a target gene (i.e., mIGF1, ITGA7, or UTRN) may be mutated by deleting a fragment of the 5'-UTR of said target gene (i.e., mIGF1, ITGA7, or UTRN, respectively) or substituting a fragment of the 5'-UTR of a target gene (i.e., mIGF1, ITGA7, or UTRN) with a fragment of the 5'-UTR of another gene and measuring the expression of the reporter gene in the presence and absence of a compound that has been identified or validated in an instant screening assay as described herein. If the deletion of a fragment of the 5'-UTR of a target gene (i.e., mIGF1, ITGA7, or UTRN) or the substitution of a fragment of the 5'-UTR of a target gene (i.e., mIGF1, ITGA7, or UTRN) with a fragment of the 5'-UTR of another gene affects the ability of the compound to modulate the expression of the reporter gene, then the fragment of the 5'-UTR that is deleted or substituted plays a role in the regulation of the reporter gene expression and the regulation, at least in part, is in an untranslated region-dependent manner.

The possibility that a particular compound functions solely by modulating the expression of a target gene (i.e., mIGF1, ITGA7, or UTRN) in an UTR-independent manner may be also determined by changing the vector utilized as a nucleic acid construct. The untranslated regions flanked by a reporter gene from the nucleic acid construct in which an effect on reporter gene expression was detected following exposure to a compound may be inserted into a new nucleic acid construct that has, e.g., different transcriptional regulation elements (e.g., a different promoter) and a different selectable marker. The level of reporter gene expression in the presence of the compound can be compared to the level of reporter gene expression in the absence of the compound or in the presence of a control (e.g., PBS or DMSO). If there is no change in the level of expression of the reporter gene in the presence of the compound relative to the absence of the compound or in the presence of a control, then the compound may be functioning in an untranslated region-independent manner.

The specificity of a particular compound's effect on untranslated region-dependent expression of a target gene (i.e., mIGF1, ITGA7, or UTRN) can also be determined. In particular, the specificity of a particular compound for an untranslated region of a target mRNA (i.e., mIGF1, ITGA7, or UTRN) is determined by (a) contacting the compound of interest with a host cell expressing a reporter protein via a nucleic acid construct comprising a reporter gene encoding said reporter protein operably linked to an UTR of a different gene (i.e., a gene different from a target gene (i.e., mIGF1, ITGA7, or UTRN)) which has an UTR different from said target gene (i.e., mIGF1, ITGA7, or UTRN)); and (b) detecting the amount or activity of said reporter protein, wherein the compound is specific for the untranslated region of the target gene (i.e., mIGF1, ITGA7, or UTRN) if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO).

In another embodiment, the specificity of a particular compound for an untranslated region of a target mRNA (i.e., mIGF1, ITGA7, or UTRN) is determined by (a) contacting the compound of interest with a panel of host cells, each host cell in a different well of a container (e.g., a 48- or 96-well plate) and each host cell expressing a nucleic acid construct comprising a reporter gene operably linked to an UTR of a different gene which has an UTR different from the target (i.e., mIGF1, ITGA7, or UTRN); and (b) detecting the amount or activity of a reporter protein translated from mRNA transcript transcribed from the reporter gene, wherein the compound is specific for the untranslated region of a target mRNA (i.e., mIGF1, ITGA7, or UTRN) if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO). In accordance with this embodiment, the panel may comprise 5, 7, 10, 15, 20, 25, 50, 75, 100 or more cells.

In another embodiment, the specificity of a particular compound for an untranslated region of a target mRNA (i.e., mIGF1, ITGA7, or UTRN) is determined by (a) contacting the compound of interest with a cell-free extract and a nucleic acid comprising a reporter gene operably linked to an UTR of a different gene; and (b) detecting the amount or activity of a reporter protein translated from the reporter gene, wherein the compound is specific for the untranslated region of said target mRNA (i.e., mIGF1, ITGA7, or UTRN) if the amount or activity of said reporter protein detected in the presence of the compound is not altered or is not substantially altered relative to a previously determined reference range, or relative to the amount or activity of said reporter protein detected in the absence of the compound or the presence of a negative control (e.g., PBS or DMSO). As used herein, the term "not substantially altered" means that the compound alters the expression of the reporter gene or target mRNA gene by less than 20%, less than 15%, less than 10%, less than 5%, or less than 2% relative to a negative control such as PBS or DMSO.

In a specific embodiment, the amount or activity of said reporter protein are detected by the same technique when the host cell or cell-free extract is contacted with the compound or a control (such as a negative control). In one embodiment, the technique is an immunological technique, such as an ELISA, western blot, etc.

The compounds identified or validated in the assays described supra that modulate untranslated region-dependent expression of a target gene (i.e., mIGF1, ITGA7, or UTRN) can be further tested for untranslated region-dependent binding to any of the 5'-UTR and 3'-UTR, the 5'-UTR or the 3'-UTR of a target mRNA (i.e., mIGF1, ITGA7, or UTRN), or a fragment or post-transcriptional regulatory element thereof. Furthermore, by assessing the effect of a compound on expression of a target gene (i.e., mIGF1, ITGA7, or UTRN), cis-acting elements, i.e., specific nucleotide sequences, that are involved in untranslated region-dependent expression may be identified. The compound can also be tested for binding to proteins and/or molecules involved in post-transcriptional expression of the target gene (i.e., mIGF1, ITGA7, or UTRN). In one embodiment, the proteins and/or molecules involved in post-transcriptional expression of the target gene bind to cis-acting elements in any of the 5'-UTR and 3'-UTR, the 5'-UTR or the 3'-UTR of a target mRNA.

RNA Binding Assays

The compounds that modulate untranslated region-dependent expression of a target gene (i.e., mIGF1, ITGA7, or UTRN) can be tested for binding to any of the 5'-UTR and 3'-UTR, the 5'-UTR or the 3'-UTR of a target mRNA (i.e., mIGF1, ITGA7, or UTRN), or a fragment or post-transcriptional regulatory element thereof by any method known in the art.

Subtraction Assay

The element(s) of an untranslated region(s) that is (are) necessary for a compound identified or validated in accordance with the methods described herein to modulate untranslated region-dependent expression of a target gene (i.e., mIGF1, ITGA7, or UTRN) can be determined utilizing standard mutagenesis techniques well-known to one of skill in the art. One or more mutations (e.g., deletions, additions and/or substitutions) may be introduced into the untranslated regions operably linked to a reporter gene and the effect on the expression of the reporter gene in an assay as described herein. For example, a nucleic acid construct comprising the 5'-UTR of a target (i.e., mIGF1, ITGA7, or UTRN) may be mutated by deleting a fragment or all of the 5'-UTR of the target (i.e., mIGF1, ITGA7, or UTRN) or substituting a fragment of the 5'-UTR of the target (i.e., mIGF1, ITGA7, or UTRN) with a fragment of the 5'-UTR of another gene and measuring the expression of the reporter gene in the presence and absence of a compound that has been identified or validated in an instant screening assay described herein. If the deletion of a fragment of the 5'-UTR of a target (i.e., mIGF1, ITGA7, or UTRN) or the substitution of a fragment of the 5'-UTR of a target (i.e., mIGF1, ITGA7, or UTRN) with a fragment of the 5'-UTR of another gene affects the ability of the compound to modulate the expression of the reporter gene, then the fragment of the 5'-UTR deleted or substituted plays a role in the regulation of the reporter gene expression.

Standard techniques known to those of skill in the art can be used to introduce mutations in the nucleotide sequence of the untranslated region of a target (i.e., mIGF1, ITGA7, or UTRN), including, for example, site-directed mutagenesis and PCR-mediated mutagenesis. In a specific embodiment, less than 75 nucleic acid residue substitutions, less than 50 nucleic acid residue substitutions, less than 45 nucleic acid residue substitutions, less than 40 nucleic acid residue substitutions, less than 35 nucleic acid residue substitutions, less than 30 nucleic acid residue substitutions, less than 25 nucleic acid residue substitutions, less than 20 nucleic acid residue substitutions, less than 15 nucleic acid residue substitutions, less than 10 nucleic acid residue substitutions, or less than 5 nucleic acid residue substitutions are introduced into the nucleotide sequence encoding or coding for the untranslated region of the target (i.e., mIGF1, ITGA7, or UTRN). In another embodiment, less than 10 elements of an untranslated region of the target (i.e., mIGF1, ITGA7, or UTRN), less than 9 elements of an untranslated region of the target, less than 8 elements of an untranslated region of the target, less than 7 elements of an untranslated region of the target, less than 6 elements of an untranslated region of the target, less than 5 elements of an untranslated region of the target, less than 4 elements of an untranslated region of the target, less than 3 elements of an untranslated region of the target, or less than 2 elements of an untranslated region of the target are mutated at one time.

Assays for Detecting the Expression and Activity of Proteins Encoded by a Target (i.e., mIGF1, ITGA7, or UTRN)

Compounds identified or validated in the assays described herein that modulate untranslated region-dependent expression may be further tested in various in vitro assays (e.g., cell-free assays) or in vivo assays (e.g., cell-based assays) well-known to one of skill in the art or as described herein to determine the effect of said compounds on the expression of a target (i.e., mIGF1, ITGA7, or UTRN) gene from which the untranslated regions of the nucleic acid construct are derived. The specificity of a particular compound's effect on untranslated region-dependent expression of one or more other genes can also be determined utilizing assays well-known to one of skill in the art or described herein.

The expression of the gene products of a target gene (i.e., mIGF1, ITGA7, or UTRN) can be readily detected, e.g., by quantifying the protein and/or RNA encoded by said gene. Many methods standard in the art can be thus employed, including, but not limited to, immunoassays to detect and/or visualize protein expression (e.g., Western blot, immunoprecipitation followed by sodium dodecyl sulfate polyacrylamide gel electrophoresis (SDS-PAGE), immunocytochemistry, etc.) and/or hybridization assays to detect gene expression by detecting and/or visualizing respectively mRNA encoding a gene (e.g., northern assays, dot blots, in situ hybridization, etc.). Such assays are routine and well known in the art. Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G Sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., Western blot analysis. One of skill in the art would be knowledgeable as to the parameters that can be modified to increase the binding of the antibody to an antigen and decrease the background (e.g., pre-clearing the cell lysate with sepharose beads).

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise.

ELISAs generally comprise preparing antigen, coating the well of a 96-well microtiter plate with the antigen, adding the antibody of interest conjugated to a detectable agent such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable agent may be added to the well. Further, instead of coating the well with the antigen, the antibody may be coated to the well. In this case, a second antibody conjugated to a detectable agent may be added following the addition of the antigen of interest to the coated well. One of skill in the art would be knowledgeable as to the parameters that can be modified to increase the signal detected as well as other variations of ELISAs known in the art.

An increased level of target (i.e., mIGF1, ITGA7, or UTRN) protein indicates that the compound may be effective to treat MD or a form thereof. Increased levels of target (i.e., mIGF1, ITGA7, or UTRN) protein in conjunction with no change in the levels of the target (i.e., mIGF1, ITGA7, or UTRN, respectively) gene indicate that the compound affects UTR-dependent expression of target protein and not promoter-dependent expression (transcription) of target RNA. Increased levels of target (i.e., mIGF1, ITGA7, or UTRN) protein in conjunction with increased levels of the target (i.e., mIGF1, ITGA7, or UTRN, respectively) RNA may indicate that the compound affects UTR-dependent expression of target protein and not promoter-dependent expression of target RNA (i.e., transcriptional regulation via the promoter/enhancer of the target gene). Specific examples of cell culture models from patients with MD or a form thereof may be used. Other cell culture models that may be used include, but are not limited to, 293H cells and RD cell cultures. The in vivo effect of the compound can also be assayed by performing immunofluorescence studies using antibodies against the target protein (i.e., mIGF1, ITGA7, or UTRN). Another antibody based separation that can be used to detect the protein of interest is the use of flow cytometry such as by a florescence activated cell sorter ("FACS").

A phenotypic or physiological readout can be used to assess untranslated region-dependent activity of a target (i.e., mIGF1, ITGA7, or UTRN) RNA in the presence and absence of the compound. In one embodiment, a phenotypic or physiological readout can be used to assess untranslated region-dependent activity of a target (i.e., mIGF1, ITGA7, or UTRN) RNA in the presence and absence of the compound. For example, the target gene (i.e., mIGF1, ITGA7, or UTRN) RNA may be overexpressed in a cell in which said target (i.e., mIGF1, ITGA7, or UTRN, respectively) RNA is endogenously expressed. Where a target (i.e., mIGF1, ITGA7, or UTRN) RNA controls untranslated region-dependent expression of the target gene (i.e., mIGF1, ITGA7, or UTRN, respectively), the in vivo effect of the compound can be assayed by quantifying the amount of protein and/or RNA encoded by said gene present in cells and/or biological samples obtained from a subject to which the compound was administered.

In addition to measuring the effect of a compound identified or validated in the reporter gene-based assays described herein on the amount of a target gene (i.e., mIGF1, ITGA7, or UTRN) from which the untranslated regions of the nucleic acid construct were derived, the activity of the protein encoded by a target gene (i.e., mIGF1, ITGA7, or UTRN) can be assessed utilizing techniques well-known to one of skill in the art. For example, the activity of a protein encoded by a target gene (i.e., mIGF1, ITGA7, or UTRN) can be determined by detecting induction of a cellular second messenger (e.g., intracellular $Ca^{2+}$, diacylglycerol, $IP_3$, etc.), detecting the phosphorylation of a protein, detecting the activation of a transcription factor, or detecting a cellular response, for example, cellular differentiation, or cell proliferation. The induction of a cellular second messenger or phosphorylation of a protein can be determined by, e.g., immunoassays well-known to one of skill in the art and described herein. The activation of a transcription factor can be detected by, e.g., electromobility shift assays, and a cellular response such as cellular proliferation can be detected by, e.g., trypan blue cell counts, $^3$H-thymidine incorporation, and flow cytometry.

Secondary Screens of Compounds

Compounds identified or validated to modulate untranslated region-dependent expression of a target (i.e., mIGF1, ITGA7, or UTRN) gene may be tested for biological activity in further assays and/or animal models as described herein or known to those skilled in the art.

Cytotoxicity and Cell Proliferation Assays

In some embodiments, compounds are tested for cytotoxicity in mammalian, preferably human, cell lines. In certain embodiments, cytotoxicity is assessed in one or more of the following non-limiting examples of cell lines: RD (a human muscle cell line); A204 (a human rhabdomyosarcoma cell line); U937 (a human monocyte cell line); primary peripheral blood mononuclear cells (PBMC); Huh7 (a human hepatoblastoma cell line); 293, 293T or 293H (a human embryonic kidney cell line); THP-1 (monocytic cells); a HeLa cell line; neuroblastoma cells lines (such as MC-IXC, SK-N-MC, SK-N-MC, SK-N-DZ, SH-SY5Y, and BE(2)-C). In a specific embodiment, the cell line is a muscle cell line.

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability. In a specific embodiment, muscle cell proliferation may be measured using such assay.

In specific embodiments, cell viability is measured in three-day and seven-day periods using an assay standard in the art, e.g., the CellTiter Glo Assay Kit (Promega) which measures levels of intracellular ATP as an indication of metabolically active cells. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

Compounds can be tested for in vivo toxicity in animal models. For example, animal models, described herein and/or others known in the art, used to test the effects of compounds on MD or a form thereof can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified or validated in accordance with the invention that exhibits large therapeutic indices is preferred. While a compound identified or validated in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified or validated in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method described herein, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography.

Animal Model-Based Screens

Compounds identified or validated in a reporter gene-based assay described herein can be tested for biological activity using animal models for MD or a form thereof. These include transgenic and knock-out animals engineered to mimic the genetic condition of a form of MD coupled to a functional readout system, such as a transgenic o knock-out mouse. Such animal model systems include, but are not limited to, rats, mice, chicken, cows, monkeys, pigs, dogs, rabbits, etc. In a specific embodiment, a compound identified or validated in accordance with the methods described herein is tested in a mouse model system. Such model systems are widely used and well-known to the skilled artisan such as the SCID mouse model or transgenic mice. Animal models of MD have been described in the art, see, e.g., Bogdanovich et al., 2004, J. Mol. Med. 82:102-115, Allamand et al., 2000, Hum. Mol. Genet. 9:2459-2467, and Carpenter et al., 1989, Am. J. Pathol. 135:909-919, which are each incorporated herein by reference in their entirety and for all purposes.

Physiological Assays in MD Patients

The ability of a compound to ameliorate the severity of MD or a symptom associated therewith can be assayed by assessing muscle strength, motor function, and serum levels of protein markers, e.g., creatine kinase, in patients diagnosed with MD. Muscle strength can be assessed by using any method known to those skilled in the art, including, but not limited to, use of a hand-held dynamometer. Muscle testing can be performed to assess right and left hand grip, right and left knee extension, right and left knee flexion, and right and left elbow flexion. Motor function can be assessed by a patient's ability to lie down, roll, sit, crawl, kneel, stand, walk, run, and jump. Pulmonary function tests can be performed on patients according to American Thoracic Society standards, and include, but are not limited to maximum inspiratory pressure, maximum expiratory pressure, cough pressure, forced vital capacity, forced expiratory volume in the first second, and measurement of lung volume.

Manual muscle testing scores can be measured using the Medical Research Council's (MRC) muscle strength scoring method. Quantitative muscle strength can be measured, for example, by using the Pediatric Quantitative Measurement System (PQMS). Primary strength markers include quantitative myometry (QMT) scores of the upper and lower extremities, consisting of paired flexor/extensor groups.

Compositions

Any compound described herein may optionally be in the form of a composition comprising the compound. In certain embodiments provided herein, pharmaceutical compositions comprise an effective amount of a compound for up-regulating target protein (i.e., mIGF1, ITGA7 or UTRN) expression in an admixture with a pharmaceutically acceptable carrier, excipient, or diluent. The pharmaceutical compositions are suitable for veterinary and/or human administration. Accordingly, the present invention is directed to a method for treating MD or a form thereof in a human subject in need thereof, comprising administering to the human subject an effective amount of such a pharmaceutical composition. In another embodiment, the present invention is directed to a use of one or more compounds that up-regulate target protein expression (i.e., mIGF1, ITGA7 or UTRN) for the preparation of a medicament for treating MD or a form thereof in a human subject in need thereof. The form of MD contemplated is selected from DMD, BMD, limb girdle muscular dystrophy, congenital muscular dystrophy, facioscapulohumeral muscular dystrophy, myotonic muscular dystrophy, oculopharyngeal muscular dystrophy, distal muscular dystrophy and Emery-Dreifuss muscular dystrophy.

The pharmaceutical compositions provided herein can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents. Further provided herein are anhydrous pharmaceutical compositions and dosage forms comprising one or more compounds of the present invention. The compositions and single unit dosage forms can take the form of solutions, suspensions, emulsions, tablets, pills, capsules, powders, sustained-release formulations and the like. Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration.

Pharmaceutical compositions provided herein that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Typical oral dosage forms provided herein are prepared by combining a compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, microcrystalline cellulose, and mixtures thereof. Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof. Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonSeed oil, sunflower oil, sesame oil, olive oil, corn oil, and soybean oil), zinc stearate, ethyl oleate, ethyl laureate, agar, and mixtures thereof.

A compound can be administered by controlled release means or by delivery devices that are well known to those of ordinary skill in the art. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. The invention thus encompasses single unit dosage forms suitable for oral administration such as, but not limited to, tablets, capsules, gelcaps, and caplets that are adapted for controlled release.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

Pharmaceutical Methods

The invention relates to a method for post-transcriptionally modulating the expression of a target gene (i.e., mIGF1, ITGA7, or UTRN) in a human subject in need thereof, comprising administering an effective amount of a compound to the subject, in which said compound modulates the post-transcriptional expression of a nucleic acid construct comprising a reporter gene operably linked to any of the 5'-UTR and 3'-UTR, the 5'-UTR or the 3'-UTR of the target (i.e., mIGF1, ITGA7, or UTRN) in vitro or in cultured cells. In a specific embodiment, the method enhances or increases the post-transcriptional expression of the target gene (i.e., mIGF1, ITGA7, or UTRN) in a human subject. The present invention further relates to a method for treating MD or a form thereof, in a human subject in need thereof, comprising administering an effective amount of a compound to the subject, in which said compound enhances or increases the post-transcriptional expression of a nucleic acid construct comprising a reporter gene operably linked to any of the 5'-UTR and 3'-UTR, the 5'-UTR or the 3'-UTR of a target (i.e., mIGF1, ITGA7, or UTRN) in vitro or in cultured cells.

The present invention provides methods of treating MD, or a form thereof, in a human subject in need thereof, said methods comprising administering to the subject an effective amount of one or more compounds of the present invention. In specific embodiments, a compound is the only active ingredient administered to treat MD, or a form thereof. In a certain embodiment, a compound is the only active ingredient.

In some embodiments, a compound increases the amount of target protein (i.e., mIGF1, ITGA7, or UTRN) by about 5%, 10%, 15%, 20%, 25%, 35%, 45%, 50%, 55%, 65%, 70%, 75%, 80%, 85%, 90% or 95% relative to a negative control (e.g., PBS or DMSO). In some embodiments, a compound that is administered increases target mRNA (i.e., mIGF1, ITGA7, or UTRN) stability by about 5%, 10%, 15%, 20%, 25%, 35%, 45%, 50%, 55%, 65%, 70%, 75%, 80%, 85%, 90% or 95% relative to the negative control (i.e., mIGF1, ITGA7, or UTRN), as determined by mRNA stability assays (e.g., Northern blot or RT-PCR). In some embodiments, a compound that is administered increases target mRNA (i.e., mIGF1, ITGA7, or UTRN) translation by about 5%, 10%, 15%, 20%, 25%, 35%, 45%, 50%, 55%, 65%, 70%, 75%, 80%, 85%, 90% or 95% relative to a negative control as determined by assays known in the art, e.g., Western blotting, ELISA assay, flow cytometry.

In certain embodiments, the compound increases the amount or activity of said reporter protein by at least 1.5 fold, 2 fold, 3 fold, 4 fold, 5 fold, 6 fold, 7 fold, 8 fold, 9 fold, or 10 fold greater than the amount of activity of said reporter protein detected in the absence of the compound or in the presence of a negative control, as determined by an assay known in the art, e.g., ELISA, western blot, or FACs.

The effective amount of a compound used to enhance or increase the post-transcriptional expression of a target gene (i.e., mIGF1, ITGA7, or UTRN) depends on a number of factors, including but not limited to the type of MD, health and age of the patient, and toxicity or side effects. The present invention encompasses methods for treating MD, or a form thereof. The present invention also encompasses methods for treating MD, or a form thereof, as an alternative to other conventional therapies.

The present invention also provides methods of treating MD, or a form thereof, in a subject in need thereof, said methods comprising administering to the subject one or more of the compounds of the present invention and one or more additional agents. In a specific embodiment, one or more compounds of the present invention are administered to a subject in combination with a supportive therapy, a pain relief therapy, or other therapy that does not have an effect on MD or a form thereof.

The compounds and additional agent(s) of a combination product can be administered sequentially or concurrently. In one embodiment, a combination product or compositions (including pharmaceutical compositions) comprise a compound and at least one other agent which has the same mechanism of action as the compound. In another embodiment, a combination product comprises a compound and at least one other agent which has a different mechanism of action than the compound.

In a specific embodiment, a combination product or composition (including pharmaceutical compositions) described herein improves the prophylactic and/or therapeutic effect of an additional agent by functioning together with the agent to have an additive or synergistic effect. In another embodiment, a combination product or composition (including pharmaceutical compositions) described herein reduces the side effects associated with the compound or additional agent taken alone.

The compound(s) and additional agent(s) of a combination product or compositions can be administered to a subject in the same pharmaceutical composition. Alternatively, the compound(s) and additional agent of a combination product can be administered concurrently to a subject in separate pharmaceutical compositions. The components of a combination product may be administered to a subject by the same or different routes of administration.

In some embodiments, a compound of the present invention is administered to a subject suffering from MD, or a form thereof. In other embodiments, a compound is administered to a subject predisposed or susceptible to MD, or a form thereof. In an embodiment, the subject is suffering or predisposed or susceptible to any form of MD, including but not limited to, Duchenne Muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, and Emery-Dreifuss muscular dystrophy.

In certain embodiments, a compound is administered to a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, a compound is administered to a human infant. In other embodiments, a compound, is administered to a human toddler. In other embodiments, a compound is administered to a human child. In other embodiments, a compound is administered to a human adult. In yet other embodiments, a compound is administered to an elderly human.

In certain embodiments, a compound is administered to a subject in an immunocompromised state or immunosuppressed state or at risk for becoming immunocompromised or immunosuppressed. In certain embodiments, a compound is administered to a subject receiving or recovering from immunosuppressive therapy. In certain embodiments, a compound is administered to a subject that has or is at risk of getting cancer, AIDS, or a bacterial infection. In certain embodiments, the subject is, will or has undergone surgery, chemotherapy and/or radiation therapy. In certain embodiments, a compound is administered to a subject that has cystic fibrosis, pulmonary fibrosis or another condition affecting the lungs. In certain embodiments, a compound is administered to a subject that has, will have or had a tissue transplant.

In some embodiments, one or more compounds are administered to a patient to treat the onset of MD, or a form thereof, in a patient at risk of developing MD, or a form thereof. In some embodiments, one or more compounds are administered to a patient who are susceptible to adverse reactions to conventional therapies. In some embodiments, one or more compounds are administered to a patient who has proven refractory to product other than compounds, but are no longer on these therapies. In certain embodiments, the patient to be treated in accordance with the methods of this invention are patients already being treated with antibiotics, anti-virals, anti-fungals, or other biological therapy/immunotherapy. Among these patients are refractory patients, and patients who are too young for conventional therapies. In some embodiments, the subject being administered one or more compounds has not received therapy prior to the administration of the compounds.

The amount of a compound or a form or pharmaceutical composition thereof that increases the amount of any of a target protein (i.e., mIGF1, ITGA7 or UTRN) by modulating UTR-dependent expression of the target gene (i.e., mIGF1, ITGA7 or UTRN, respectively) that will be effective in the treatment MD, or a form thereof, can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

Exemplary effective amounts of a compound include milligram (mg) or microgram (µg) amounts per kilogram (Kg) of subject or sample weight per day such as from about 0.1 µg per Kg to about 500 mg per Kg per day, from about 1 µg per Kg to about 500 mg per Kg per day, from about 5 µg per Kg to about 100 mg per Kg per day, or from about 10 µg per Kg to about 100 mg per Kg per day. In specific embodiments, a daily dose is at least 0.1 mg, 0.5 mg, 1.0 mg, 2.0 mg, 5.0 mg, 10 mg, 25 mg, 50 mg, 75 mg, 100 mg, 150 mg, 250 mg, 500 mg, 750 mg, or at least 1 g. In another embodiment, the dosage is a unit dose of about 0.1 mg, 1 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 0.1 mg to about 1000 mg, 1 mg to about 1000 mg, 5 mg to about 1000 mg, about 10 mg to about 500 mg, about 100 mg to about 500 mg, about 150 mg to about 500 mg, about 150 mg to about 1000 mg, 250 mg to about 1000 mg, about 300 mg to about 1000 mg, or about 500 mg to about 1000 mg.

In certain embodiments, suitable dosage ranges for oral administration are about 0.001 milligram to about 500 milligrams of a compound, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound by weight.

In another embodiment, a subject is administered one or more doses of an effective amount of a compound or a composition, wherein the effective amount is not the same for each dose.

In one embodiment, a compound is administered to a patient in an amount effective to reduce loss of either or both muscle function and strength. In another embodiment, a compound is administered to a patient in an amount effective to increase either or both muscle function and strength. In another embodiment, a compound is administered to a patient to reduce loss of motor function. In yet another embodiment, a compound is administered to a patient to increase muscle strength. In an embodiment, a compound is administered to a patient to reduce loss of pulmonary function. In yet another embodiment, a compound is administered to increase pulmonary function.

The present invention also provides methods of treating MD, or a form thereof, in a subject in need thereof, said methods comprising administering to the subject an effective amount of one or more of the compounds that up-regulate the post-transcriptional expression of any of the target genes (i.e., mIGF1, ITGA7 or UTRN) alone or in combination with one or more additional agents. In another embodiment, one or more compounds or a form or pharmaceutical composition thereof that up-regulates the post-transcriptional expression of any of the target genes (i.e., mIGF1, ITGA7 or UTRN) alone or in combination with one or more additional agents may be administered to the subject in combination with a supportive therapy, a pain relief therapy, or other therapy that does not have an effect on MD or a form thereof.

In some embodiments, one or more compounds or a form or pharmaceutical composition thereof that up-regulates the post-transcriptional expression of any of the target genes (i.e., mIGF1, ITGA7 or UTRN) and one or more additional agents are administered as the same pharmaceutical composition. In certain embodiments, one or more compounds or a form or pharmaceutical composition thereof that up-regulates the post-transcriptional expression of any of the target genes (i.e., mIGF1, ITGA7 or UTRN) and one or more additional agents are administered in different pharmaceutical compositions. In certain embodiments, one or more compounds or a form or pharmaceutical composition thereof that up-regulates the post-transcriptional expression of any of the target genes (i.e., mIGF1, ITGA7 or UTRN) and one or more additional agents are administered by the same route of administration. In certain embodiments, one or more compounds or a form or pharmaceutical composition thereof that up-regulates the post-transcriptional expression of any of the target genes (i.e., mIGF1, ITGA7 or UTRN) and one or more additional agents are administered by different routes of administration.

Additional agents that can be used in a combination product with compounds that up-regulate any of the target genes (i.e., mIGF1, ITGA7 or UTRN) for the treatment of MD, or a form thereof, include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules.

Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

In some embodiments, additional agents that can be used in combination with the compounds described herein for the treatment of MD, or a form thereof, include, but are not limited to, agents that increase the transcription of the target gene (i.e., mIGF1, ITGA7 or UTRN). In certain embodiments, the agent is specific for the transcriptional promoter/enhancer of a target gene. In particular embodiments, the agent is specific for a transcription factor that binds to the transcriptional promoter/enhancer of a target gene and that increases transcription of the target gene. In some embodiments, the agent is specific for a transcriptional repressor that binds to the transcriptional promoter/enhancer of a target gene and inhibits transcription, or that binds to a transcription factor of a target gene and inhibits the activity of the transcription factor.

Additional agents that can be used in a combination product with compounds of the present invention for the treatment of MD, or a form thereof, include, but are not limited to, one or more agents that can improve functional and morphological aspects of muscles or that modulate other proteins involved in muscle growth and regeneration. Such agents include those that down-regulate or reduce the expression of GDF8 (myostatin, or growth and differentiation factor 8) to increase skeletal muscle mass.

In certain other embodiments, the present invention provides methods of treating MD, or a form thereof, in a subject in need thereof, said methods comprising administering to the subject one or more of the compounds that up-regulate (increase/enhance) the post-transcriptional expression of any of mIGF1, ITGA7 or UTRN gene alone or in combination with one or more additional agents each selected from an agent that decreases the expression of GDF8, a different agent that increases the expression of mIGF1, a different agent that increases the expression of α7 integrin, or a different agent that increases the expression of utrophin. In specific embodiments, such additional agent or different agent is not the same as a compound encompassed by the present invention, i.e., a compound that modulates the post-transcriptional expression of a target gene (i.e., mIGF1, ITGA7 or UTRN) via any one of the 5'-UTR, and/or 3'-UTR, or 5'-UTR, and 3'-UTR of the target (i.e., mIGF1, ITGA7 or UTRN).

Any compound or therapy which is known to be useful, or which has been used or is currently being used for the treatment of MD, or a form thereof, can be used in combination with compounds of the present invention as described herein.

EXAMPLES

As shown in the following examples, compounds that modulate the expression of proteins (e.g., mIGF1, ITGA7, or UTRN) have been identified or validated and have the potential to treat MD, or a form thereof. Stable muscle (RD) or kidney (293H) cell lines expressing the firefly luciferase (fLuc) reporter gene flanked by the 5'-UTR and 3'-UTR of mIGF1, ITGA7, or UTRN mRNA were constructed and used to identify or validate compounds able to specifically increase expression of a reporter gene via nucleic acid constructs comprising at least the 5'-UTR and 3'-UTR of mIGF1, ITGA7 or UTRN and to increase expression of endogenous mIGF1, ITGA7 or UTRN protein.

Example 1

Preparation of the Nucleic Acid Constructs Comprising the UTRs of mIGF1, ITGA7, and UTRN A high-level expression vector, pcDNA™3.1/Hygro (Invitrogen Corp., Carlsbad, Calif.) was used for preparing the constructs comprising the luciferase gene flanked by any of the 5'-UTR and 3'-UTR, the 5'-UTR or the 3'-UTR of mIGF1, ITGA7, and UTRN mRNA. In a pcDNA™3.1/Hygro vector, the UTRs and restriction sites normally associated with cloning and/or expressing a gene of interest or reporter gene were removed or replaced. For each construct containing 5' UTR sequences, the 5' UTR sequences with a start codon were cloned into the vector using the appropriate restriction sites.

Reporter Gene Assay $1 \times 10^4$ human embryonic kidney (293H) cells were added per well to 100 µL of medium in a 96-well plate and incubated for 24 hours. The constructs and a control construct were added to each well of the 96-well plate following the manufacturer's protocol using the following amounts of reagents per well: 62.5 ng pcDNA3.1-fluc-target UTRs vector, 3.1 ng Renilla luciferase vector, and 0.375 µL transfection reagent. The cells were incubated for 24 hours. The medium was then replaced with a new aliquot of culture medium and the cells were incubated for 24 hours. The effect of the UTRs on reporter gene expression was assessed by quantifying luciferase activity. Luciferase activity was measured by following the dual-luciferase protocol (Promega), wherein 1× passive lysis buffer was prepared, the cell culture medium was replaced with the 1× passive lysis buffer and incubated for 5 minutes, the substrate was added, and luminescence was measured.

Preparation of Stable Cell Lines

Stable 293H and RD cell lines containing the firefly luciferase (fLuc) gene flanked by mIGF1, ITGA7, or UTRN 5'-UTR and 3'-UTR were cultured in DMEM medium supplemented with 10% FBS and 200 µg/mL hygromycin in Fisher T175 flasks. The cells were passaged every 4 days at 1:10 dilution. Cultures were kept in a 37° C. and 5% $CO_2$ incubator. The cells were scaled-up three days before performing the assay. Two confluent T175 flasks were split into twenty T175 flasks (1:10 dilution). Cells were harvested from each confluent flask by removing all of the media and adding 4 mL of warmed trypsin to dislodge the cells. After the cells were dislodged, 16 mL of selective media was added for a final volume of 20 mL. The cells were expanded by adding 2 mL of the harvested cells into ten new T175 flasks plus 25 ml, of selective media. The twenty new flasks were placed into the 37° C., 5% $CO_2$ incubator. On the day the assay was performed, the media was removed from the flasks and 3 mL of warmed trypsin was added to dislodge the cells. After the cells were dislodged, 10 mL of nonselective media was added to the flask. This was repeated for all twenty flasks and combined into one flask. 100 µL of the above cell culture plus 100 µL of Trypan Blue stain was counted on a hemocytometer. 38 µL of cells (approximately 263 cells/4) were plated in the presence of 2 µL of a compound to be tested (at final concentration of 7.5 µM with 0.5% DMSO).

Preparation of Standard Plates

Standard 96-well clear Matrix Screen Mates plate were used. 459 µL of 100% DMSO was added to make a 100 mM solution. A fresh 30 mL 10% DMSO stock solution was made by adding 3 mL of 100% DMSO to 27 mL water. The 10% DMSO was used to make serial dilutions of a Puromycin stock solution so that the DMSO concentration remained at 10%.

Using standard techniques known to one skilled in the art, Puromycin was serially diluted to provide 10 mM Stock in 10% DMSO (by diluting 100 µL of 100 mM Stock with 900 µL water), 1 mM Stock in 10% DMSO (by diluting 500 µL of 10 mM Stock with 4.5 mL 10% DMSO), 400 µM Stock in 10% DMSO (by diluting 1.6 mL of 1 mM Stock with 2.4 mL 10% DMSO, 20 µM was final amount used in assay), 200 µM Stock in 10% DMSO (by diluting 1 mL of 400 µM Stock with 1 mL 10% DMSO, 10 µM was final amount used in assay), 100 µM Stock in 10% DMSO (by diluting 1 mL of 200 µM Stock with 1 mL 10% DMSO, 5 µM was final amount used in assay), 50 µM Stock in 10% DMSO (by diluting 1 mL of 100 µM Stock with 1 mL 10% DMSO, 2.5 µM was final amount used in assay), 25 µM Stock in 10% DMSO (by diluting 1 mL of 50 µM Stock with 1 mL 10% DMSO, 1.25 µM was final amount used in assay), 12.5 µM Stock in 10% DMSO (by diluting 1 mL of 25 µM Stock with 1 mL 10% DMSO, 0.625 µM was final amount used in assay), 6.25 µM Stock in 10% DMSO (by diluting 1 mL of 12.5 µM Stock with 1 mL 10% DMSO, 0.312 µM was final amount used in assay), 3.125 µM Stock in 10% DMSO (by diluting 1 mL of 6.25 µM Stock with 1 mL 10% DMSO, 0.156 µM was final amount used in assay) and 1.56 µM Stock in 10% DMSO (by diluting 1 mL of 3.125 µM Stock with 1 mL 10% DMSO, 0.078 µM was final amount used in assay).

The firefly luciferase substrate used was Luc Lite Plus Packard #6016969. Luciferase activity was immediately assayed using a ViewLux Imaging system (Perkin Elmer).

Cytotoxicity Assay

To evaluate cytotoxicity of the compounds in the 293H and RD cell lines, the CellTiter-Glo assay (Promega) is utilized. CellTiter-Glo determines the number of viable cells in culture based on quantification of the ATP present, which signals the presence of metabolically active cells. A reduction in cellular ATP is indicative of a cytotoxic or cytostatic effect. Doxorubicin, a known cytotoxic compound, is used to address the sensitivity of the tested cell line. For relatively sensitive cell lines, such as U937 (a human monocyte cell line), the $CC_{50}$ of doxorubicin ranges from 4 to 10 nM. For cell lines exhibiting an intermediate level of sensitivity to compound treatment such as human Huh7 cells (a human hepatoblastoma cell line), the $CC_{50}$ of doxorubicin ranges from 70 to 300 nM.

Results

The screening assay was performed by preparing plates containing test compounds and controls, including wells that contained only vehicle or a high inhibitor concentration and wells that provided an 8-point dose response curve of puromycin, a non-specific standard control inhibitor. The cells were grown overnight in the presence of compounds or controls at 37° C. in 5% $CO_2$. Compounds were screened once for percent inhibition at a 7.5 µM test concentration. After 24 hours, the amount of luminescence was determined using a ViewLux Imaging system (Perkin Elmer).

The results for compounds shown in the following tables indicate that the compounds of the present invention enhance post-transcriptional expression of a nucleic acid construct comprising a reporter gene operably linked to any of the 5'-UTR and 3'-UTR, the 5'-UTR or the 3'-UTR of the target mIGF1 mRNA (Table 1), ITGA7 mRNA (Table 2), or UTRN mRNA (Table 3).

Fold increase values in target mRNA for compounds tested compared to negative control (0.5% DMSO) are shown as follows: one star indicates less than one-fold increase in target mRNA, two stars indicate a greater than one-fold and up to two-fold increase in target mRNA, three stars indicate a greater than two-fold and up to three-fold increase in target mRNA and four stars indicate a greater than three-fold and up to four-fold increase in target mRNA.

TABLE 1

| Cpd | mIGF1 |
|---|---|
| 1 | ** |
| 2 | ** |
| 3 | * |
| 4 | *** |
| 5 | ** |
| 6 | * |
| 7 | *** |

TABLE 2

| Cpd | ITGa7 |
|---|---|
| 1 | ** |
| 2 | **** |
| 3 | * |
| 4 | *** |
| 5 | *** |
| 6 | * |
| 7 | **** |

TABLE 3

| Cpd | UTRN |
|---|---|
| 1 | ** |
| 2 | *** |
| 3 | ** |
| 4 | ** |
| 5 | *** |
| 6 | ** |
| 7 | ** |

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various patents, patent applications and publications are cited herein, the disclosures of which are incorporated by reference in their entireties.

What is claimed is:

1. A method for screening for a compound that modulates human ITGA7 translation that is regulated by the untranslated regions (UTRs) of the human α7 integrin (ITGA7) mRNA, the method comprising:

(a) contacting a compound with a first host cell engineered to express a first reporter protein translated from a first mRNA transcript comprising a first reporter gene coding sequence operably linked to a first 5'-UTR of human ITGA7 encoded by the nucleotide sequence of SEQ ID NO:3 and a first 3'-UTR of human ITGA7 encoded by the nucleotide sequence of SEQ ID NO:4, wherein the first 5'-UTR is upstream of the first reporter gene coding sequence and the first 3'-UTR is downstream of the first reporter gene coding sequence, and wherein the first reporter protein is not ITGA7, and wherein at least one compound is 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yf)phenol, N-(4-(benzo[d]thiazol-2-yl)phenylcarbamothioyl)-4-ethoxy-3-nitrobenzamide, 2-amino-4-(3-(trifluoromethyl)phenyl)-4H-benzo[h]chromene-3-carbonitrile, or N-(5-(benzo[d]thiazol-2-yl)-2-methylphenylcarbamothioyl)-4-butoxybenzamide; and (b) contacting the compound with a second host cell engineered to express a second reporter protein translated from a second mRNA transcript comprising the first reporter gene coding sequence operably linked to a second 5'-UTR and a second 3'-UTR of a mRNA different from the first 5'-UTR of human ITGA7 and the first 3'-UTR of human ITGA7, wherein the second 5'-UTR is upstream of the first reporter gene coding sequence and the second 3' UTR is downstream of the first reporter gene coding sequence; and (c) detecting the amount or activity of the first and second reporter protein, wherein (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human ITGA7 translation that is regulated by the UTRs of human ITGA7 mRNA.

2. The method of claim 1, wherein an increase in the amount or activity of the first reporter protein in the presence of the compound relative the amount or activity of the first reporter protein in the absence of the compound or the presence of a negative control indicates that the compound upregulates human ITGA7 translation that is regulated by the UTRs of human ITGA7 mRNA.

3. The method of claim 1, wherein the first and second host cells are a muscle cell.

4. The method of claim 1, wherein the first and second host cells are a RD cell, hybridoma, pre-B cell, 293 cell, 293T cell, 293H cell, HeLa cell, HepG2 cell, K562 cell, 3T3 cell, MCF7 cell, SkBr3 cell, BT474 cell, A204 cell, MC-IXC cell, SK-N-MC cell, SK-N-MC cell, SK-N-DZ cell, SH-SY5Y cell or BE(2)-C cell.

5. The method of claim 1, wherein the first and second host cells are stably transfected with a nucleic acid construct encoding the first and second mRNA transcripts, respectively.

6. A method for screening for a compound that modulates human ITGA7 translation that is regulated by the untranslated regions (UTRs) of human ITGA7 mRNA, the method comprising:
  (a) contacting a compound with a first composition comprising a first cell-free extract and a first mRNA transcript comprising a first reporter gene coding sequence operably linked to a first 5'-UTR of human ITGA7 encoded by the nucleotide sequence of SEQ ID NO:3 and a first 3'-UTR of human ITGA7 encoded by the nucleotide sequence of SEQ ID NO:4, wherein the first 5'-UTR is upstream of the first reporter gene coding sequence and the first 3'-UTR is downstream of the first reporter gene coding sequence, and wherein the first reporter coding sequence is not ITGA7, and wherein at least one compound is 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yl)phenol, N-(4-(benzo[d]thiazol-2-yl)phenylcarbamothioyl)-4-ethoxy-3-nitrobenzamide, 2-amino-4-(3-(trifluoromethyl)phenyl)-4H-benzo[h]chromene-3-carbonitrile, or N-(5-(benzo[d]thiazol-2-yl)-2-methylphenylcarbamothioyl)-4-butoxybenzamide; and
  (b) contacting the compound with a second composition comprising a second cell-free extract and a second mRNA transcript comprising the first reporter gene coding sequence operably linked to a second 5'-UTR and a second 3'-UTR of an mRNA different from the first 5'-UTR of human ITGA7 and the first 3'-UTR of human ITGA7, wherein the second 5'-UTR is upstream of the first reporter gene coding sequence and the second 3' UTR is downstream of the first reporter gene coding sequence; and
  (c) detecting the amount or activity of the first and second reporter proteins translated from the first and second mRNA transcripts, respectively, wherein (i) an alteration in the amount or activity of the first reporter protein in the presence of the compound relative to the amount or activity in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human ITGA7 translation that is regulated by the UTRs of human ITGA7 mRNA.

7. The method of claim 6, wherein an increase in the amount or activity of the first reporter protein in the presence of the compound relative the amount or activity of the first reporter protein in the absence of the compound or the presence of a negative control indicates that the compound upregulates human ITGA7 translation that is regulated by the UTRs of human ITGA7 mRNA.

8. The method of claim 6, wherein the first and second cell-free extracts are human cell-free extracts.

9. A method for screening for a compound that modulates human ITGA7 translation that is regulated by the untranslated regions (UTRs) of the human α7 integrin (ITGA7) mRNA, the method comprising:
  (a) contacting a compound with a first host cell engineered to express a first reporter protein translated from a first mRNA transcript comprising a first reporter gene coding sequence operably linked to a first 5'-UTR of human ITGA7 encoded by the nucleotide sequence of SEQ ID NO:3 and a first 3'-UTR of human ITGA7 encoded by the nucleotide sequence of SEQ ID NO:4, wherein the first 5'-UTR is upstream of the first reporter gene coding sequence and the first 3'-UTR is downstream of the first reporter gene coding sequence, and wherein the first reporter gene coding sequence is not ITGA7; and
  (b) contacting the compound with a second host cell engineered to express a second reporter protein translated from a second mRNA transcript comprising the first reporter gene coding sequence operably linked to a second 5'-UTR and a second 3'-UTR of an mRNA different from the first 5'-UTR of human ITGA7 and the first 3'-UTR of human ITGA7, wherein the second 5'-UTR is upstream of the first reporter gene coding sequence and the second 3'-UTR is downstream of the first reporter gene coding sequence;
  (c) detecting the amount or activity of the first and second reporter proteins, wherein (i) an alteration in the amount or activity of the first reporter protein in the presence of the compound relative to the amount or activity of the first reporter protein in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human ITGA7 translation that is regulated by the UTRs of human ITGA7 mRNA; and
  (d) the amount or activity of the first and second reporter proteins in the presence of the compound is compared to the amount or activity of the first and second reporter proteins in the presence of 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yl)phenol, N-(4-(benzo[d]thiazol-2-yl)phenylcarbamothioyl)-4-ethoxy-3-nitrobenzamide, 2-amino-4-(3-(trifluoromethyl)phenyl)-4H-benzo[h]chromene-3-carbonitrile, or N-(5-(benzo[d]thiazol-2-yl)-2-methylphenylcarbamothioyl)-4-butoxybenzamide.

10. The method of claim 9, wherein an increase in the amount or activity of the first reporter protein in the presence of the compound relative the amount or activity of the first reporter protein in the absence of the compound or the presence of a negative control indicates that the compound upregulates human ITGA7 translation that is regulated by the UTRs of human ITGA7 mRNA.

11. The method of claim 9, wherein the first and second host cells are a muscle cell.

12. The method of claim 9, wherein the first and second host cells are a RD cell, hybridoma, pre-B cell, 293 cell, 293T cell, 293H cell, HeLa cell, HepG2 cell, K562 cell, 3T3 cell, MCF7 cell, SkBr3 cell, BT474 cell, A204 cell, MC-IXC cell, SK-N-MC cell, SK-N-MC cell, SK-N-DZ cell, SH-SY5Y cell or BE(2)-C cell.

13. The method of claim 9, wherein the first and second host cells are stably transfected with a nucleic acid construct encoding the first and second mRNA transcripts, respectively.

14. A method for screening for a compound that modulates human ITGA7 translation that is regulated by the untranslated regions (UTRs) of human ITGA7 mRNA, the method comprising:
(a) contacting a compound with a first composition comprising a first cell-free extract and a first mRNA transcript comprising a first reporter gene coding sequence operably linked to a first 5'-UTR of human ITGA7 encoded by the nucleotide sequence of SEQ ID NO:3 and a first 3'-UTR of human ITGA7 encoded by the nucleotide sequence of SEQ ID NO:4, wherein the first 5'-UTR is upstream of the first reporter gene coding sequence and the first 3'-UTR is downstream of the first reporter gene coding sequence, and wherein the first reporter gene coding sequence is not ITGA7; and
(b) contacting the compound with a second composition comprising a second cell-free extract and a second mRNA transcript comprising the first reporter gene coding sequence operably linked to a second 5'-UTR and a second 3'-UTR of an mRNA different from the first 5'-UTR of human ITGA7 and the first 3'-UTR of human ITGA7, wherein the second 5'-UTR is upstream of the first reporter gene coding sequence and the second 3'-UTR is downstream of the first reporter gene coding sequence; and
(c) detecting the amount or activity of the first and second reporter proteins translated from the first and second mRNA transcripts, respectively, wherein (i) an alteration in the amount or activity of the first reporter protein in the presence of the compound relative to the amount or activity of the first reporter protein in the absence of the compound or the presence of a negative control, and (ii) no alteration in or not a substantially altered amount or activity of the second reporter protein in the presence of the compound relative to the amount or activity of the second reporter protein in the absence of the compound or the presence of the negative control indicates that the compound modulates human ITGA7 translation that is regulated by the UTRs of human ITGA7 mRNA; and
(d) the amount or activity of the first and second reporter proteins in the presence of the compound is compared to the amount or activity of the first and second reporter proteins in the presence of 4-(4-aminophenylthio)-6-chloropyrimidin-2-amine, N,N-dimethyl-4-(5-nitro-1H-benzo[d]imidazol-2-yl)aniline, 1-chloro-3-propyl-benzoimidazo[1,2-a]pyridine-4-carbonitrile, 3-(2,3-dihydro-1H-benzo[f]cyclopenta[c]quinolin-4-yl) phenol, N-(4-(benzo[d]thiazol-2-yl) phenylcarbamothioyl)-4-ethoxy-3-nitrobenzamide, 2-amino-4-(3-(trifluoromethyl)phenyl)-4H-benzo[h] chromene-3-carbonitrile, or N-(5-(benzo[d]thiazol-2-yl)-2-methylphenylcarbamothioyl)-4-butoxybenzamide.

15. The method of claim 14, wherein an increase in the amount or activity of the first reporter protein in the presence of the compound relative the amount or activity of the first reporter protein in the absence of the compound or the presence of a negative control indicates that the compound upregulates human ITGA7 translation that is regulated by the UTRs of human ITGA7 mRNA.

16. The method of claim 14, wherein the first and second cell-free extracts are human cell-free extracts.

* * * * *

SEQUENCE LISTING

<160> NUMBER OF SEQ ID NOS: 8

<210> SEQ ID NO 1
<211> LENGTH: 166
<212> TYPE: DNA
<213> ORGANISM: Homo sapiens
<220> FEATURE:
<223> OTHER INFORMATION: Human mIGF1 5 prime UTR

<400> SEQUENCE: 1

| tcactgtcac tgctaaattc agagcagatt agagcctgcg caatggaata aagtcctcaa | 60 |
|---|---|
| aattgaaatg tgacattgct ctcaacatct cccatctctc tggatttcct tttgcttcat | 120 |
| tattcctgct aaccaattca ttttcagact ttgtacttca gaagca | 166 |

<210> SEQ ID NO 2
<211> LENGTH: 6632
<212> TYPE: DNA
<213> ORGANISM: Homo sapiens
<220> FEATURE:
<223> OTHER INFORMATION: Human mIGF1 3 prime UTR

<400> SEQUENCE: 2

| gaagaccctc ctgaggagtg aagagtgaca tgccaccgca ggatcctttg ctctgcacga | 60 |
|---|---|
| gttacctgtt aaactttgga acacctacca aaaataagt ttgataacat ttaaaagatg | 120 |
| ggcgtttccc ccaatgaaat acacaagtaa acattccaac attgtctttta ggagtgattt | 180 |
| gcaccttgca aaaatggtcc tggagttggt agattgctgt tgatcttta tcaataatgt | 240 |
| tctatagaaa agaaaaaaa atatatatat atatatatct tagtccctgc ctctcaagag | 300 |
| ccacaaatgc atgggtgttg tatagatcca gttgcactaa attcctctct gaatcttggc | 360 |
| tgctggagcc attcattcag caaccttgtc taagtggttt atgaattgtt tccttatttg | 420 |
| cacttctttc tacacaactc gggctgtttg ttttacagtg tctgataatc ttgttagtct | 480 |
| atacccacca cctcccttca taacctttat atttgccgaa tttggcctcc tcaaaagcag | 540 |
| cagcaagtcg tcaagaagca caccaattct aacccacaag attccatctg tggcatttgt | 600 |
| accaaatata agttggatgc atttatttt agacacaaag ctttatttt ccacatcatg | 660 |
| cttacaaaaa agaataatgc aaatagttgc aactttgagg ccaatcattt ttaggcatat | 720 |
| gttttaaaca tagaaagttt cttcaactca aaagagttcc ttcaaatgat gagttaatgt | 780 |
| gcaacctaat tagtaacttt cctctttta ttttttccat atagagcact atgtaaattt | 840 |
| agcatatcaa ttatacagga tatatcaaac agtatgtaaa actctgtttt ttagtataat | 900 |
| ggtgctattt tgtagtttgt tatatgaaag agtctggcca aaacggtaat acgtgaaagc | 960 |
| aaaacaatag gggaagcctg gagccaaaga tgacacaagg ggaagggtac tgaaaacacc | 1020 |
| atccatttgg gaaagaaggc aaagtccccc cagttatgcc ttccaagagg aacttcagac | 1080 |
| acaaaagtcc actgatgcaa attggactgg cgagtccaga gaggaaactg tggaatggaa | 1140 |
| aaagcagaag gctaggaatt ttagcagtcc tggtttcttt ttctcatgga agaaatgaac | 1200 |
| atctgccagc tgtgtcatgg actcaccact gtgtgacctt gggcaagtca cttcacctct | 1260 |
| ctgtgcctca gtttcctcat ctgcaaaatg ggggcaatat gtcatctacc tacctcaaag | 1320 |
| gggtggtata aggtttaaaa agataaagat tcagatttt ttaccctggg ttgctgtaag | 1380 |
| ggtgcaacat cagggcgctt gagttgctga gatgcaagga attctataaa taacccattc | 1440 |
| atagcatagc tagagattgg tgaattgaat gctcctgaca tctcagttct tgtcagtgaa | 1500 |
| gctatccaaa taactggcca actagttgtt aaaagctaac agctcaatct cttaaaacac | 1560 |

```
ttttcaaaat atgtgggaag catttgattt tcaatttgat tttgaattct gcatttggtt    1620
ttatgaatac aaagataagt gaaagagag aaggaaaag aaaaaggaga aaacaaaga       1680 gatttctacc agtgaaaggg gaattaatta ctctttgtta gcactcactg actcttctat    1740
gcagttacta catatctagt aaaaccttgt ttaatactat aaataatatt ctattcattt    1800
tgaaaaacac aatgattcct tcttttctag gcaatataag gaaagtgatc caaaatttga    1860
aatattaaaa taatatctaa taaaaagtca caaagttatc ttctttaaca aactttactc    1920
ttattcttag ctgtatatac attttttta aaagtttgtt aaaatatgct tgactagagt     1980
ttcagttgaa aggcaaaaac ttccatcaca acaagaaatt tcccatgcct gctcagaagg    2040 gtagcccta gctctctgtg aatgtgtttt atccattcaa ctgaaaattg gtatcaagaa     2100
agtccactgg ttagtgtact agtccatcat agcctagaaa atgatcccta tctgcagatc    2160
aagattttct cattagaaca atgaattatc cagcattcag atctttctag tcaccttaga    2220
actttttggt taaaagtacc caggcttgat tatttcatgc aaattctata ttttacattc    2280
ttggaaagtc tatatgaaaa acaaaaataa catcttcagt ttttctccca ctgggtcacc    2340
tcaaggatca gaggccagga aaaaaaaaa agactccctg gatctctgaa tatatgcaaa     2400
aagaaggccc catttagtgg agccagcaat cctgttcagt caacaagtat tttaactctc    2460
agtccaacat tatttgaatt gagcacctca agcatgctta gcaatgttct aatcactatg    2520
gacagatgta aaagaaacta tacatcattt ttgccctctg cctgttttcc agacatacag    2580
gttctgtgga ataagatact ggactcctct tcccaagatg gcacttcttt ttatttcttg    2640
tccccagtgt gtacctttta aaattattcc ctctcaacaa aactttatag gcagtcttct    2700
gcagacttaa catgttttct gtcatagtta gatgtgataa ttctaagagt gtctatgact    2760
tatttccttc acttaattct atccacagtc aaaaatcccc caaggaggaa agctgaaaga    2820
tgcaactgcc aatattatct ttcttaactt ttttccaacac ataatcctct ccaactggat    2880
tataaataaa ttgaaaataa ctcattatac caattcacta ttttattttt taatgaatta    2940
aaactagaaa acaaattgat gcaaaccctg gaagtcagtt gattactata tactacagca    3000
gaatgactca gatttcatag aaaggagcaa ccaaaatgtc acaaccaaaa ctttacaagc    3060
tttgcttcag aattagattg ctttataatt cttgaatgag gcaatttcaa gatatttgta    3120
aaagaacagt aaacattggt aagaatgagc tttcaactca taggcttatt ccaatttaa    3180 ttgaccatac tggatactta ggtcaaattt ctgttctctc ttgcccaaat aatattaaag    3240
tattatttga actttttaag atgaggcagt tccctgaaa aagttaatgc agctctccat     3300
cagaatccac tcttctaggg atatgaaaat ctcttaacac ccaccctaca tacacagaca    3360
cacacacaca cacacacaca cacacacaca cacacacatt caccctaagg atccaatgga    3420
atactgaaaa gaaatcactt ccttgaaaat tttattaaaa aacaaacaaa caaacaaaaa    3480
gcctgtccac ccttgagaat ccttcctctc cttggaacgt caatgttgt gtagatgaaa     3540 ccatctcatg ctctgtggct ccagggtttc tgttactatt ttatgcactt gggagaaggc    3600
ttagaataaa agatgtagca catttgtgctt tcccatttat tgtttggcca gctatgccaa   3660
tgtggtgcta ttgtttcttt aagaaagtac ttgactaaaa aaaaagaaa aaagaaaaa      3720 aagaaagca tagacatatt ttttaaagt ataaaacaa caattctata gatagatggc       3780
ttaataaaat agcattaggt ctatctagcc accaccacct tcaacttttt tatcactcac    3840
aagtagtgta ctgttcacca aattgtgaat ttggggggtgc aggggcagga gttggaaatt   3900
```

```
tttaaagtt agaaggctcc attgttttgt tggctctcaa acttagcaaa attagcaata    3960
tattatccaa tcttctgaac ttgatcaaga gcatggagaa taaacgcggg aaaaaagatc    4020
ttataggcaa atagaagaat ttaaaagata agtaagttcc ttattgattt ttgtgcactc    4080
tgctctaaaa cagatattca gcaagtggag aaaataagaa caaagagaaa aaatacatag    4140
atttacctgc aaaaaatagc ttctgccaaa tcccccttgg gtattctttg gcatttactg    4200
gtttatagaa gacattctcc cttcacccag acatctcaaa gagcagtagc tctcatgaaa    4260
agcaatcact gatctcattt gggaaatgtt ggaaagtatt tccttatgag atgggggtta    4320
tctactgata agaaagaat ttatgagaaa ttgttgaaag agatggctaa caatctgtga    4380
agattttttg tttcttggtt ttgttttttt tttttttttt actttataca gtctttatga    4440
atttcttaat gttcaaaatg acttggttct tttcttcttt tttttatatc agaatgagga    4500
ataataagtt aaacccacat agactcttta aaactatagg ctagatagaa atgtatgttt    4560
gacttgttga agctataatc agactattta aaatgttttg ctattttta tcttaaaaga    4620
ttgtgctaat ttattagagc agaacctgtt tggctctcct cagaagaaag aatctttcca    4680
ttcaaatcac atggctttcc accaatattt tcaaaagata aatctgattt atgcaatggc    4740
atcatttatt ttaaaacaga agaattgtga agtttatgc ccctcccttg caaagaccat    4800
aaagtccaga tctggtaggg gggcaacaac aaaaggaaaa tgttgttgat tcttggtttt    4860
ggattttgtt ttgttttcaa tgctagtgtt taatcctgta gtacatattt gcttattgct    4920
atttaatat tttataagac cttcctgtta ggtattagaa agtgatacat agatatcttt    4980
tttgtgtaat ttctatttaa aaagagaga agactgtcag aagctttaag tgcatatggt    5040
acaggataaa gatatcaatt taaataacca attcctatct ggaacaatgc ttttgttttt    5100
taaagaaacc tctcacagat aagacagagg cccaggggga ttttgaagct gtctttattc    5160
tgcccccatc ccaacccagc ccttattatt ttagtatctg cctcagaatt ttatagaggg    5220
ctgaccaagc tgaaactcta gaattaaagg aacctcactg aaaacatata ttcacgtgt    5280
tccctctctt tttttttcctt tttgtgagat ggggtctcgc actgtccccc aggctggagt    5340
gcagtggcat gatctcggct cactgcaacc tccacctcct gggtttaagc gattctcctg    5400
cctcagcctc ctgagtagct gggattacag gcacccacca ctatgcccgg ctaatttttt    5460
ggattttta tagagacggg gttttaccat gttggccagg ttggactcaa actcctgacc    5520
tgtgatttg cccgcctcag cctcccaaat tgctgggatt acaggcatga gccaccacac    5580
cctgcccatg tgttccctct taatgtatga ttacatggat cttaaacatg atccttctct    5640
cctcattctt caactatctt tgatggggtc tttcaagggg aaaaaaatcc aagctttttt    5700
aaagtaaaaa aaaaaaaaga gaggacacaa aaccaaatgt tactgctcaa ctgaaatatg    5760
agttaagatg gagacagagt ttctcctaat aaccggagct gaattacctt tcactttcaa    5820
aaacatgacc ttccacaatc cttagaatct gccttttttt atattactga ggcctaaaag    5880
taaacattac tcattttatt ttgcccaaaa tgcactgatg taaagtagga aaaataaaaa    5940
cagagctcta aaatcccttt caagccaccc attgacccca ctcaccaact catagcaaag    6000
tcacttctgt taatccctta atctgatttt gtttggatat ttatcttgta cccgctgcta    6060
aacacactgc aggagggact ctgaaacctc aagctgtcta cttacatctt ttatctgtgt    6120
ctgtgtatca tgaaaatgtc tattcaaaat atcaaaacct ttcaaatatc acgcagctta    6180
tattcagttt acataaaggc cccaaatacc atgtcagatc ttttttggtaa aagagttaat    6240
gaactatgag aattgggatt acatcatgta ttttgcctca tgtatttta tcacacttat    6300
```

```
aggccaagtg tgataaataa acttacagac actgaattaa tttcccctgc tactttgaaa    6360
ccagaaaata atgactggcc attcgttaca tctgtcttag ttgaaaagca tattttttat    6420
taaattaatt ctgattgtat ttgaaattat tattcaattc acttatggca gaggaatatc    6480
aatcctaatg acttctaaaa atgtaactaa ttgaatcatt atcttacatt tactgtttaa    6540
taagcatatt ttgaaaatgt atggctagag tgtcataata aaatggtata tctttcttta    6600
gtaattacaa aaaaaaaaaa aaaaaaaaaa aa                                   6632

<210> SEQ ID NO 3
<211> LENGTH: 161
<212> TYPE: DNA
<213> ORGANISM: Homo sapiens
<220> FEATURE:
<223> OTHER INFORMATION: Human Alpha-7 integrin(ITGA7) 5 prime UTR

<400> SEQUENCE: 3
ggagcggcgg gcgggcggga gggctggcgg ggcgaacgtc tgggagacgt ctgaaagacc      60
aacgagactt tggagaccag agacgcgcct gggggggacct ggggcttggg gcgtgcgaga    120
tttcccttgc attcgctggg agctcgcgca gggatcgtcc c                         161

<210> SEQ ID NO 4
<211> LENGTH: 504
<212> TYPE: DNA
<213> ORGANISM: Homo sapiens
<220> FEATURE:
<223> OTHER INFORMATION: Human Alpha-7 integrin(ITGA7) 3 prime UTR

<400> SEQUENCE: 4
gttcccatgt cccagcctgg cctgtggctg ccctccatcc cttccccaga gatggctcct      60
tgggatgaag agggtagagt gggctgctgg tgtcgcatca agatttggca ggatcggctt    120
cctcaggggc acagacctct cccacccaca agaactcctc ccacccaact tcccccttaga    180 gtgctgtgag atgagagtgg gtaaatcagg gacagggcca tggggtaggg tgagaagggc    240
aggggtgtcc tgatgcaaag gtggggagaa gggatcctaa tcccttcctc tcccattcac    300
cctgtgtaac aggaccccaa ggacctgcct ccccggaagt gccttaacct agagggtcgg    360
ggaggaggtt gtgtcactga ctcaggctgc tccttctcta gtttcccctc tcatctgacc    420
ttagtttgct gccatcagtc tagtggtttc gtggtttcgt ctatttatta aaaaatattt    480
gagaacaaaa aaaaaaaaaa aaaa                                            504

<210> SEQ ID NO 5
<211> LENGTH: 497
<212> TYPE: DNA
<213> ORGANISM: Homo sapiens
<220> FEATURE:
<223> OTHER INFORMATION: Utrophin 5 prime UTR

<400> SEQUENCE: 5
ttgtggagtc gttttttcctc ggagcaggga agcgggcagc agcagccggc cgcgggcttt      60
ctcccgccga ggggcgagga ggagcctctg gctccagaag ccgattgggg aatcacgggg    120
agcggcgccc cccttctttt gggtcatttc tgcaaacgga aaactctgta gcgtttggca    180
aagttggtgc ctgcgcgccc cttccaggtt tgcgctttga ctgttttgtt tttggcggaa    240
ctaccaggca ggaagattgc acaagtaagg ggcgttttca gtcgggtgtc aatttctctt    300
tctttctttc ttttttaaa atttcggttc gtgtctgctc ctccaagctt tattttttt     360
```

```
ttaaaataca tcgcaccacc aaactaacac tcgcacacac ccccgcggtt actccgtgtc    420
aaactcctag aggagcccct tggccagctcg gggtgcggcg gtggcgaccg gcaggcgagg    480
aggcccgcgg gcagcag                                                    497

<210> SEQ ID NO 6
<211> LENGTH: 860
<212> TYPE: DNA
<213> ORGANISM: Homo sapiens
<220> FEATURE:
<223> OTHER INFORMATION: Utrophin 3 prime UTR

<400> SEQUENCE: 6
gtgaagtatt catccggcca accaatgttt cctgacgtac agtgttgccc ttttcagcaa     60
atgccaattc caagttccat taaatcagaa gctccatggc tccttggccc acgatgttga    120
gtgctgactg tgtgttctac tgaaagagta aacactgac tatccaaaga gaaatggata    180
ttttgttttt ataataacca tatattattg ttttcttctt ccctttctat gcaagtgtaa    240
attaatgaac agagaggtat tggaaatgg taatacattt gtcacggatt tgtataatgt    300
atacagcatt gggaaagtgg gtggggcctt ctaatatga taccgtcttt ttaataacta    360
tgacaaagct tacataagaa ttagaagacc actttacatt tttacattcc ttctgctgtt    420
catattaacc ttgcacaatt acttcatttt tctttgact cttttaccac aatgttttgg    480
ttatttataa tttatcagcc atatgtttat cagccatata accaactaga tcccaaatag    540
atccatgtat ttgtttccgt gatttggcca cattaataaa ttcataaatt tcaatcaaat    600
atcttatata tacacacata tggtttaagc tacagccctg tgtatgccgt taactttat    660 ttgacgttgc ccacttactt ctttgctgac cacttggata accgtaataa aaatcctata    720
agcctaaatg gcatttcttt tgggatattt ttcctgcatt ttattccctt tttatataag    780
taggaattaa ttatttattt tatgtcttaa tctatttgat aaagaagact acattataat    840
aatctcaaag atcatattac                                                 860

<210> SEQ ID NO 7
<211> LENGTH: 2073
<212> TYPE: DNA
<213> ORGANISM: mouse
<220> FEATURE:
<223> OTHER INFORMATION: mouse UTRN 3 prime UTR sequence

<400> SEQUENCE: 7
tgaagtattc atccggccaa ccaatgtttc ctgacgtaca gtgttgccct tttcagcaaa     60
tgccaattcc aagttccatt aaatcagaag ctccatggct ccttggccca cgatgttgag    120
tgctgactgt gtgttctact gaaagagtaa acactgact atccaaagag aaatggatat    180
tttgttttta taataaccat atattattgt tttcttcttc cctttctatg caagtgtaaa    240
ttaatgaaca gagaggtatt tggaaatggt aatacatttg tcacggattt gtataatgta    300
tacagcattg ggaaagtggg tggggcttt ctaatatgat accgtctttt taataactat    360
gacaaagctt acataagaat tagaagacca ctttacattt ttacattcct tctgctgttc    420
atattaacct tgcacaatta cttcattttt tctttgactc ttttaccaca atgttttggt    480
tatttataat ttatcagcca tatgtttatc agccatataa ccaactagat cccaaataga    540
tccatgtatt tgtttccgtg atttggccac attaataaat tcataaattt caatcaaata    600
tcttatatat acacacatat ggtttaagct acagccctgt gtatgccgtt aactttatt    660 tgacgttgcc cacttacttc tttgctgacc acttggataa ccgtaataaa aatcctataa    720
```

-continued

```
gcctaaatgg catttctttt gggatatttt tcctgcattt tattcccttt ttatataagt    780
aggaattaat tatttatttt atgtcttaat ctatttgata agaagactac cattataata    840
atctcaaaga tcatattacc aaaggttgcc cacttgagca tattttcatt ttgacacaga    900
aacaaaattt agtacaacct ttcctagttc ccatgtcttg attttcatca ttacatgcac    960
agcagacctt taccattgt gataccagaa cacatcattg tctttggttc ccttcaaaga   1020 gaatttatt gttgttttgt attttcaagt ccttaatagt tcttgaaact cctagttgtt   1080
ttcttgttga aagcagacac acatttagtg cacggcttat tttacccttc gggtgaaaga   1140
tcagatgttt ttatacccctt cacttgatca atatatttgg aaagaatgtt tatcaaaagt   1200
ctatgtcact gcttctacag aagaatgaaa ttaatgctta ggtgatggta cctccaccta   1260
catctttttg agtgcattca attatgtatt ttggtttagc ttctgattta acatttaatt   1320
gattcagttt aaacatgtta cttaattagc aaatgtagag gaaccaaaaa aaggtgaaaa   1380
taatatgttt tgattcaaac ctaaagacat aaaaacataa agacatttta actttgggtt   1440
ctctttagct gggatctggc cagaaggagg cttaaagtta gaaattgcta ttattttaga   1500
ataggttggg tgggttgggg ggcaagggtg tctatttgca gcagagatat tttgaaaaga   1560
agaaaattgt tttatataaa aaggaaagcc atgaccacct ttctacctca gatccatctt   1620
catccattgc attggaaact gctttatgct gctgcagtct gcaaagtcta gagcttttat   1680
caggccatgt catacccaag aaagcaccta tttaagaaa aaacaattcc ctgagctctc   1740
aactccaagt tgtagatttg gtgtcttcct tgttcttact ttaaaaagtc atgtgttaat   1800
tttttttctg cctgtatttg tatgcaaaat gtcctctatc tgctattaaa gaaaagctac   1860
gtaaaacact acattgtaac cttctaagta ataataaata aaaagaaata tattgcagta   1920
acaatgggaa gtaagtatgt agttcttttg aaatatgtgg taaagaacta atcacagact   1980
atcatctaat ctggttacat attgtatttt tcatcctgaa taaaagtaat tttaacacaa   2040
gatgactttg atattcttca gctggattca ctg                               2073
```

<210> SEQ ID NO 8
<211> LENGTH: 2055
<212> TYPE: DNA
<213> ORGANISM: Artificial Sequence
<220> FEATURE:
<223> OTHER INFORMATION: human UTRN 3 prime UTR sequence

<400> SEQUENCE: 8

```
tgagcatcta tccagccagc caacatttcc cgaccttcag tattgccctc ttctgcaaat     60
gccaatccca agaccccattc aaccccaaag ctccgtggct ccacgacaca agctgttgag    120
tgcttactgg gtgttctact gagggaacca aacactgact atccaaagag aaaaggatat    180
tttggttttc taataacgta tattattgtt ttcttctccc ctttctatgc aactgtaaat    240
taatgaacac agaagtattt ggaggtggta aagcatttgt cactgatttg tataatatat    300
acagccatgg gaaagtgggt gggggctttc taatatgaaa ctgtcttttt aataaccaag    360
agaaaaaatt gcataagaat tagaccactt tacattatta cattccttct gctgttcaca    420
ttaaccttgt acaataactt cacttattat ttgactgttt taccattatg ttttggttat    480
ttattaaatt tatcagccat acaaacaaat agattctatg tatttgtttc tataatctgg    540
ccaaattcct aagttcatat atttgaatca aatattttac atatgtggag taggcaggca    600
ttctgaagat actatttaac tttagttgac gtcacacaca ccatcccttta gtaaccactg    660
```

-continued

```
gatgactaca ctaaaaatcc tgtggactttt aacggcaagc tgctggggta tttttcctcc   720 tgttttatt cctttttgta agtagatctt gacgtcttta tttatttcat cttgcaatct     780
ctataataaa gaagactgta ttgtaatagt ctcaaaaaat tattttacca agggttacca    840
tttaagcata ttttcatttt gattcagaaa ccaaagttgg tacaacctct cctagtactt    900
gcaaccttgg ttttcatgag aaaacacacg gcaggctttg cccattgtga ggagagcaca   960
catcatgctc ttcagtttcc ctttgaatag acttttattg ttgttttttgt attttcgag   1020 tcctgtgtaa gttttgaaag ctctggttgt tctttgtgaa agcaggcaga tacttattgg   1080
ctgtctcatt tgaagctttg gagcagatag tcagatgtct catgacccct cacttggcca   1140
gcagcacatc cgagaaggat gtcactcaca agcctacacc acggcttctc tagaatgaaa   1200
tcagcacatc cgagaaggat gtcactcaca agcctacacc acggttctct agaatgaaat   1260
cagtgctcgg atgattgtat ccctgcctct acttctgagt gtgttcaact aggtattggc   1320 ttcttttttct ttttcttttc tttttttttt aatttaacac ttaattgccg atttttagaga  1380 aaccaaaaat aaaggtgaag gtaatatgtt ttgattcaaa catatatgct tttaaaacat   1440
caggacatgc taactttggg ttctctttca ctgggatctg gccagaagga ggctgaaagt   1500
tagaaattgc tattctttta cgatcggttg ggtgggttgg ggggcaatgg tgtctatttg   1560
cagcatagat attttgagac gaagaaaatt gttttatata aggggagagc catgatcacc   1620
tttctacctc agaaccacct tcctccattg tgttggacat agctttatat gccgcagtgt   1680
gcaaaaccta gggctgtagt caggcctttc catacccagg aagcacctgt gtaaagaaga   1740
tcaacagaaa ctcccggaac tcagaacccc aagttgtaga tttggtgtcg tccttgttct   1800
tgctttgagg agtcatgtat tctttttattt cctgcctgta tttgtatgca aaatgatctc  1860
tatctgctat tacagaaaaa gctacacaaa acactacatt gtaaccttct gagtaataaa   1920
taagaggaaa tatattacag taaccatgat gagaaataag tgtattgttc ttttgaaata   1980
tgtggttaat cgcagactgt catctaatct gttacatacc gtattttttca tcctgaataa   2040 aagtaatttt aacac                                                     2055
```